(12) United States Patent
Walsh et al.

(10) Patent No.: US 11,198,738 B2
(45) Date of Patent: *Dec. 14, 2021

(54) THERAPEUTIC ANTIBODIES AND USES THEREOF

(71) Applicant: Minomic International Ltd., Macquarie Park (AU)

(72) Inventors: Bradley Walsh, Turramurra (AU); Douglas Campbell, North Sydney (AU); Sandra Wissmueller, Currans Hills (AU)

(73) Assignee: Minomic International Ltd., New South Wales (AU)

( * ) Notice: Subject to any disclaimer, the term of this patent is extended or adjusted under 35 U.S.C. 154(b) by 627 days.

This patent is subject to a terminal disclaimer.

(21) Appl. No.: 15/567,889

(22) PCT Filed: Apr. 20, 2016

(86) PCT No.: PCT/AU2016/000136
§ 371 (c)(1),
(2) Date: Oct. 19, 2017

(87) PCT Pub. No.: WO2016/168885
PCT Pub. Date: Oct. 27, 2016

(65) Prior Publication Data
US 2019/0010247 A1 Jan. 10, 2019

(30) Foreign Application Priority Data
Apr. 20, 2015 (AU) .................. 2015901423

(51) Int. Cl.
| | |
|---|---|
| C07K 16/30 | (2006.01) |
| A61K 47/68 | (2017.01) |
| A61K 51/10 | (2006.01) |
| A61P 35/00 | (2006.01) |
| A61K 38/08 | (2019.01) |
| A61K 39/00 | (2006.01) |

(52) U.S. Cl.
CPC .......... *C07K 16/3069* (2013.01); *A61K 38/08* (2013.01); *A61K 47/6817* (2017.08); *A61K 47/6849* (2017.08); *A61K 47/6851* (2017.08); *A61K 47/6859* (2017.08); *A61K 47/6861* (2017.08); *A61K 47/6869* (2017.08); *A61K 47/6889* (2017.08); *A61K 51/106* (2013.01); *A61K 51/1027* (2013.01); *A61K 51/1045* (2013.01); *A61K 51/1057* (2013.01); *A61K 51/1072* (2013.01); *A61K 51/1093* (2013.01); *A61K 51/1096* (2013.01); *A61P 35/00* (2018.01); *C07K 16/30* (2013.01); *C07K 16/303* (2013.01); *C07K 16/3038* (2013.01); *A61K 2039/505* (2013.01); *C07K 2317/24* (2013.01); *C07K 2317/56* (2013.01); *C07K 2317/565* (2013.01); *C07K 2317/622* (2013.01); *C07K 2317/73* (2013.01); *C07K 2317/77* (2013.01); *C07K 2317/92* (2013.01)

(58) Field of Classification Search
CPC ........ C07K 16/00–468; C07K 16/3069; A61K 47/6889; A61K 47/6851; A61K 47/6861; A61K 47/6869
See application file for complete search history.

(56) References Cited

U.S. PATENT DOCUMENTS

| | | | | |
|---|---|---|---|---|
| 5,622,836 | A | * | 4/1997 | Walker ................ A61K 51/106 435/344 |
| 10,151,754 | B2 | * | 12/2018 | Walsh ............ C12Y 304/21077 |
| 10,577,418 | B2 | * | 3/2020 | Campbell ................ C12N 5/16 |
| 2003/0103980 | A1 | | 6/2003 | Korc et al. |
| 2019/0120846 | A1 | * | 4/2019 | Walsh .............. G01N 33/57434 |

FOREIGN PATENT DOCUMENTS

| | | |
|---|---|---|
| WO | 9014433 A1 | 11/1990 |
| WO | 2005016285 A2 | 2/2005 |
| WO | 2014165506 A1 | 10/2014 |
| WO | 2015106311 A1 | 7/2015 |
| WO | 2016061608 A1 | 4/2016 |
| WO | 2016112423 A1 | 7/2016 |

OTHER PUBLICATIONS

Wang et al., Mol Cancer Ther 10(9): 1728-39 (Year: 2011).*
International Search Report for corresponding PCT Application No. PCT/AU2016/000136 dated Sep. 20, 2016.
Wissmueller, S. et al., "Development of an antibody based test for the diagnosis of prostate cancer", BJU International, Mar. 2014, vol. 113, Supp. 4, p. 45, Abstract No. 90.
Duan, L. et al., "GPC-1 may serve as a predictor of perineural invasion and prognosticator of survival in pancreatic cancer", Asian Journal of Surgery, Jan. 2013, vol. 36, Issue 1, pp. 7-12.
International Written Opinion for corresponding PCT Application No. PCT/AU2016/000136, dated Sep. 20, 2016.
Li et al., "Antigenic Expression of Human Metastatic Prostate Cancer Cell Lines for in Vitro Multiple-Targeted a-Therapy With 2 13 Bi-Conjugates", Int. J. Radiation Oncology Biol. Phys., vol. 60, No. 3, pp. 896-908, 2004.
Carter et al., "Biodistributions of intact monoclonal antibodies and fragments of BLCA-38, a new prostate cancer directed antibody", Cancer Immunol Immunother (2004) 53: 533-542 DOI I 0.1007/s00262-003-0460-I; XP-002447896.

(Continued)

*Primary Examiner* — Jessica H Roark
(74) *Attorney, Agent, or Firm* — Wood, Phillips, Katz, Clark & Mortimer

(57) ABSTRACT

The present invention relates to therapeutic antibodies for the treatment of cancer, and more specifically, for the treatment of prostate, bladder, and/or pancreatic cancer. An embodiment of the present invention is an anti-glypican-1 (GPC 1) antibody, which may be conjugated to at least one cytotoxic agent that is toxic to a prostate, bladder, and/or pancreatic cancer cell.

9 Claims, 28 Drawing Sheets
Specification includes a Sequence Listing.

(56) References Cited

OTHER PUBLICATIONS

Russell et al., "Immunohistochemical characterisation of the monoclonal antibody BLCA-38 for the detection of prostate cancer", Cancer Immunol Immunother (2004) 53: 995-1004, DOI 10.1007/s00262-004-0527-7.

Sayyadi et al., "Sensitive Time-Gated Immunoluminescence Detection of Prostate Cancer Cells Using a TEGylated Europium Ligand", American Chemical Society, 2016, 88, 9564-9571; ACS Publications.

Khatri et al., "Promise of BLCA38 as a Targeting Antibody for Tissue-Specific Gene Delivery to Prostate Cancer", Austral—Asian Journal of Cancer ISSN-0972-2556, vol. 9, No. 3, Jul. 2010 196.

Matsuzaki et al., "Anti-glypican-1 antibody-drug conjugate exhibits potent preclinical antitumor activity against glypican-1 positive uterine cervical cancer", Int. J. Cancer: 142, 1056-1066 (2018).

Huang et al., "Glypican—1—antibody-conjugated Gd—Au nanoclusters for FI/MRI dual-modal targeted detection of pancreatic cancer", International Journal of Nanomedicine 2018:13, 2585-2599.

Li et al. (2009), "Inhibition of Micrometastatic Prostate Cancer Cell Spread in Animal Models By 213BilabeledMultipleTargeted A Radioimmunoconjugates", Clin Cancer Res 2009; 15(3), 865-875.

Journal of Japan Surgical Society, 2009, vol. 110 Emergency sales (2), p. 512 (HP—[069, 2006.01, 6]) (and its English language translation).

* cited by examiner

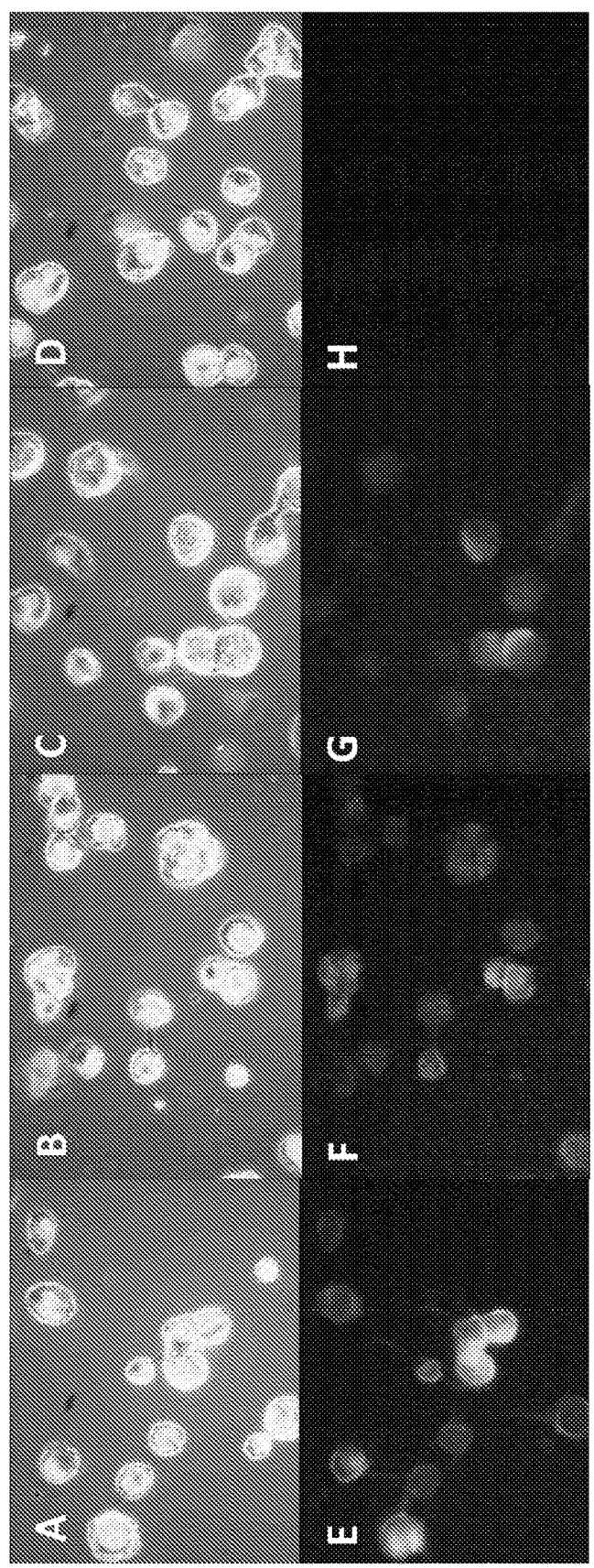
FIGURE ONE

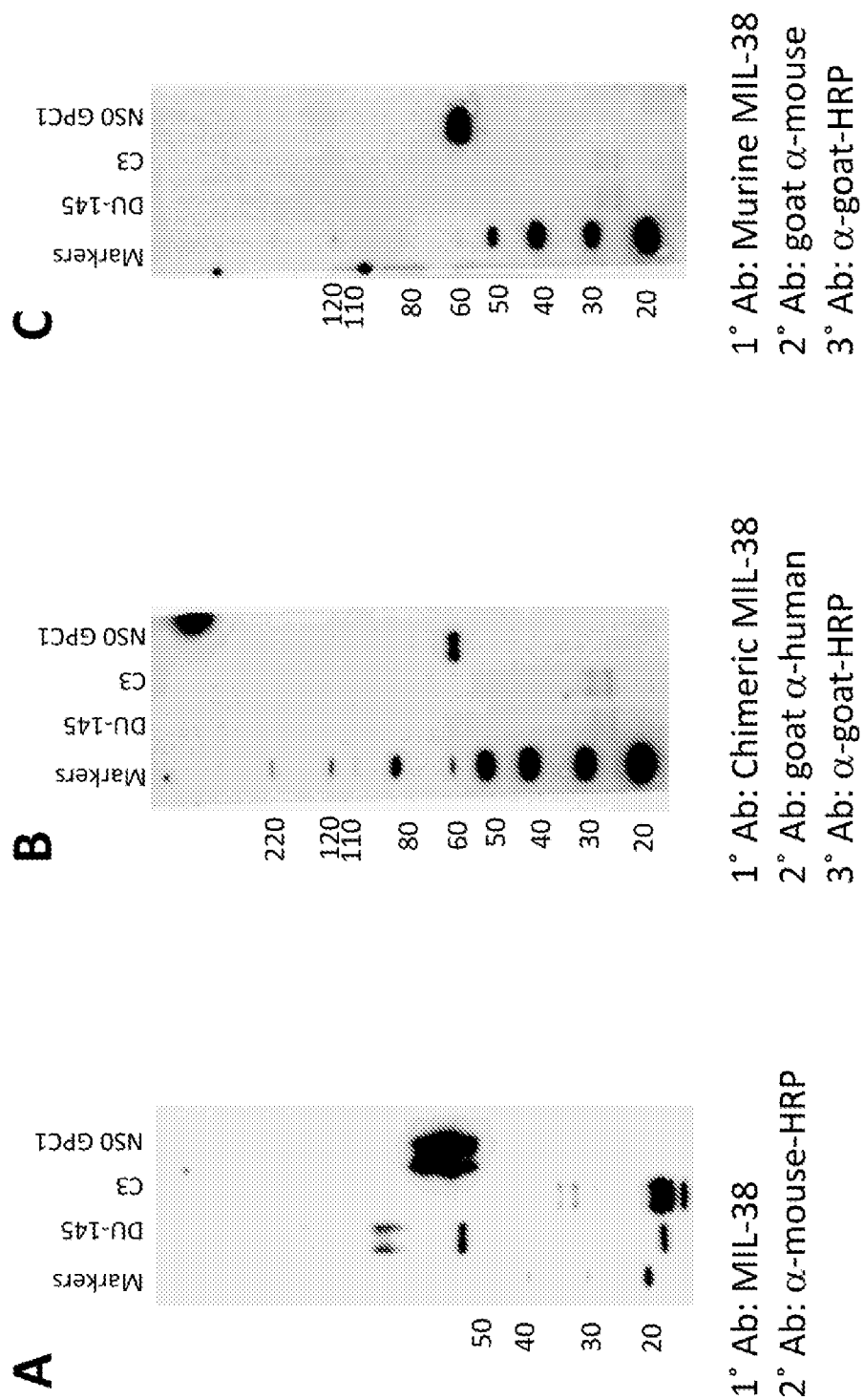
FIGURE TWO

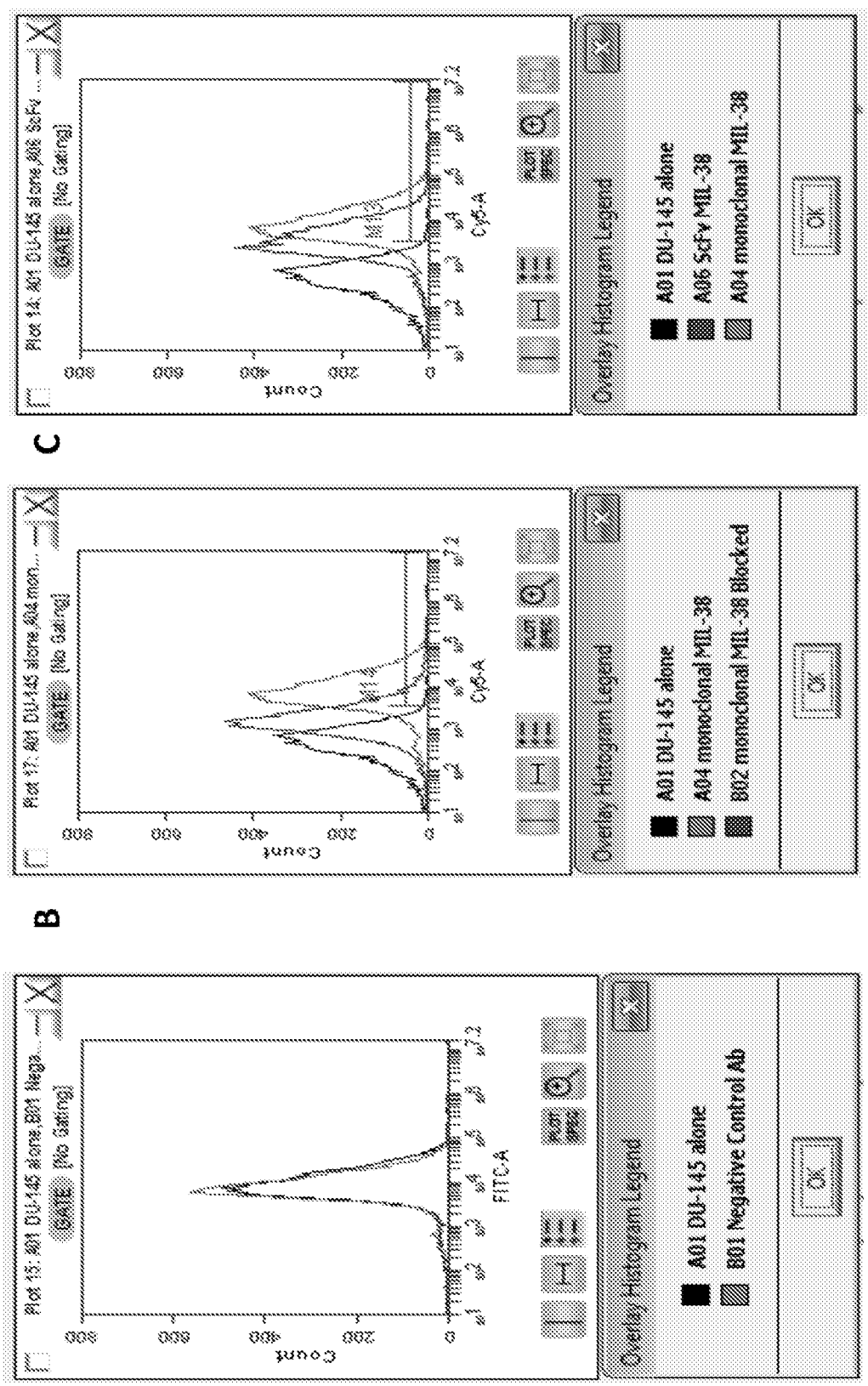
FIGURE THREE

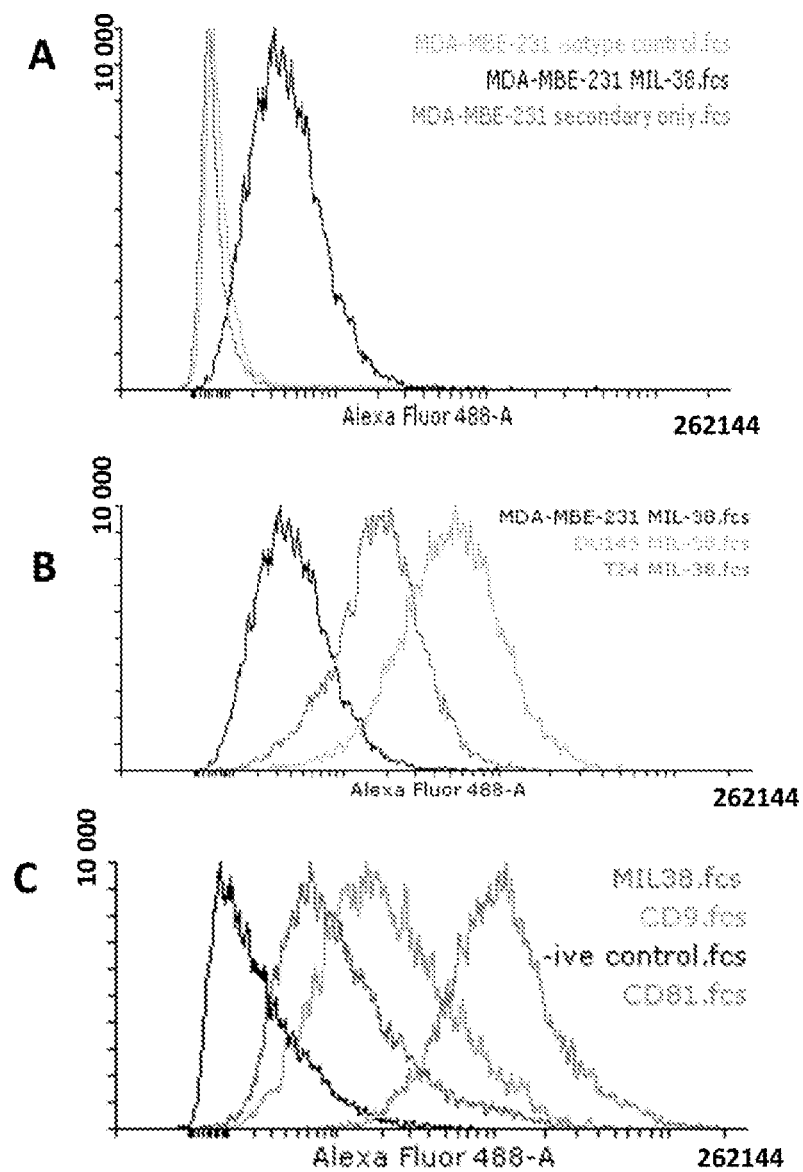
FIGURE FOUR

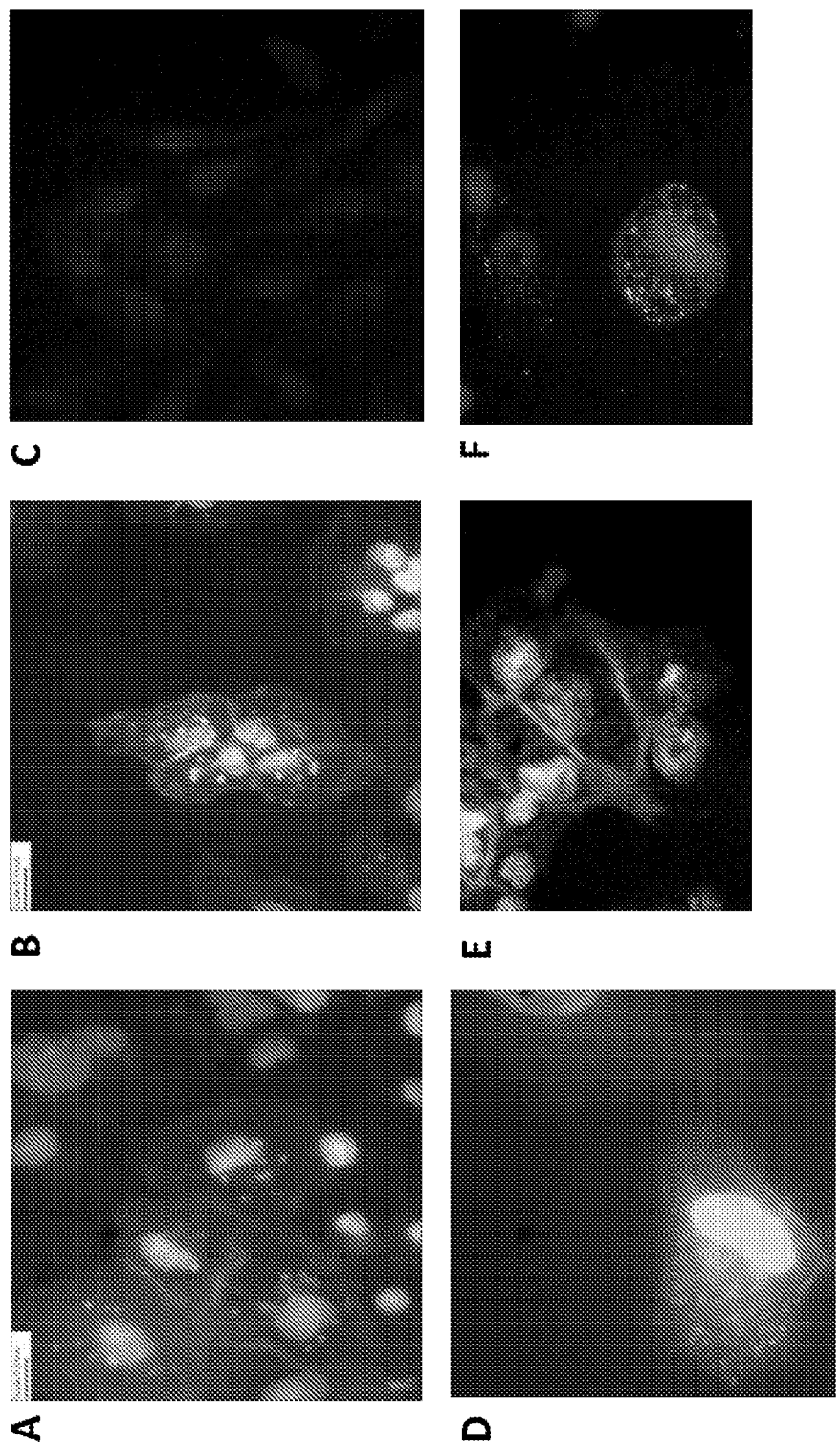
FIGURE FIVE

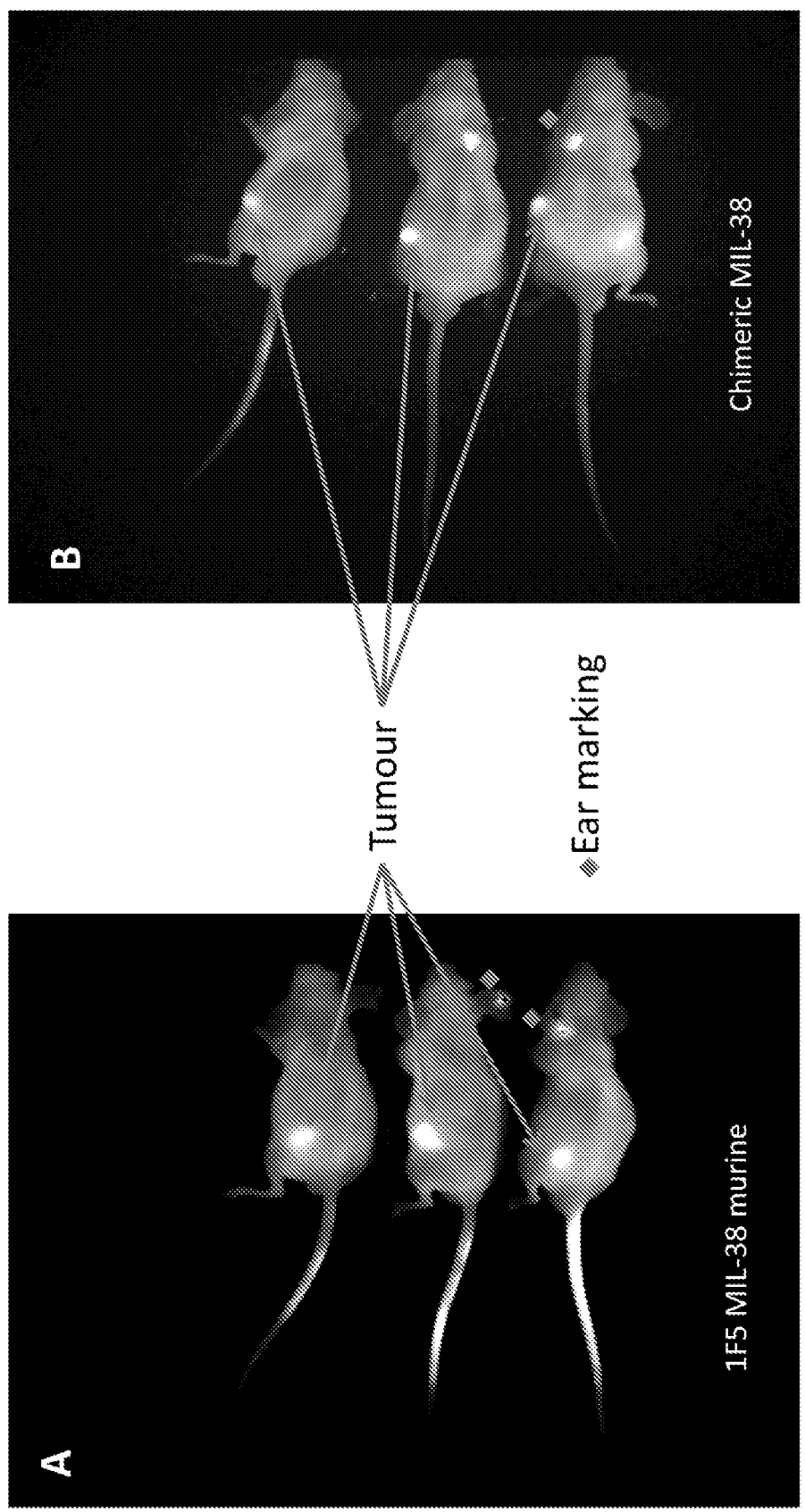
FIGURE SIX

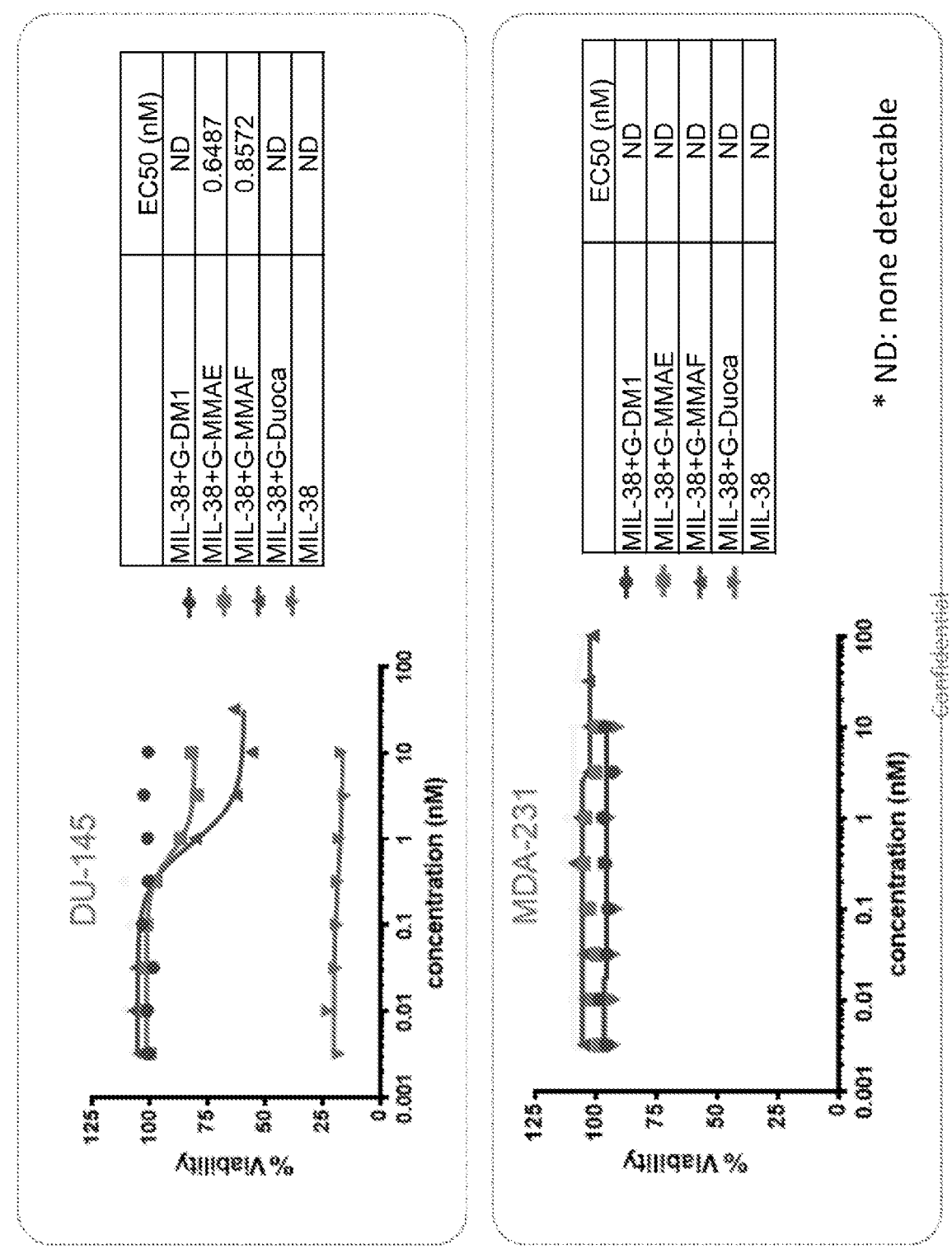
FIGURE SEVEN

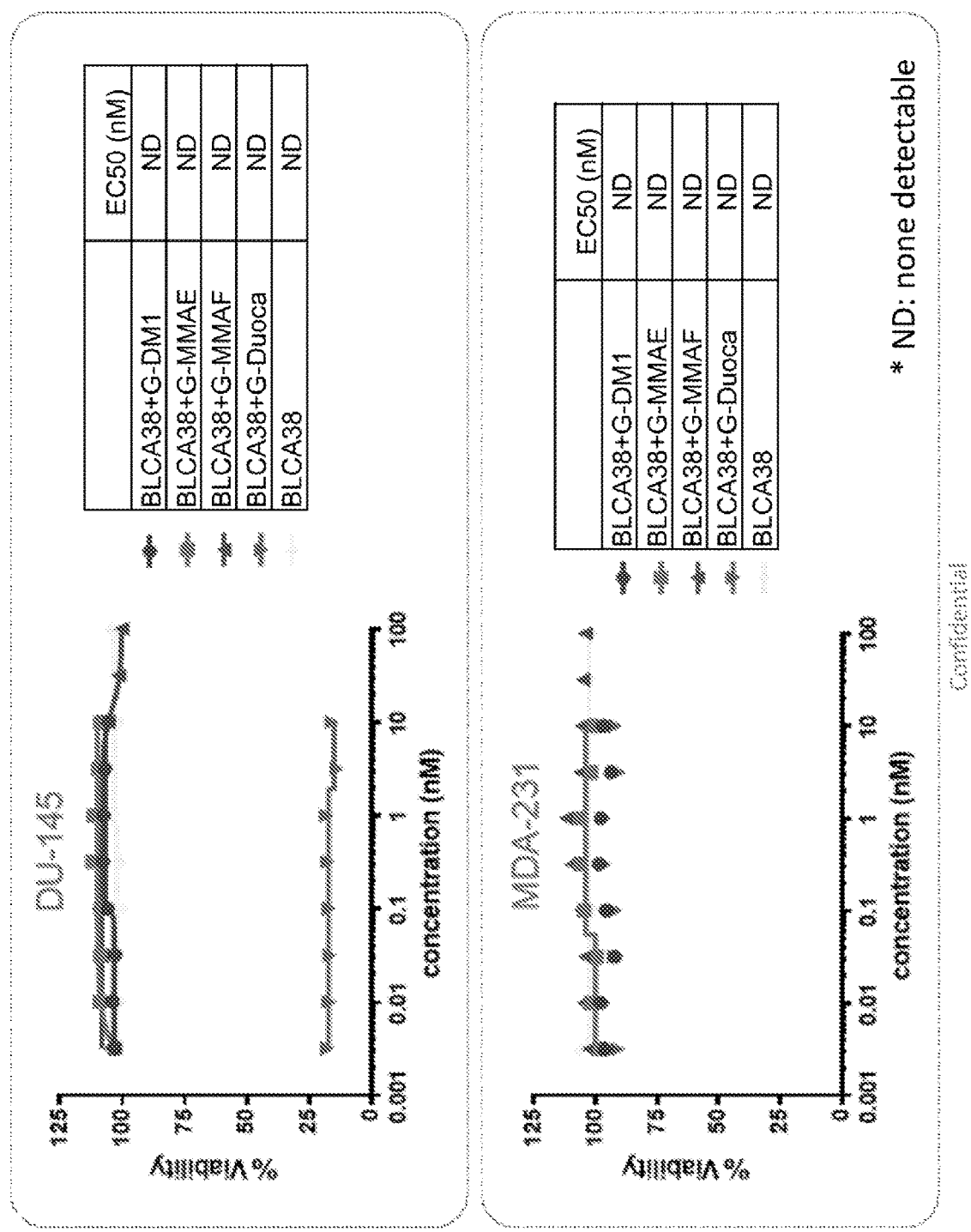
FIGURE SEVEN

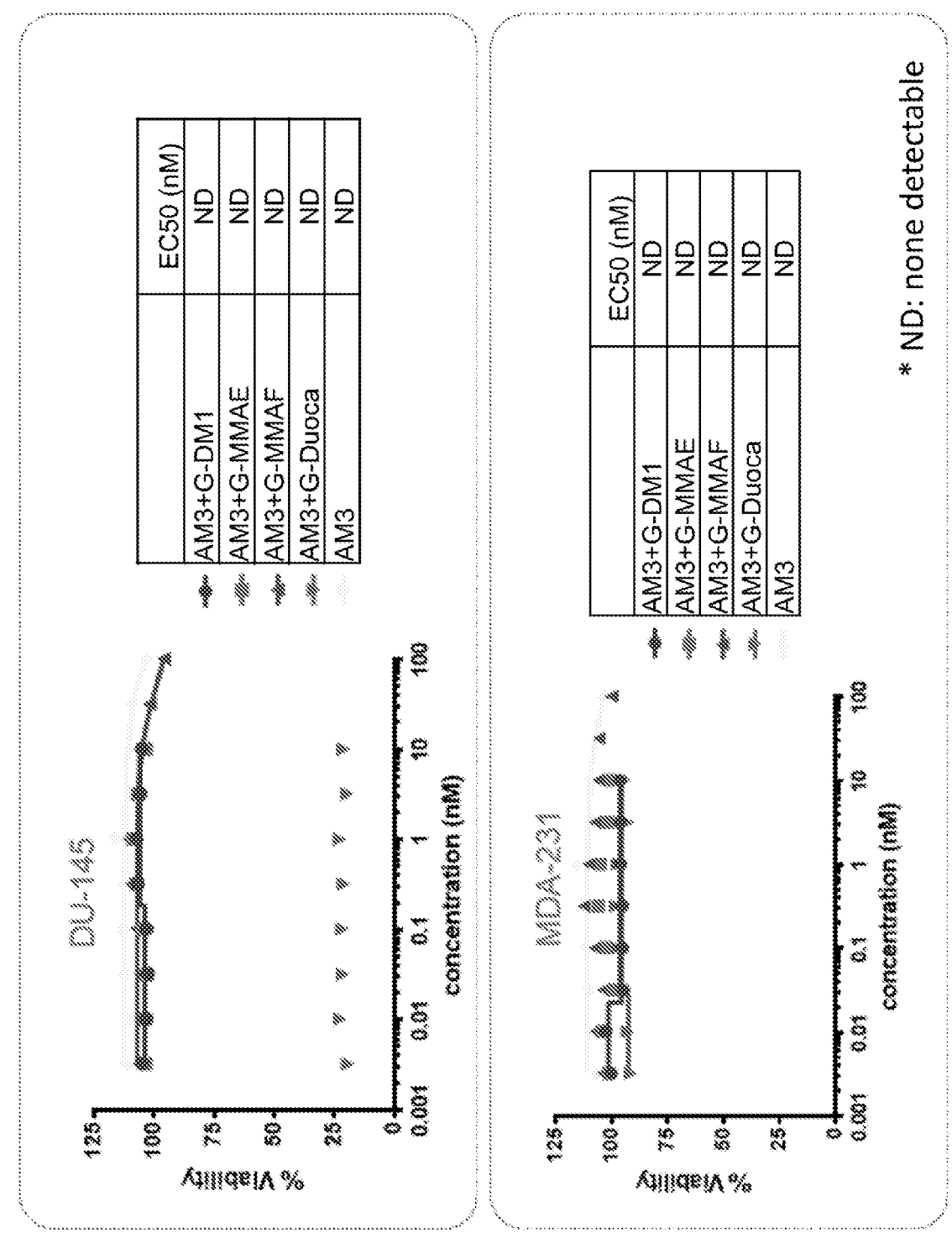
FIGURE SEVEN

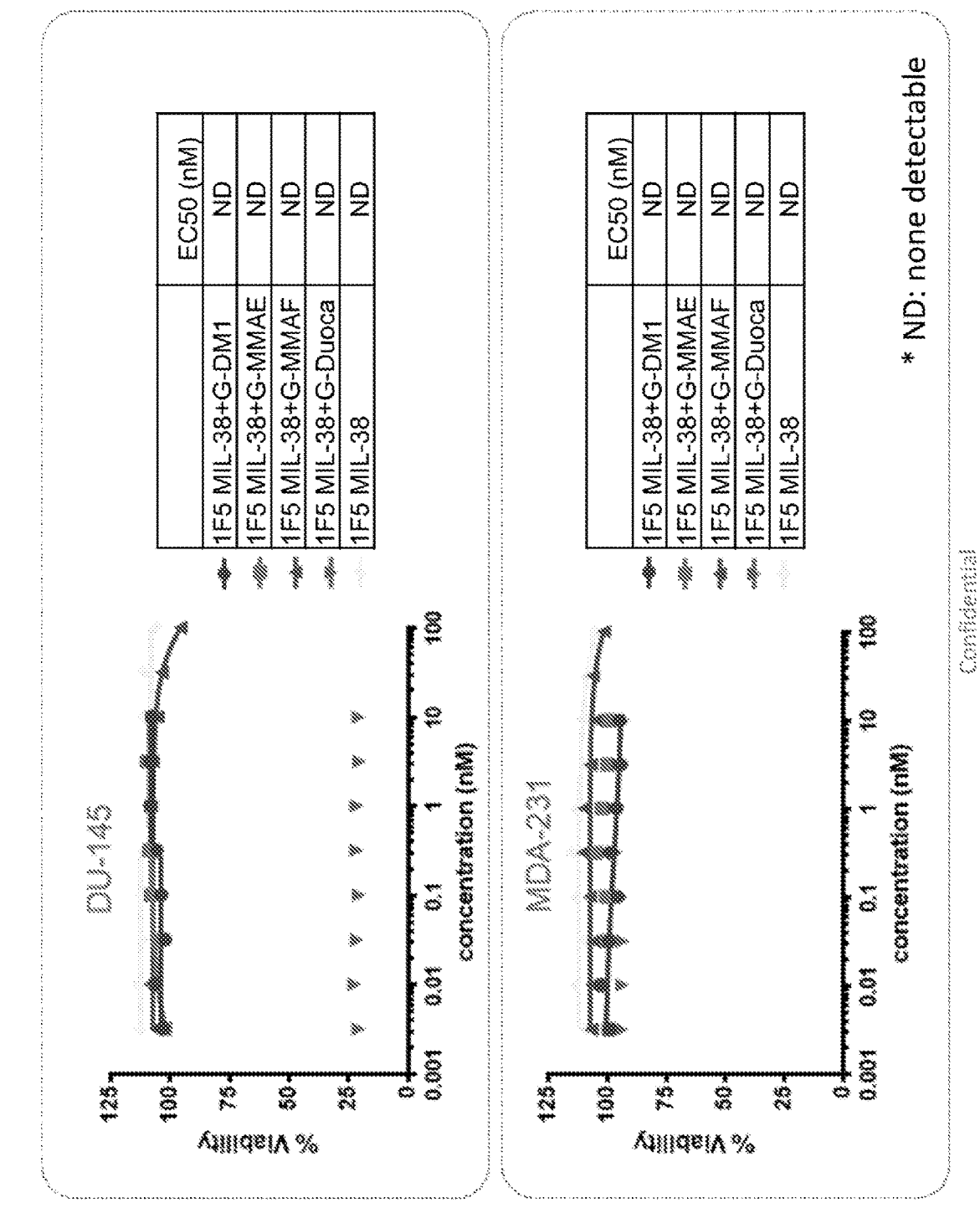
FIGURE SEVEN

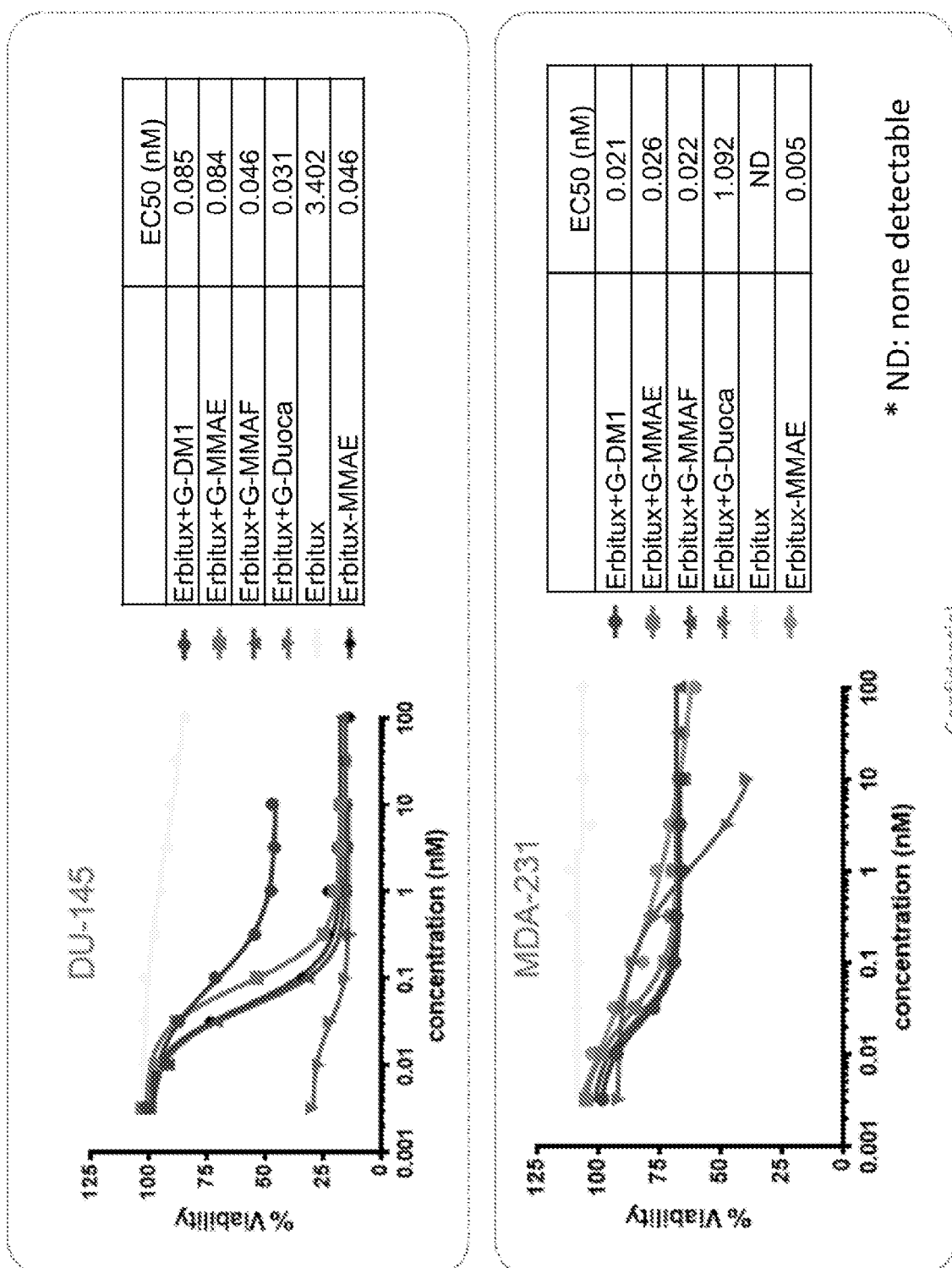
FIGURE SEVEN

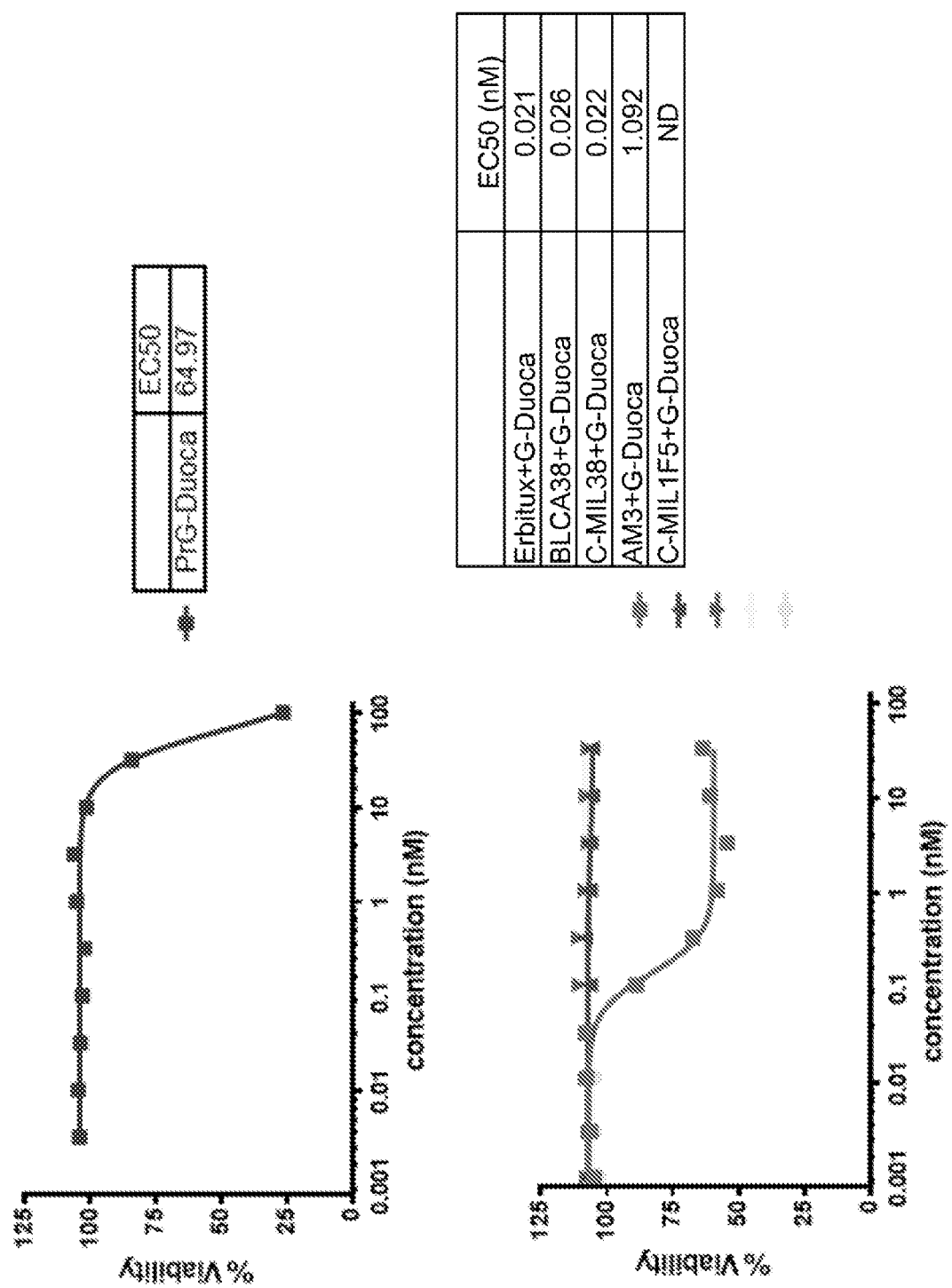
FIGURE SEVEN

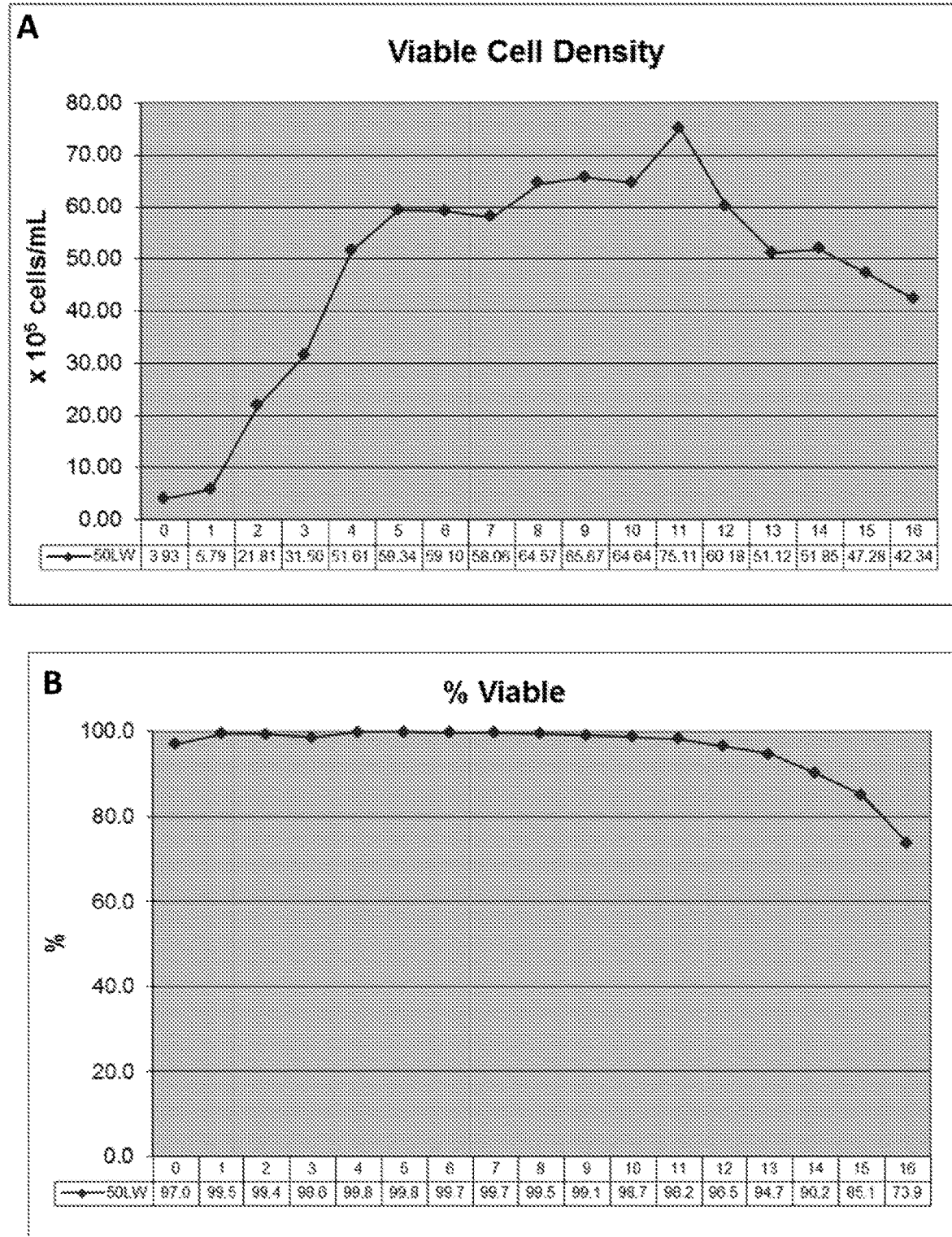
FIGURE EIGHT

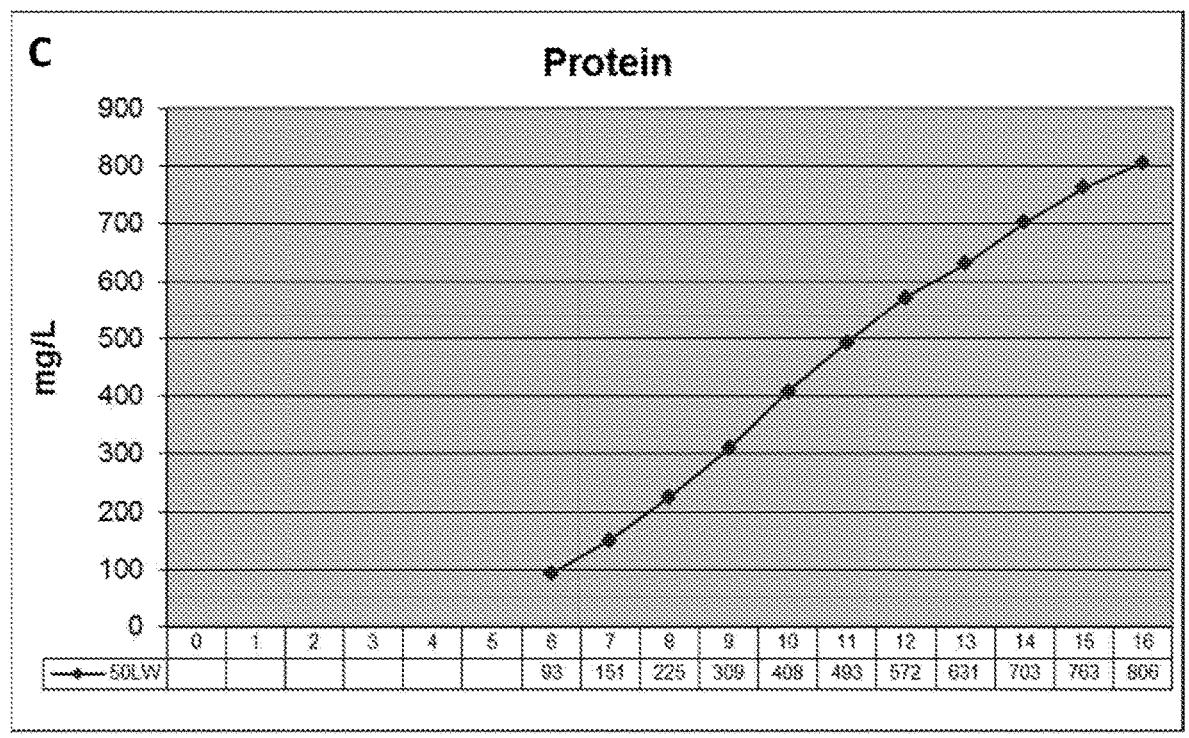
FIGURE EIGHT

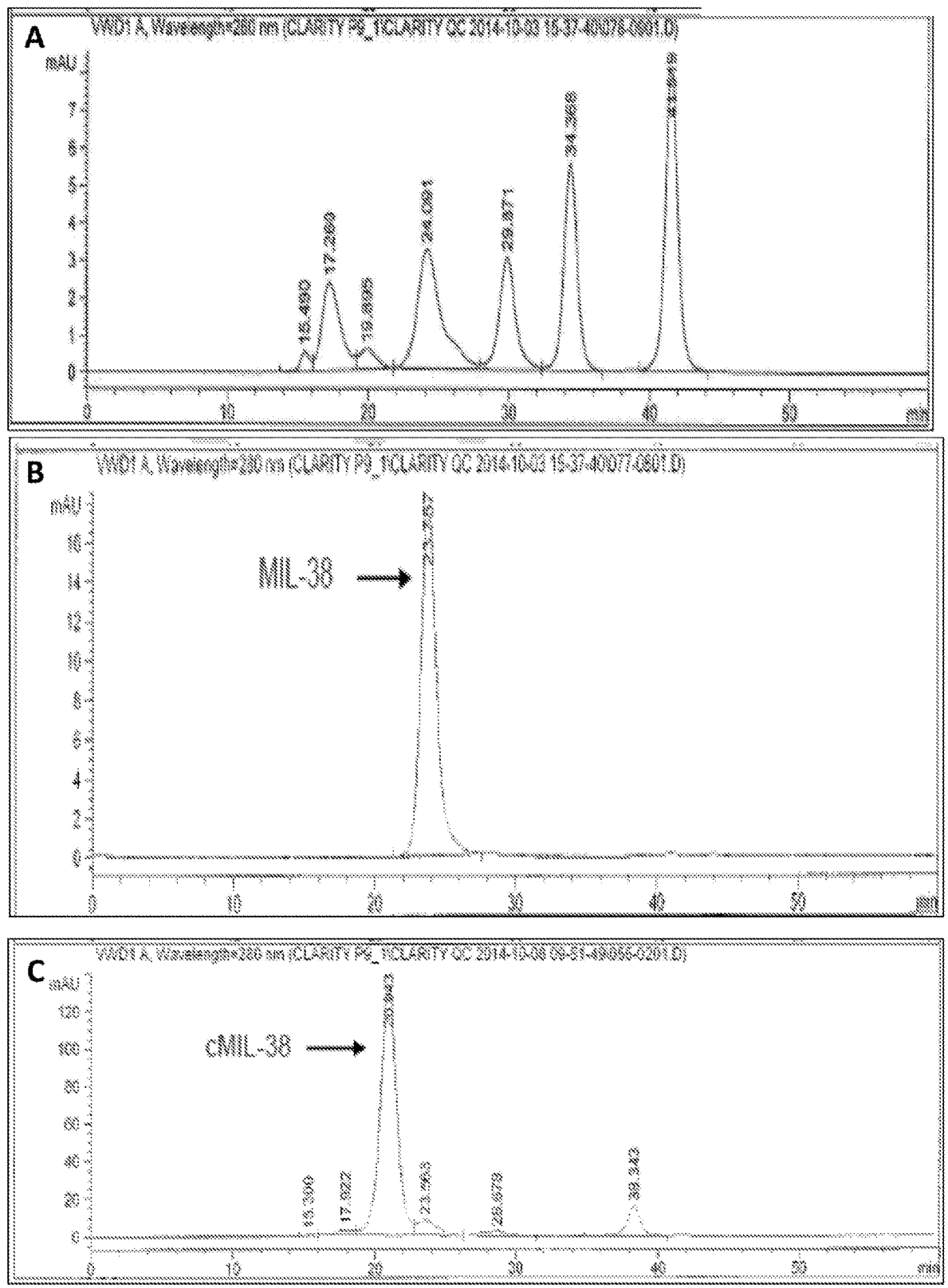
FIGURE NINE

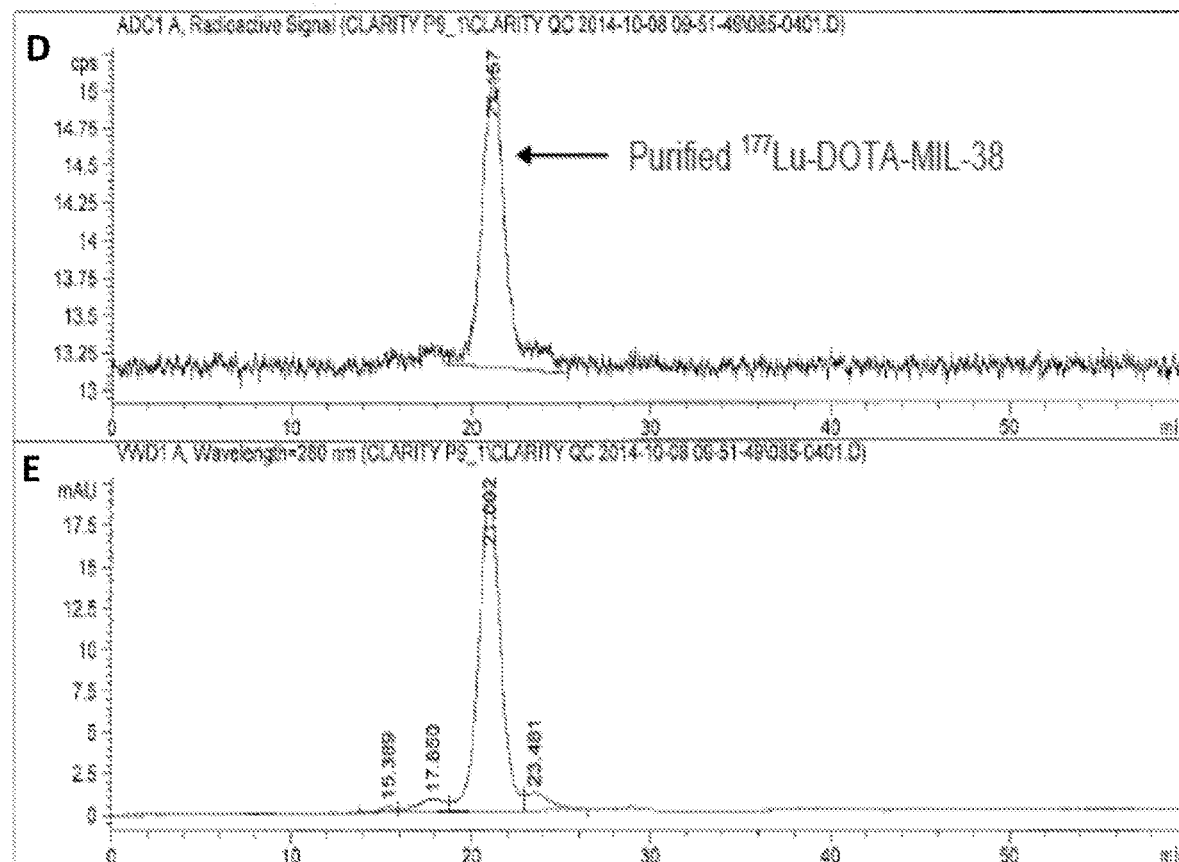
FIGURE NINE

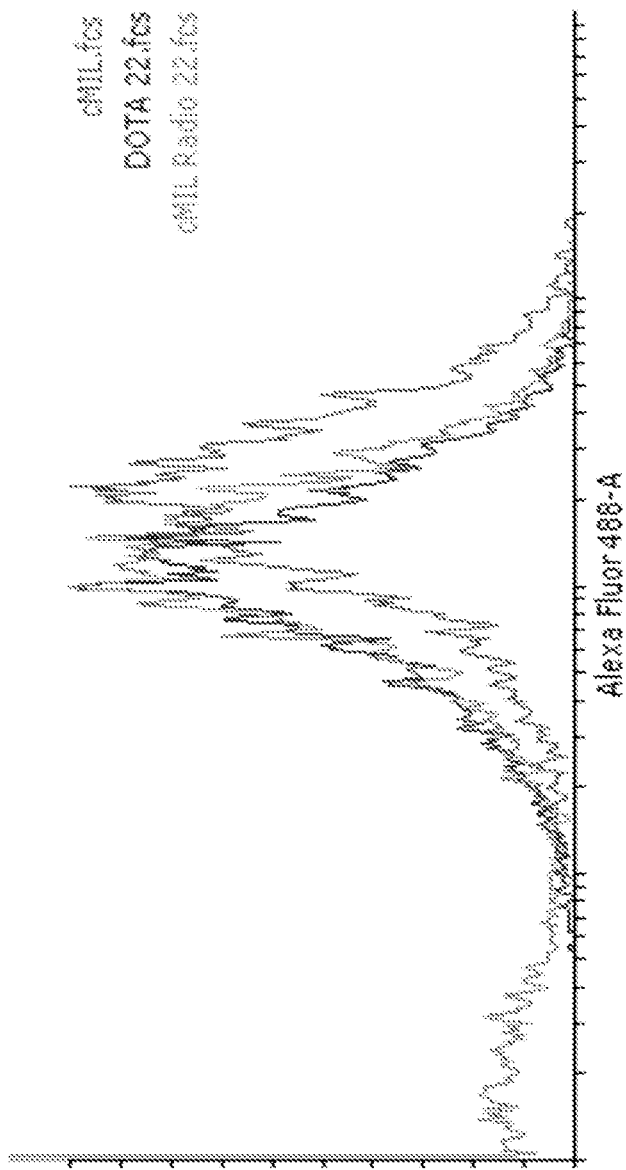
FIGURE TEN

A
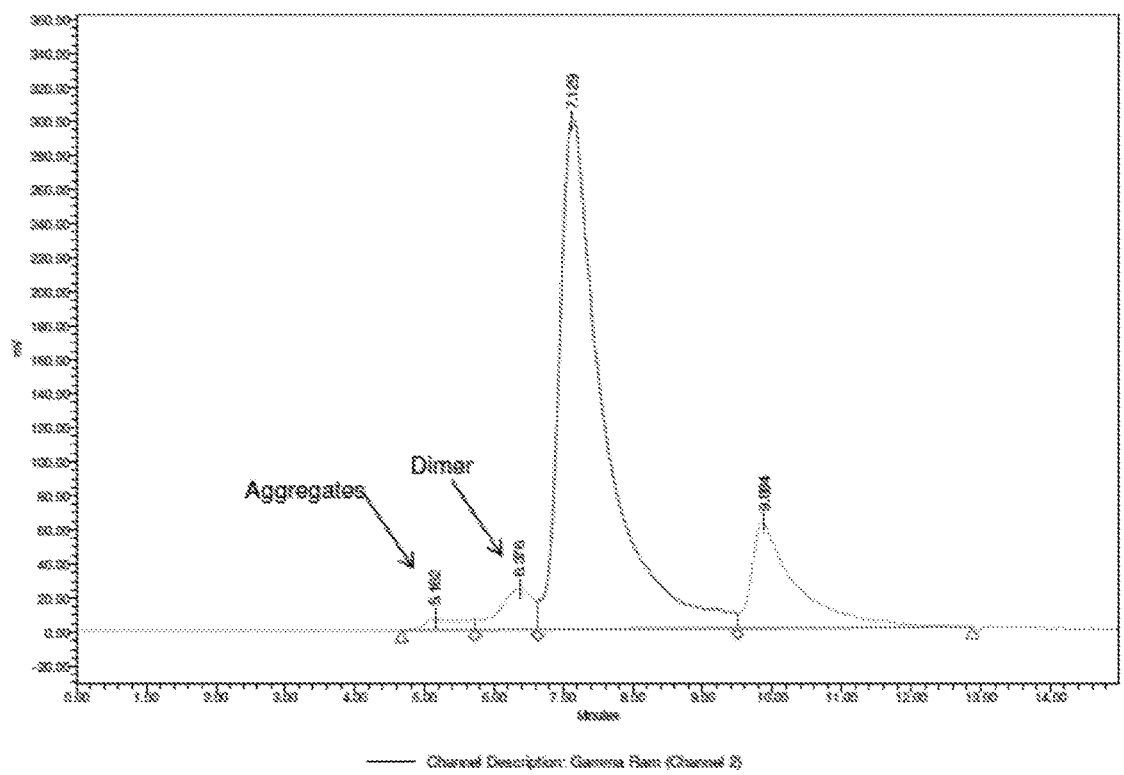
B
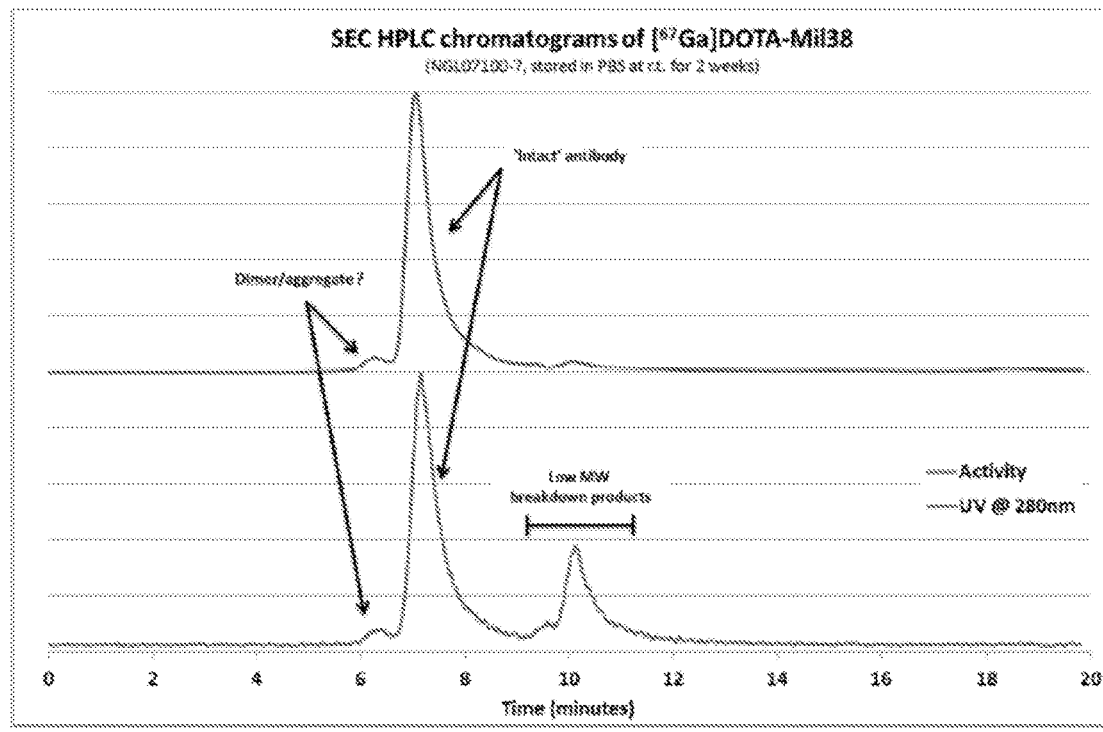
FIGURE ELEVEN

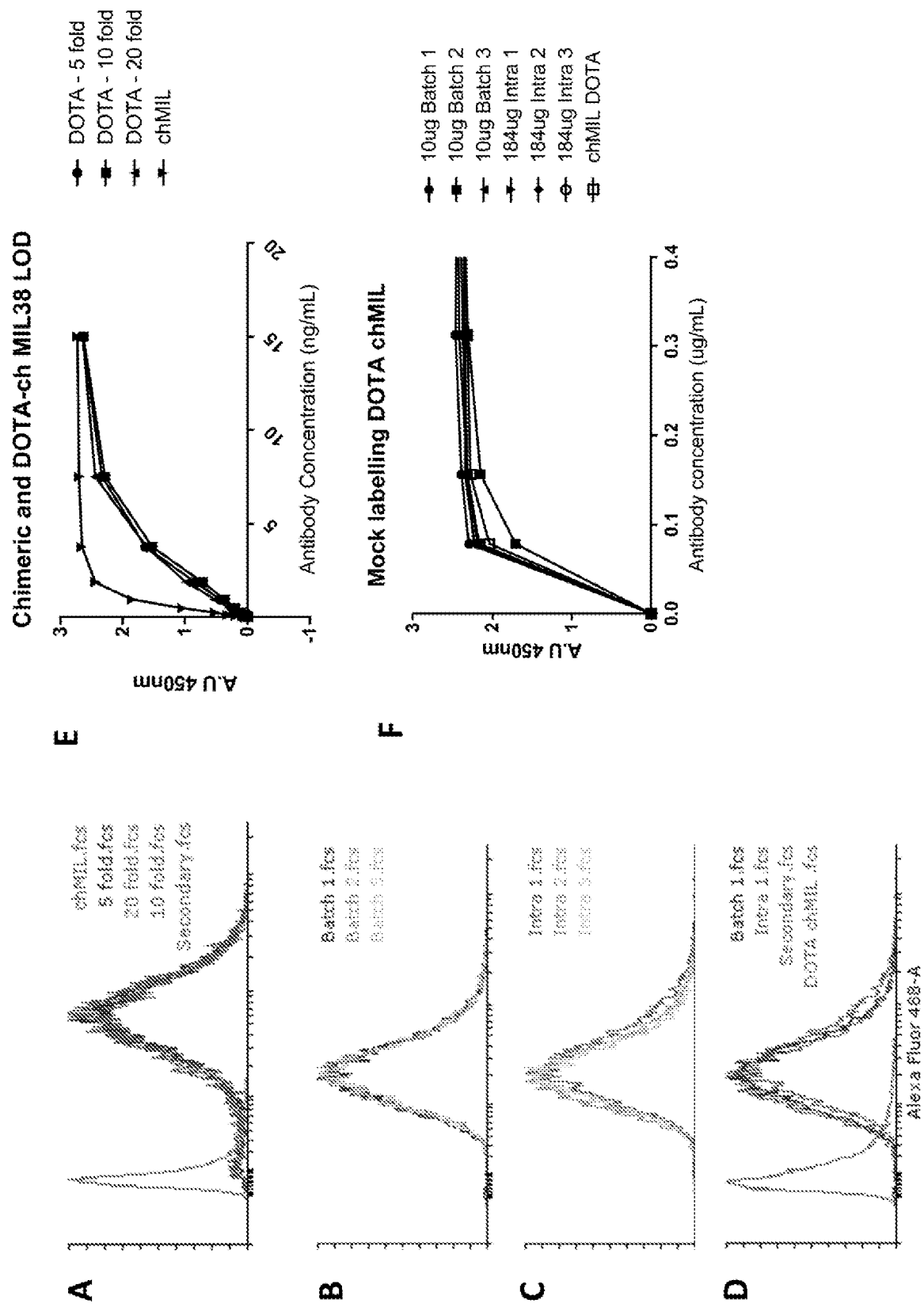
FIGURE TWELVE

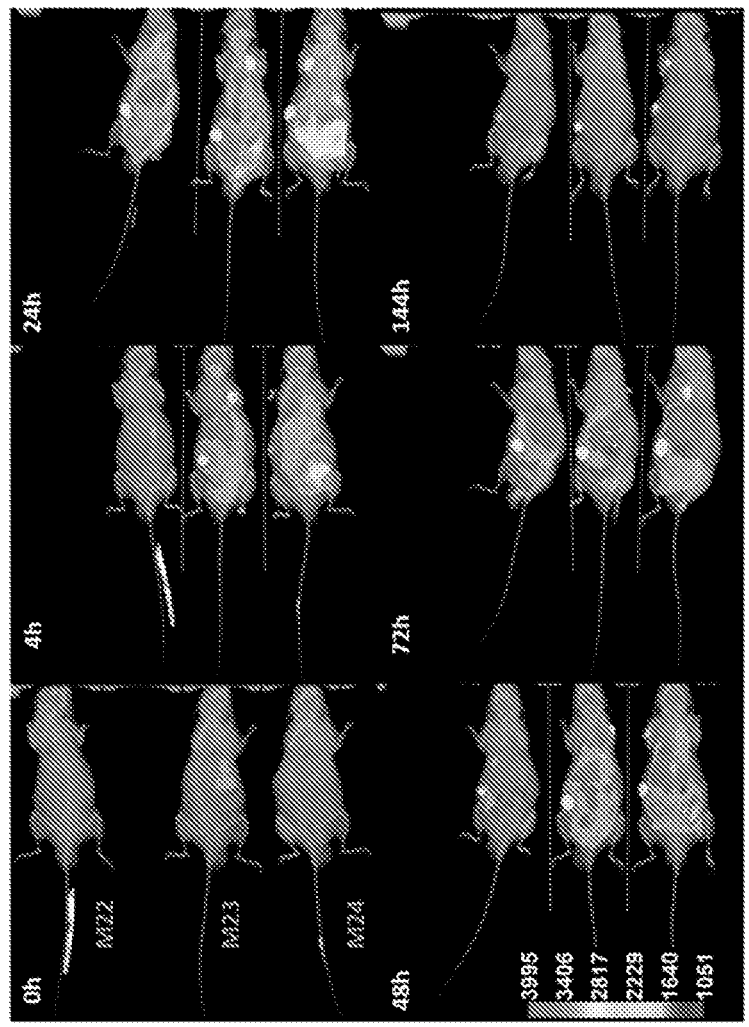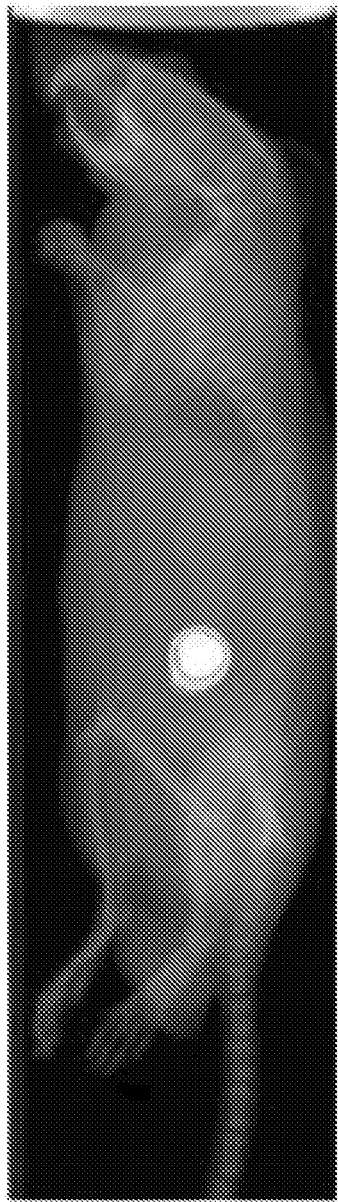
FIGURE THIRTEEN

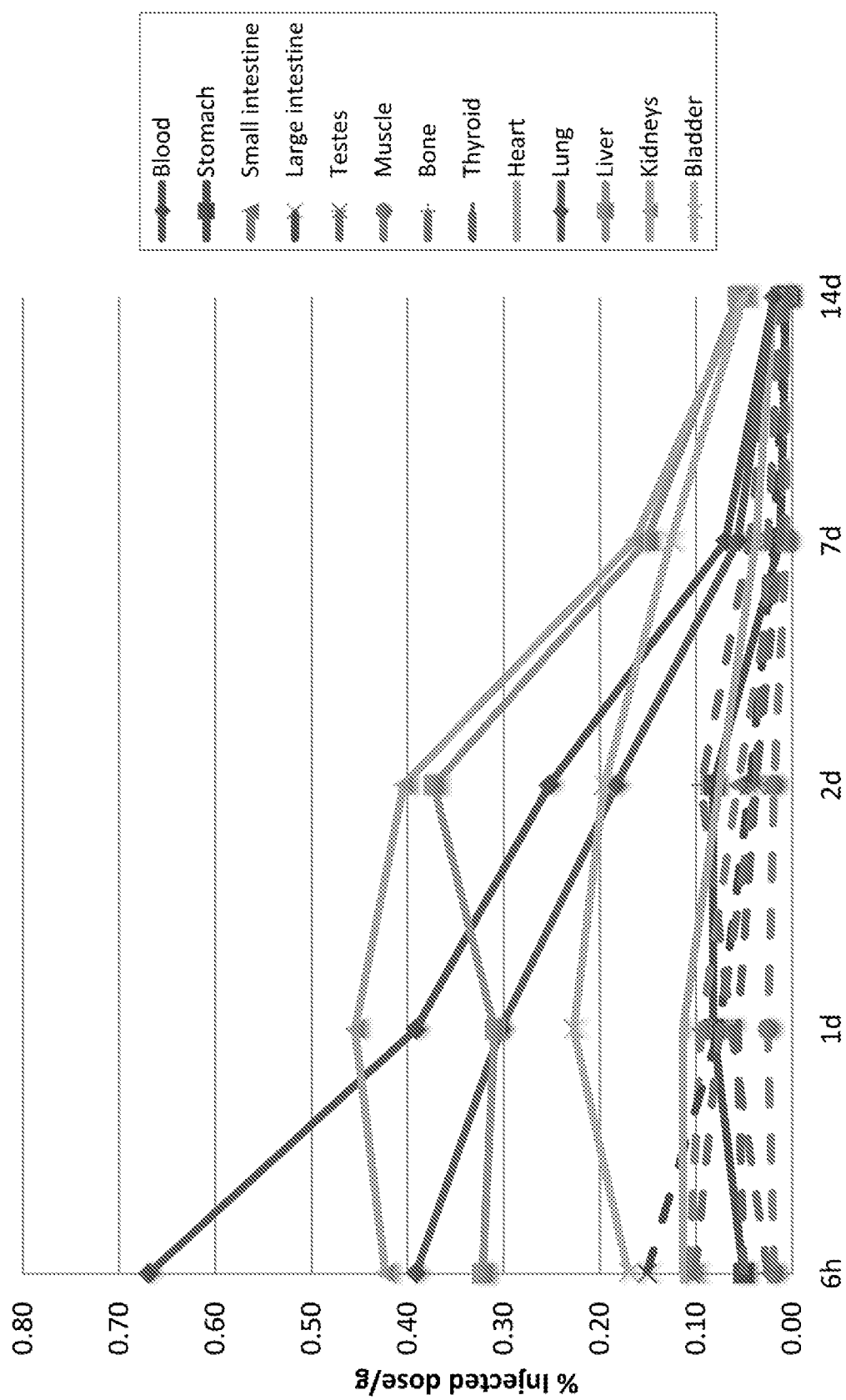
FIGURE FOURTEEN

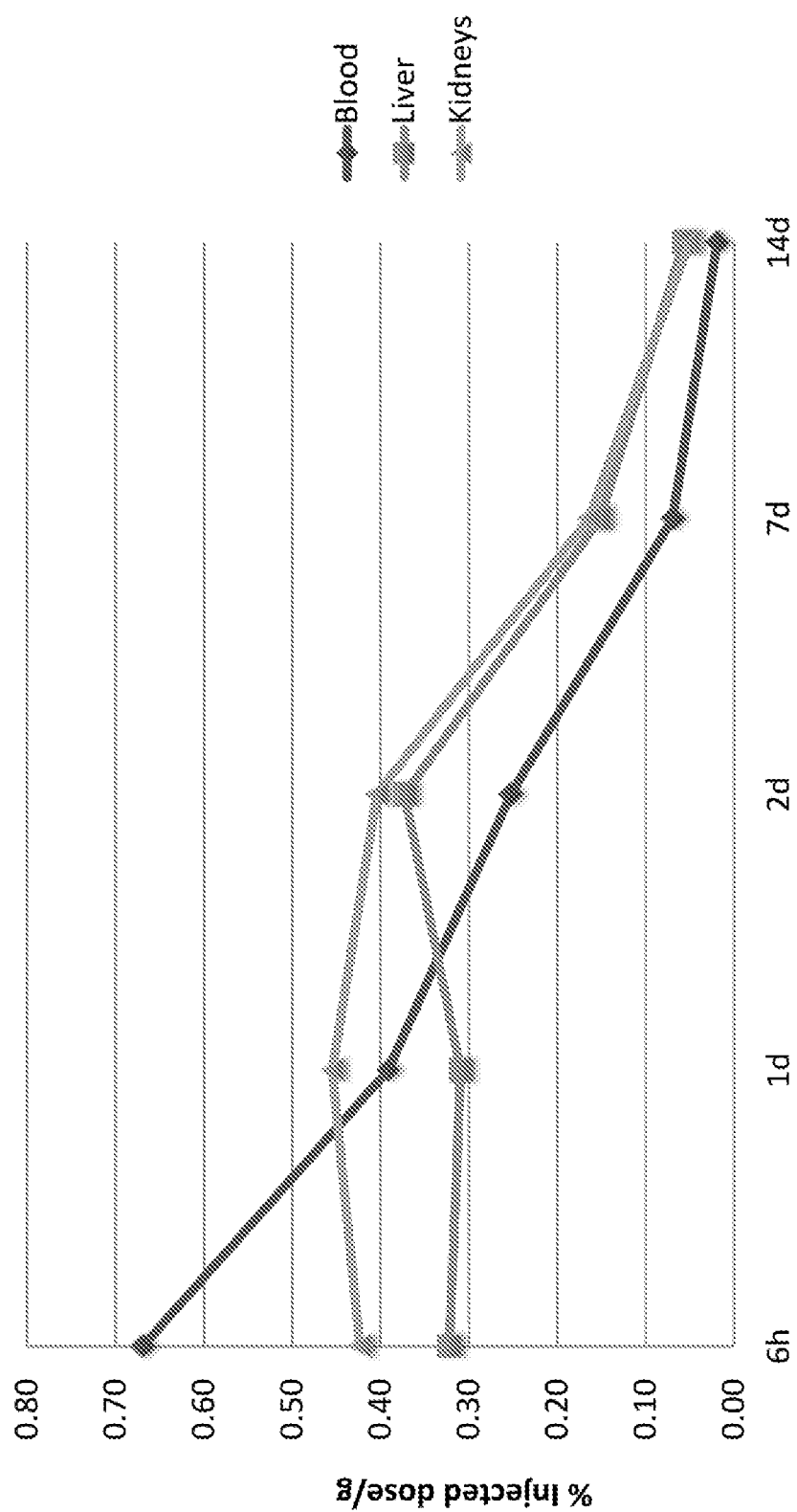
FIGURE FIFTEEN

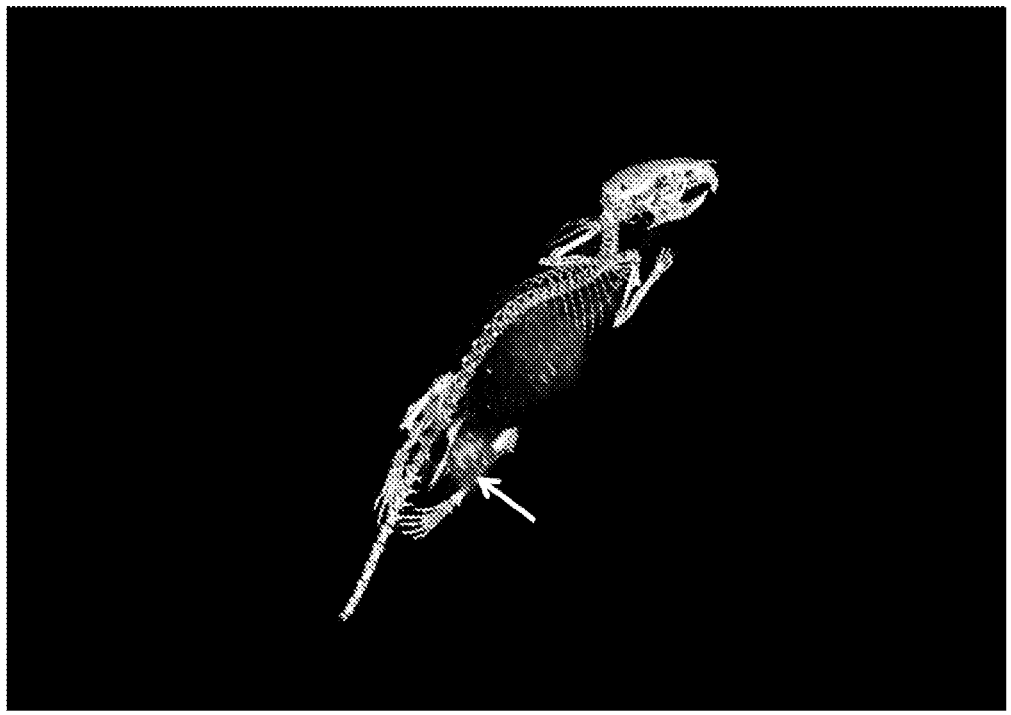
FIGURE SIXTEEN

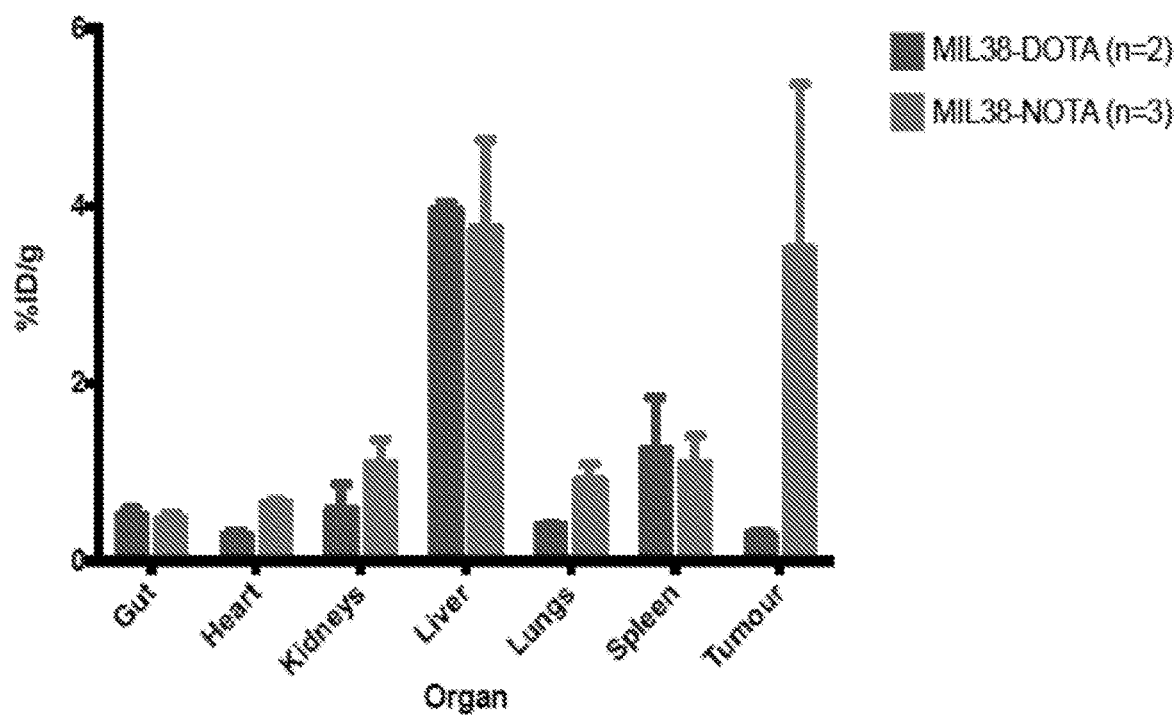
FIGURE SEVENTEEN

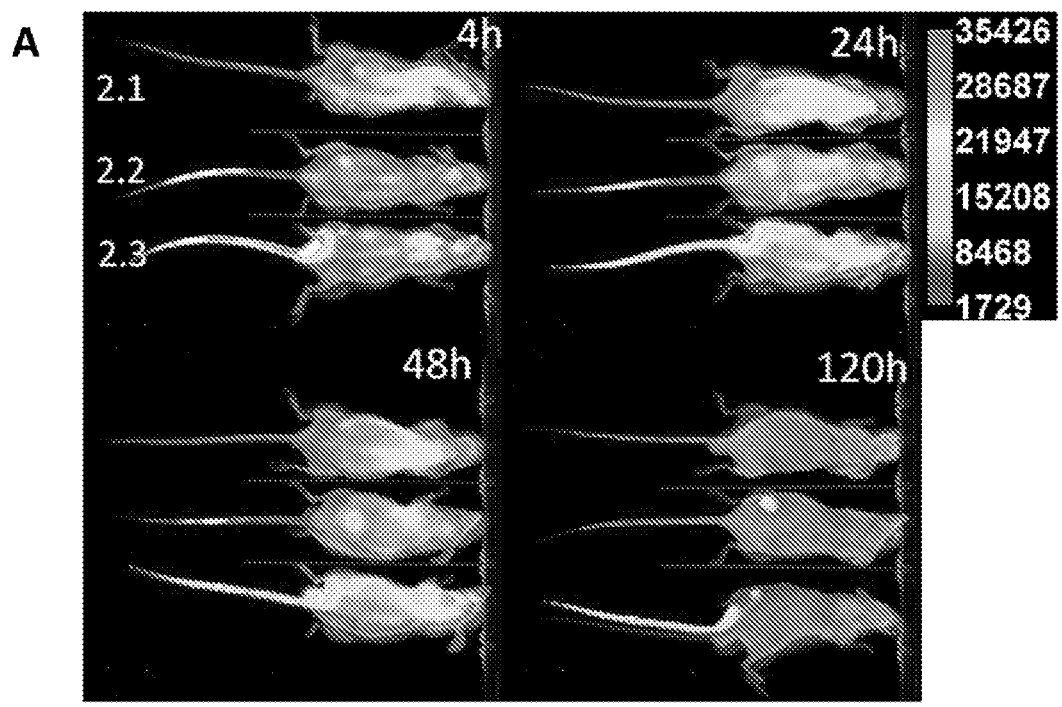
FIGURE EIGHTEEN

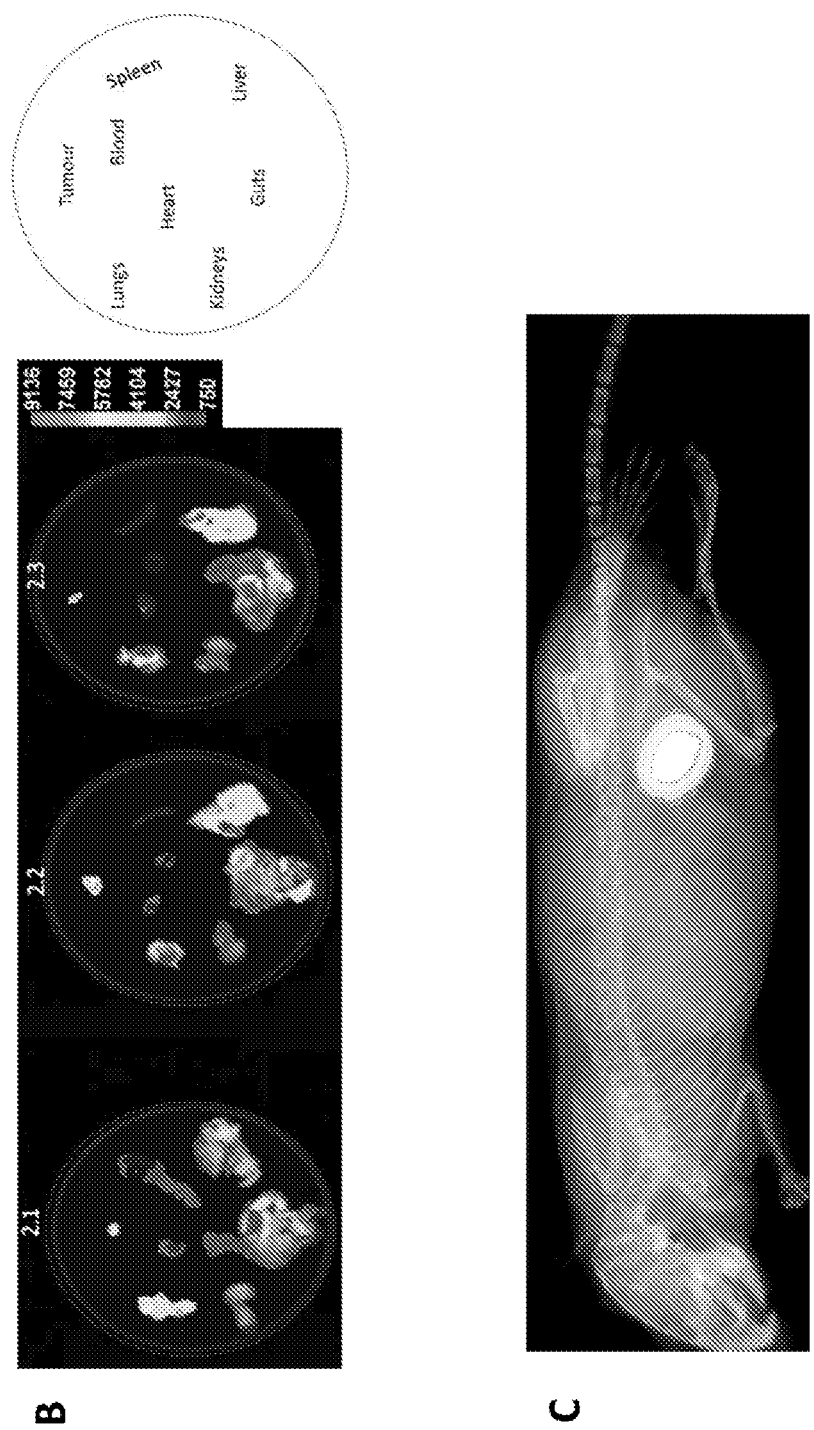
FIGURE EIGHTEEN

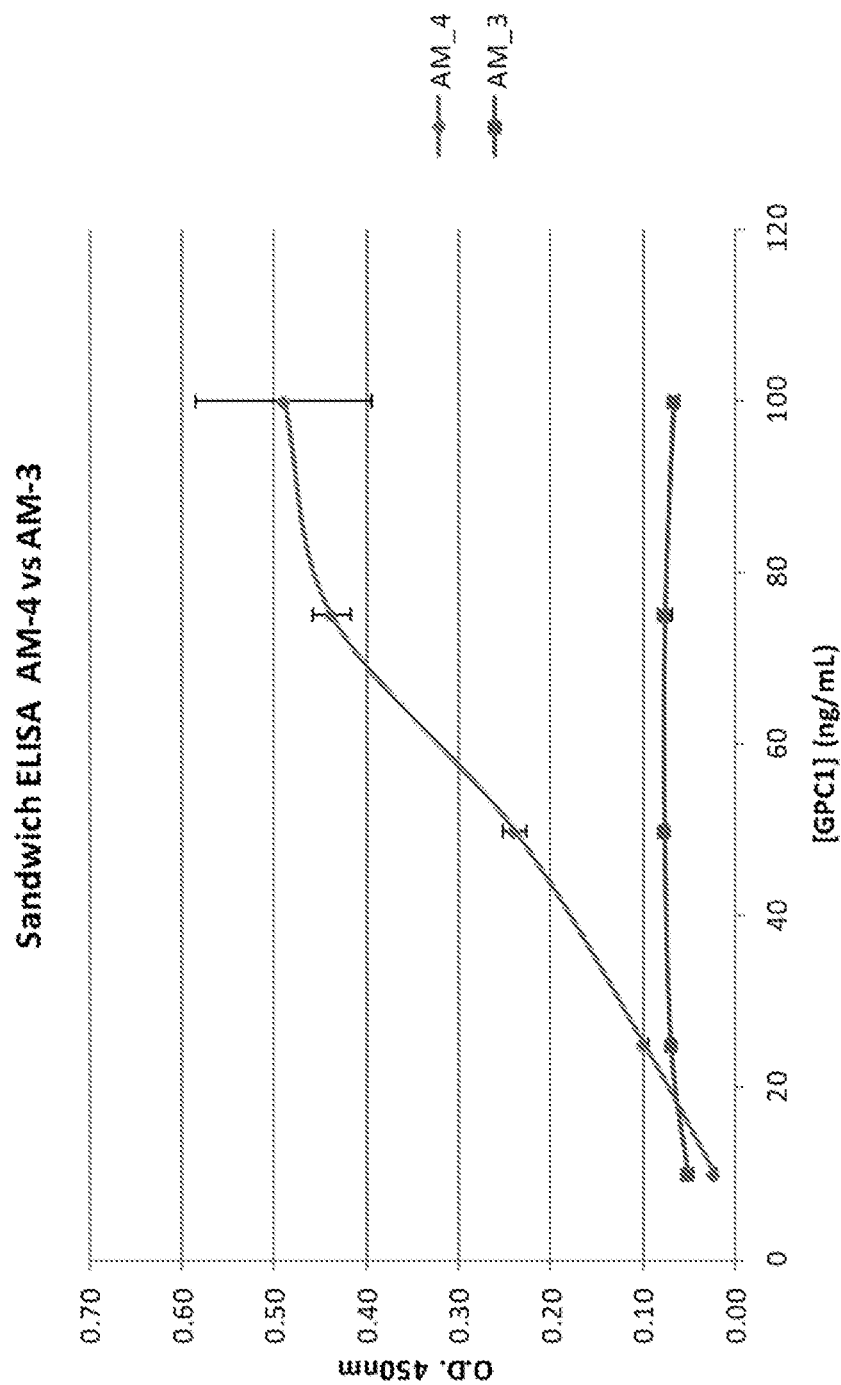
FIGURE NINETEEN

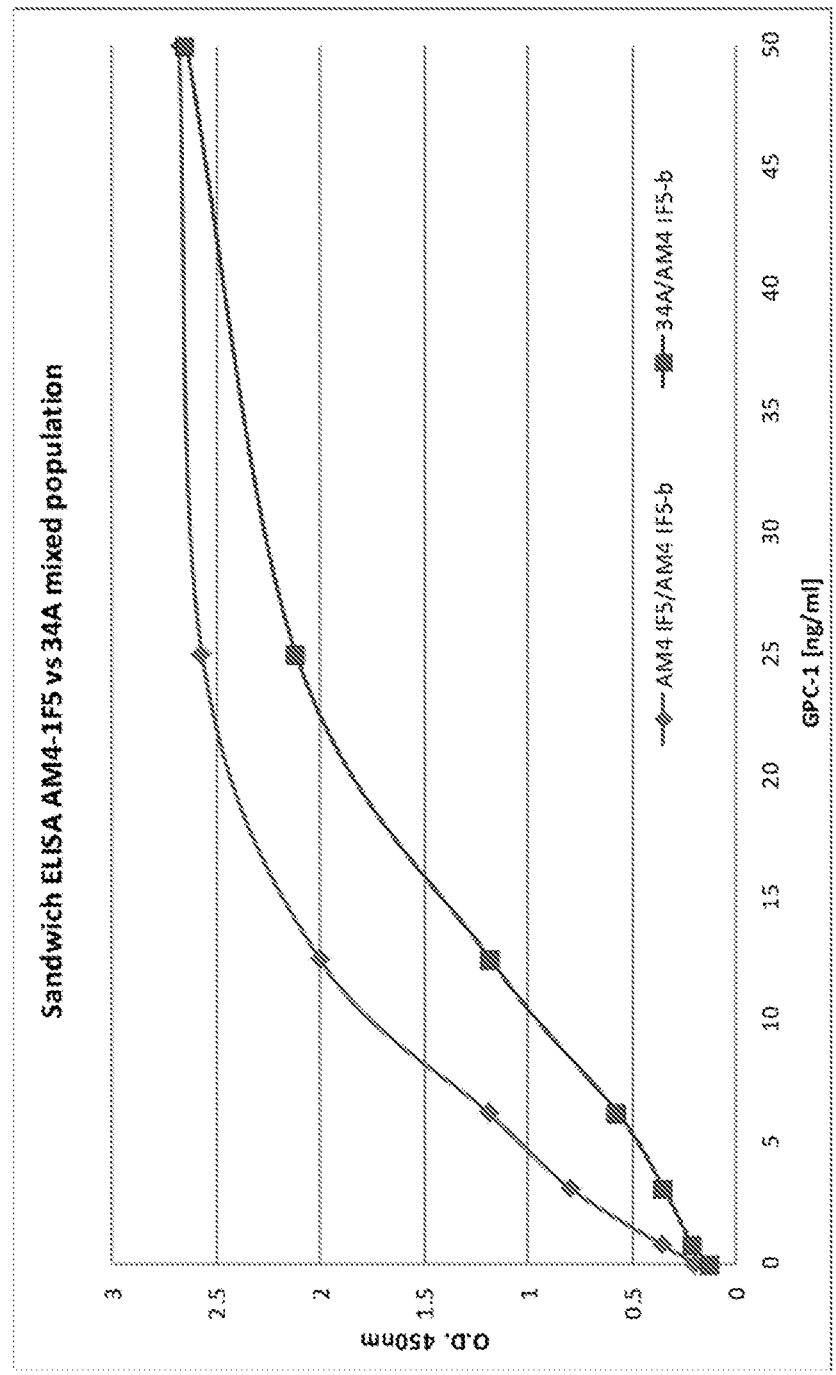
FIGURE NINETEEN

SEQUENCE LISTING

<160> NUMBER OF SEQ ID NOS: 11

<210> SEQ ID NO 1
<211> LENGTH: 1386
<212> TYPE: DNA
<213> ORGANISM: Mus musculus

<400> SEQUENCE: 1
atggcttggg tgtggaccttt gctattcctg atggctgctg cccaaagtat ccaagcacag     60
atccagttgg tgcagtctgg acctgagctg aagaagcctg gagagacagt caagatctcc    120

```
tgcaaggctt ctggttatgc cttcacagac tattcaatga actgggtgaa gcaggctcca    180
ggaaagggtt taaggtggat gggctggata aacactgaga ctggtgagcc aacatataca    240
gatgacttca agggacggtt tgccttctct ttggaaacct ctgccagcac tgccttttg    300 cagatcaaca acctcagaaa tgaagacacg gctacatatt tctgtgctag acactatgat    360 tacgggggt ttccttactg gggccaaggg actctggtca ctgtctctgc agccaaaacg    420 acaccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca gcgagaccgt cacctgcaac    660
gttgcccacc cggccagcag caccaaggtg gacaagaaaa ttgtgcccag ggattgtggt    720
tgtaagcctt gcatatgtac agtcccagaa gtatcatctg tcttcatctt ccccccaaag    780
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacgc aaccccggga ggagcagttc aacagcactt tccgctcagt cagtgaactt    960
cccatcatgc accaggactg gctcaatggc aaggagttca atgcagggt caacagtgca    1020 gctttccctg cccccatcga gaaaaccatc tccaaaacca aggcagacc gaaggctcca    1080 caggtgtaca ccattccacc tcccaaggag cagatggcca aggataaagt cagtctgacc    1140
tgcatgataa cagacttctt ccctgaagac attactgtgg agtggcagtg gaatgggcag    1200
ccagcggaga actacaagaa cactcagccc atcatggaca cagatggctc ttacttcgtc    1260
tacagcaagc tcaatgtgca gaagagcaac tgggaggcag gaaatacttt cacctgctct    1320
gtgttacatg agggcctgca caaccaccat actgagaaga gcctctccca ctctcctggt    1380
aaatga                                                              1386

<210> SEQ ID NO 2
<211> LENGTH: 705
<212> TYPE: DNA
<213> ORGANISM: Mus musculus

<400> SEQUENCE: 2
atgagtgtgc tcactcaggt cctggcgttg ctgctgctgt ggcttacagg tgccagatgt    60
gacatccaga tgactcagtc tccagcctcc ctatctgcat ctgtgggaga aactgtcacc    120
atcacatgtc gagcaagtgg gaatgttcac aattatttag catggtatca gcagaaacag    180
ggaaaatctc ctcaactcct ggtctatact gcaaaaacct agcagatgg tgtgccatca    240 aggttcagtg gcagtggatc aggaacacaa tattctctca agatcaatag cctgcagcct    300
gaagattttg ggacttatta ctgtcaacat ttttggagta tccgtggac gttcggtgga    360 ggcaccaagc tggaaatcaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag cacccctcacg    600 ttgaccaagg acgagtatga acgacataac agctatacct gtgaggccac tcacaagaca    660
tcaacttcac ccattgtcaa gagcttcaac aggaatgagt gttag                   705
```

-continued

```
<210> SEQ ID NO 3
<211> LENGTH: 461
<212> TYPE: PRT
<213> ORGANISM: Mus musculus

<400> SEQUENCE: 3

Met Ala Trp Val Trp Thr Leu Leu Phe Leu Met Ala Ala Gln Ser
 1               5                  10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ala Phe
        35                  40                  45

Thr Asp Tyr Ser Met Asn Trp Val Lys Gln Ala Pro Gly Lys Gly Leu
    50                  55                  60

Arg Trp Met Gly Trp Ile Asn Thr Glu Thr Gly Glu Pro Thr Tyr Thr
65                  70                  75                  80

Asp Asp Phe Lys Gly Arg Phe Ala Phe Ser Leu Glu Thr Ser Ala Ser
                85                  90                  95

Thr Ala Phe Leu Gln Ile Asn Asn Leu Arg Asn Glu Asp Thr Ala Thr
            100                 105                 110

Tyr Phe Cys Ala Arg His Tyr Asp Tyr Gly Gly Phe Pro Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
```

```
                370                 375                 380
Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
450                 455                 460

<210> SEQ ID NO 4
<211> LENGTH: 234
<212> TYPE: PRT
<213> ORGANISM: Mus musculus

<400> SEQUENCE: 4

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Val His Asn Tyr Leu Ala Trp Tyr Gln Gln Lys Gln Gly Lys Ser Pro
    50                  55                  60

Gln Leu Leu Val Tyr Thr Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Asn Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 5
<211> LENGTH: 1404
<212> TYPE: DNA
<213> ORGANISM: Artificial Sequence
<220> FEATURE:
<223> OTHER INFORMATION: Mus musculus/Homo-sapiens chimeric sequence

<400> SEQUENCE: 5
```

```
atggcttggg tgtggacact gctgttcctg atggctgctg cccagagtat tcaggctcag    60
attcagctgg tccagagcgg tcccgagctg aagaagccag gcgagaccgt gaagatctcc   120
tgcaaggcca gcggctacgc tttcacagac tattctatga actgggtgaa gcaggcccca   180
ggcaagggcc tgaggtggat gggctggatc aataccgaga caggcgagcc cacctacaca   240
gacgatttca agggccggtt cgctttttcc ctggagacct ctgcctccac agcttttctg   300
cagatcaaca atctgagaaa cgaggacacc gccacatact ctgcgctag gcactacgat    360 tatggcggct ttccttattg gggccagggc accctggtga cagtgtccag cgcctctacc   420
aagggcccat ccgtgtttcc actggctccc tcttccaaga gcacctctgg cggcacagcc   480
gctctgggct gtctggtgaa ggattacttc ccagagcccg tgacagtgtc ttggaactcc   540
ggcgccctga cctccggagt gcatacattt cccgctgtgc tgcagagctc tggcctgtac   600
agcctgtcca gcgtggtgac cgtgccttct ccagcctggg cacccagac atatatctgc    660 aacgtgaatc acaagccatc aatacaaag gtggacaaga aggtggagcc caagagctgt    720
gataagaccc atacatgccc cccttgtcct gctccagagc tgctgggagg acctagcgtg   780
ttcctgtttc cacccaagcc taaggacacc ctgatgatct ctaggacccc cgaggtgaca   840
tgcgtggtgg tggacgtgtc ccacgaggat cctgaggtga agttcaactg gtacgtggat   900
ggcgtggagg tgcataatgc taagaccaag cctaggagg agcagtacaa cagcacctat    960
cgggtggtgt ctgtgctgac agtgctgcac caggactggc tgaacggcaa ggagtataag  1020
tgcaaggtga gcaataaggc cctgcccgct cctatcgaga agaccatctc taaggccaag  1080
ggccagcctc gggagccaca ggtgtacaca ctgcctccaa gcagagacga gctgaccaag  1140
aaccaggtgt ctctgacatg tctggtgaag ggcttctatc cttctgatat cgctgtggag  1200
tgggagtcca atggccagcc agagaacaat tacaagacca caccccctgt gctggacagc  1260
gatggctctt tctttctgta ttccaagctg accgtggata gagcaggtg gcagcagggc   1320 aacgtgttct cctgtagcgt gatgcacgag gcactgcaca ccactacac tcagaaatcc   1380 ctgtccctgt cacctggcaa atga                                         1404
```

<210> SEQ ID NO 6
<211> LENGTH: 705
<212> TYPE: DNA
<213> ORGANISM: Artificial Sequence
<220> FEATURE:
<223> OTHER INFORMATION: Mus musculus/Homo sapiens chimeric sequence

<400> SEQUENCE: 6

```
atgagcgtgc tgacccaggt gctggccctg ctgctgctgt ggctgaccgg agcccgttgc    60
gacatccaga tgacccagtc ccctgcctct ctgtccgcca gcgtgggcga gaccgtgaca   120
atcacctgca gagcctctgg caacgtgcac aattacctgg cttggtatca gcagaagcag   180
ggcaagtccc cacagctgct ggtgtacaca gccaagaccc tggctgacgg cgtgcccagc   240
aggttctctg gctccggcag cggcacacag tatagcctga agatcaactc tctgcagcct   300
gaggattttg gcacctacta ttgccagcat ttctggtcta atccatggac atttggcggc   360
ggcaccaagc tggagatcaa aggacagtg ccgctccct ccgtgttcat ctttccccct    420
agcgacgagc agctgaagtc tggcaccgct tccgtggtgt gcctgctgaa caatttctac   480
cctcgggagg ccaaggtgca gtggaaggtg gataacgctc tgcagtctgg caattcccag   540
gagagcgtga cagagcagga ctctaaggat tccacctata gcctgtccag cacactgacc   600
```

-continued

```
ctgtccaagg ccgactacga gaagcacaag gtgtatgctt gtgaggtcac tcaccagggg    660
ctgtcaagtc cagtcacaaa gtccttcaat aggggggaat gctga                   705
```

```
<210> SEQ ID NO 7
<211> LENGTH: 467
<212> TYPE: PRT
<213> ORGANISM: Artificial Sequence
<220> FEATURE:
<223> OTHER INFORMATION: Mus musculus/Homon sapiens chimeric sequence

<400> SEQUENCE: 7
```

| | | | | | | | | | | | | | | |
|---|---|---|---|---|---|---|---|---|---|---|---|---|---|---|
| Met | Ala | Trp | Val | Trp | Thr | Leu | Leu | Phe | Leu | Met | Ala | Ala | Gln | Ser |
| 1 | | | | 5 | | | | | 10 | | | | | 15 |
| Ile | Gln | Ala | Gln | Ile | Gln | Leu | Val | Gln | Ser | Gly | Pro | Glu | Leu | Lys | Lys |
| | | 20 | | | | | 25 | | | | | 30 | | |
| Pro | Gly | Glu | Thr | Val | Lys | Ile | Ser | Cys | Lys | Ala | Ser | Gly | Tyr | Ala | Phe |
| | | | 35 | | | | | 40 | | | | | 45 | |
| Thr | Asp | Tyr | Ser | Met | Asn | Trp | Val | Lys | Gln | Ala | Pro | Gly | Lys | Gly | Leu |
| | 50 | | | | | 55 | | | | | 60 | | | | |
| Arg | Trp | Met | Gly | Trp | Ile | Asn | Thr | Glu | Thr | Gly | Glu | Pro | Thr | Tyr | Thr |
| 65 | | | | | 70 | | | | | 75 | | | | | 80 |
| Asp | Asp | Phe | Lys | Gly | Arg | Phe | Ala | Phe | Ser | Leu | Glu | Thr | Ser | Ala | Ser |
| | | | | 85 | | | | | 90 | | | | | 95 | |
| Thr | Ala | Phe | Leu | Gln | Ile | Asn | Asn | Leu | Arg | Asn | Glu | Asp | Thr | Ala | Thr |
| | | | 100 | | | | | 105 | | | | | 110 | | |
| Tyr | Phe | Cys | Ala | Arg | His | Tyr | Asp | Tyr | Gly | Gly | Phe | Pro | Tyr | Trp | Gly |
| | | 115 | | | | | 120 | | | | | 125 | | | |
| Gln | Gly | Thr | Leu | Val | Thr | Val | Ser | Ser | Ala | Ser | Thr | Lys | Gly | Pro | Ser |
| 130 | | | | | 135 | | | | | 140 | | | | | |
| Val | Phe | Pro | Leu | Ala | Pro | Ser | Ser | Lys | Ser | Thr | Ser | Gly | Gly | Thr | Ala |
| 145 | | | | | 150 | | | | | 155 | | | | | 160 |
| Ala | Leu | Gly | Cys | Leu | Val | Lys | Asp | Tyr | Phe | Pro | Glu | Pro | Val | Thr | Val |
| | | | | 165 | | | | | 170 | | | | | 175 | |
| Ser | Trp | Asn | Ser | Gly | Ala | Leu | Thr | Ser | Gly | Val | His | Thr | Phe | Pro | Ala |
| | | | 180 | | | | | 185 | | | | | 190 | | |
| Val | Leu | Gln | Ser | Ser | Gly | Leu | Tyr | Ser | Leu | Ser | Ser | Val | Val | Thr | Val |
| | | 195 | | | | | 200 | | | | | 205 | | | |
| Pro | Ser | Ser | Ser | Leu | Gly | Thr | Gln | Thr | Tyr | Ile | Cys | Asn | Val | Asn | His |
| 210 | | | | | 215 | | | | | 220 | | | | | |
| Lys | Pro | Ser | Asn | Thr | Lys | Val | Asp | Lys | Val | Glu | Pro | Lys | Ser | Cys |
| 225 | | | | | 230 | | | | | 235 | | | | | 240 |
| Asp | Lys | Thr | His | Thr | Cys | Pro | Pro | Cys | Pro | Ala | Pro | Glu | Leu | Leu | Gly |
| | | | | 245 | | | | | 250 | | | | | 255 | |
| Gly | Pro | Ser | Val | Phe | Leu | Phe | Pro | Pro | Lys | Pro | Lys | Asp | Thr | Leu | Met |
| | | | 260 | | | | | 265 | | | | | 270 | | |
| Ile | Ser | Arg | Thr | Pro | Glu | Val | Thr | Cys | Val | Val | Val | Asp | Val | Ser | His |
| | | 275 | | | | | 280 | | | | | 285 | | | |
| Glu | Asp | Pro | Glu | Val | Lys | Phe | Asn | Trp | Tyr | Val | Asp | Gly | Val | Glu | Val |
| 290 | | | | | 295 | | | | | 300 | | | | | |
| His | Asn | Ala | Lys | Thr | Lys | Pro | Arg | Glu | Glu | Gln | Tyr | Asn | Ser | Thr | Tyr |
| 305 | | | | | 310 | | | | | 315 | | | | | 320 |
| Arg | Val | Val | Ser | Val | Leu | Thr | Val | Leu | His | Gln | Asp | Trp | Leu | Asn | Gly |
| | | | | 325 | | | | | 330 | | | | | 335 | |
| Lys | Glu | Tyr | Lys | Cys | Lys | Val | Ser | Asn | Lys | Ala | Leu | Pro | Ala | Pro | Ile |
| | | | 340 | | | | | 345 | | | | | 350 | | |

Glu Lys Thr Ile Ser Lys Ala Lys Gly Gln Pro Arg Glu Pro Gln Val
             355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
             405                 410                 415

Val Leu Asp Ser Asp Gly Ser Phe Phe Leu Tyr Ser Lys Leu Thr Val
             420                 425                 430

Asp Lys Ser Arg Trp Gln Gln Gly Asn Val Phe Ser Cys Ser Val Met
             435                 440                 445

His Glu Ala Leu His Asn His Tyr Thr Gln Lys Ser Leu Ser Leu Ser
             450                 455                 460

Pro Gly Lys
465

<210> SEQ ID NO 8
<211> LENGTH: 234
<212> TYPE: PRT
<213> ORGANISM: Artificial Sequence
<220> FEATURE:
<223> OTHER INFORMATION: Mus musculus/Homon sapiens chimeric sequence

<400> SEQUENCE: 8

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
             20                  25                  30

Ala Ser Val Gly Glu Thr Val Thr Ile Thr Cys Arg Ala Ser Gly Asn
             35                  40                  45

Val His Asn Tyr Leu Ala Trp Tyr Gln Gln Lys Gln Gly Lys Ser Pro
     50                  55                  60

Gln Leu Leu Val Tyr Thr Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
             85                  90                  95

Ser Leu Gln Pro Glu Asp Phe Gly Thr Tyr Tyr Cys Gln His Phe Trp
             100                 105                 110

Ser Asn Pro Trp Thr Phe Gly Gly Gly Thr Lys Leu Glu Ile Lys Arg
             115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
             165                 170                 175

Gly Asn Ser Gln Glu Ser Val Thr Glu Gln Asp Ser Lys Asp Ser Thr
             180                 185                 190

Tyr Ser Leu Ser Ser Thr Leu Thr Leu Ser Lys Ala Asp Tyr Glu Lys
             195                 200                 205

His Lys Val Tyr Ala Cys Glu Val Thr His Gln Gly Leu Ser Ser Pro
     210                 215                 220

Val Thr Lys Ser Phe Asn Arg Gly Glu Cys
225                 230

<210> SEQ ID NO 9
<211> LENGTH: 266
<212> TYPE: PRT
<213> ORGANISM: Artificial Sequence
<220> FEATURE:
<223> OTHER INFORMATION: Mus musculus/Homo sapiens chimeric sequence

<400> SEQUENCE: 9

```
Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ala Phe
        35                  40                  45

Thr Asp Tyr Ser Met Asn Trp Val Lys Gln Ala Pro Gly Lys Gly Leu
    50                  55                  60

Arg Trp Met Gly Trp Ile Asn Thr Glu Thr Gly Glu Pro Thr Tyr Thr
65                  70                  75                  80

Asp Asp Phe Lys Gly Arg Phe Ala Phe Ser Leu Glu Thr Ser Ala Ser
                85                  90                  95

Thr Ala Phe Leu Gln Ile Asn Asn Leu Arg Asn Glu Asp Thr Ala Thr
            100                 105                 110

Tyr Phe Cys Ala Arg His Tyr Asp Tyr Gly Gly Phe Pro Tyr Trp Gly
        115                 120                 125

Gln Gly Thr Leu Val Thr Val Ser Ser Gly Gly Gly Ser Gly Gly
    130                 135                 140

Gly Gly Ser Gly Gly Gly Ser Asp Ile Gln Met Thr Gln Ser Pro
145                 150                 155                 160

Ala Ser Leu Ser Ala Ser Val Gly Glu Thr Val Thr Ile Thr Cys Arg
                165                 170                 175

Ala Ser Gly Asn Val His Asn Tyr Leu Ala Trp Tyr Gln Gln Lys Gln
            180                 185                 190

Gly Lys Ser Pro Gln Leu Leu Val Tyr Thr Ala Lys Thr Leu Ala Asp
        195                 200                 205

Gly Val Pro Ser Arg Phe Ser Gly Ser Gly Ser Gly Thr Gln Tyr Ser
    210                 215                 220

Leu Lys Ile Asn Ser Leu Gln Pro Glu Asp Phe Gly Thr Tyr Tyr Cys
225                 230                 235                 240

Gln His Phe Trp Ser Asn Pro Trp Thr Phe Gly Gly Gly Thr Lys Leu
                245                 250                 255

Glu Ile Lys His His His His His His Cys
            260                 265
```

<210> SEQ ID NO 10
<211> LENGTH: 717
<212> TYPE: DNA
<213> ORGANISM: Mus musculus

<400> SEQUENCE: 10

```
atgggcatca agatggagtc acagactcag gtctttgtat acatgttgct gtggttgtct     60
ggtgttgatg gagacattgt gatgacccag tctcaaaagt tcatgtccac atcaatagga    120
gacagggtca gcgtcacctg caaggccagt cagaatgtgg ttctcatgt agcctggttt    180 cagcagaaac cagggcaatc tcctaaagca ctgatttact cggcatccta ccggtacagc    240
ggagtcactg atcgcttcac aggcagtgga tctgggacag atttcactct caccatcaac    300
```

```
aatgtgcagt ctgaagactt ggcagagtat ttctgtcagc aatataacag ttttccattc    360
acgttcggtt cggggacaaa gttggaaata aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata cagctatac ctgtgaggcc     660 actcacaaga catcaacttc acccattgtc aagagcttca acaggaatga gtgttag      717

<210> SEQ ID NO 11
<211> LENGTH: 238
<212> TYPE: PRT
<213> ORGANISM: Mus musculus

<400> SEQUENCE: 11

Met Gly Ile Lys Met Glu Ser Gln Thr Gln Val Phe Val Tyr Met Leu
1               5                   10                  15

Leu Trp Leu Ser Gly Val Asp Gly Asp Ile Val Met Thr Gln Ser Gln
            20                  25                  30

Lys Phe Met Ser Thr Ser Ile Gly Asp Arg Val Ser Val Thr Cys Lys
        35                  40                  45

Ala Ser Gln Asn Val Gly Ser His Val Ala Trp Phe Gln Gln Lys Pro
    50                  55                  60

Gly Gln Ser Pro Lys Ala Leu Ile Tyr Ser Ala Ser Tyr Arg Tyr Ser
65                  70                  75                  80

Gly Val Thr Asp Arg Phe Thr Gly Ser Gly Ser Gly Thr Asp Phe Thr
                85                  90                  95

Leu Thr Ile Asn Asn Val Gln Ser Glu Asp Leu Ala Glu Tyr Phe Cys
            100                 105                 110

Gln Gln Tyr Asn Ser Phe Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

THERAPEUTIC ANTIBODIES AND USES THEREOF

INCORPORATION BY CROSS-REFERENCE

The present application claims priority from Australian provisional patent application number 2015901423 filed on 20 Apr. 2015, the entire content of which is incorporated herein by cross-reference.

TECHNICAL FIELD

The present invention relates generally to the field of prostate, pancreatic and/or bladder cancers. More specifically, the present invention relates to the use of antibodies in treatment of prostate, pancreatic and/or bladder cancers.

BACKGROUND

Prostate cancer is the most commonly occurring tumour in males and is second only to lung cancer in mortality. Treatment with surgery and/or radiotherapy is successful in many patients if prostate cancer is diagnosed early. However, many patients with advanced disease and a sizeable proportion of all prostate cancer patients eventually develop metastatic disease following localised therapy.

Bladder cancer is estimated to affect approximately 77,000 adults in the US annually, with an estimated 16,000 fatalities. A comparable number of persons in the US are predicted to be diagnosed with pancreatic cancer in 2016 (53,000) with a very high mortality rate (41,000). Common treatments for these cancers include surgical removal, radiation therapy, and/or chemotherapy.

Despite their promise as effective agents in the treatment of cancer there are no therapeutic antibodies with regulatory approval for the treatment of prostate, pancreatic or bladder cancers. U.S. Pat. No. 5,622,836 to Walker et al. discloses an antibody named BLCA-38 (BLCA—"bladder cancer"). The document teaches that BLCA-38 is a monoclonal antibody specific for an unknown antigen expressed by bladder carcinoma cells. BLCA-38 is also taught to show specificity for human ovarian and colonic cancer cell lines, as well as some melanoma cell lines, but not to lymphoid (T lymphoid or B lymphoid) and leukemic cell lines.

Subsequently, Russell et al. (2004) (Russell et al., "Cytotoxic properties of immunoconjugates containing melittin-like peptide 101 against prostate cancer: in vitro & in vivo studies". Cancer Immunol Immunother 2004: 53(5): 411-421) published a study in which BLCA-38 was used to target a cytotoxic peptide to prostate cancer cells. The authors indicate that BLCA-38 is a murine monoclonal antibody raised against the human bladder cancer cell line UCRU-BL-17CL.

A further publication by Russell et al. in 2004 (Russell et al., "Immunohistochemical characterization of the monoclonal antibody, BLCA38, for the detection of prostate cancer". Cancer Immunol Immunother 2004: 53(11) 995-1004) also teaches that BLCA-38 is a murine monoclonal antibody raised against a human bladder cell line which is capable of binding to bladder carcinoma cells, prostate cancer cells, and vulval epidermoid cells, but not to breast cancer cells. The article indicates that BLCA-38 is specific for an antigen of approximately 30 kDa in size that is difficult to characterise or identify.

Carter et al. (2004) (Carter et al., "Biodistributions of intact monoclonal antibodies and fragments of BLCA38, a new prostate cancer directed antibody". Cancer Immunol Immunother 2004: 53(6) 533-542) analysed timing and dosage for targeting therapeutic agents to prostate cancer cells using BLCA-38, also indicating that it is a murine monoclonal antibody targeting an antigen of around 30 kDa expressed on the cell surface and in the cytoplasm. The authors state that the nature of the antigen is elusive, and indicate that it is expressed on bladder and prostate cancer cells.

An article by Khatri et al. published in 2010 (Khatri et al. "Promise of BLCA38 as a Targeting Antibody for Tissue-Specific Gene Delivery to Prostate Cancer". Austral-Asian J. Cancer 2010: 9(3): 195-203) reiterated that BLCA-38 is a murine monoclonal antibody specific for prostate cancer cells. The authors reveal that although BLCA-38 is not internalised upon binding to its antigen, conjugation with a virus facilitated internalisation of the antibody resulting in increased expression of the reporter gene.

Unlike many cancer treatments that may damage cancer and healthy cells alike, targeted cancer therapies are designed to selectively attack tumor cells while avoiding healthy cells and tissues in the patient under treatment. For example, targeted antibody-drug conjugates (ADCs) selectively deliver cytotoxic agents to cancer cells by virtue of specific binding to markers produced specifically by the cancer cells. The capacity of these agents to deliver their toxic payload to cancerous cells and avoid damaging healthy tissue is obviously important. Additionally, internalisation of ADCs upon specifically binding to cancer cells can enhance their cytotoxic effects as opposed to ADCs that are not internalised. Internalisation can allow the tailoring of ADCs to enhance their effects upon uptake into cellular vesicles (e.g. endosomes and lysosomes). It is also noteworthy that internalisation of ADCs does not necessarily induce effective cell killing, an observation that may at least in part arise from differential endosomal/lysosomal processing pathways in different types of cancer cells.

Therapeutic antibodies may require substantial quantities of product over multiple dosages to be clinically effective (e.g. 200-350 mg/m$^2$ per dose). A therapeutic dose of ADC may often be marginally less than that of naked therapeutic monoclonal antibodies (TMAs) (e.g. at 160 mg per dose). However, ADC construction involves additional technologies such as chemical conjugation steps that complicate production streams and can raise the cost of manufacture significantly. It is therefore desirable to provide therapeutic dose ADCs at lower cost where possible.

Despite the promise that antibodies offer as therapeutic agents, a need continues to exist for effective therapeutic antibodies to treat prostate, bladder, and/or pancreatic cancer.

SUMMARY OF THE INVENTION

The present inventors have surprisingly identified that the BLCA-38 antibody referred to and used in the aforementioned prior art is a combination of two distinct monoclonal antibodies in a mixed population. It has been determined that only one of these antibody species is capable of binding strongly to the relevant target antigen present on prostate cancer cells, whilst the second species cannot. Moreover, it has been unexpectedly discovered that the antibody species is capable of binding to the relevant target antigen present on prostate cancer cells is internalised upon doing so, despite the aforementioned prior art indicating to the contrary. Moreover, the present inventors have demonstrated effective internalisation in prostate, bladder and pancreatic cancer cells providing a means of targeting and killing these cancer cell types.

Accordingly, in a first aspect the present invention provides a method for treating prostate, bladder, and/or pancreatic cancer in a subject, the method comprising administering to the subject a pharmaceutical preparation comprising an anti-glypican-1 (anti-GPC1) antibody and/or an antigen-binding fragment thereof, wherein the antibody and/or fragment is conjugated to at least one cytotoxic agent that is toxic to a prostate, bladder, and/or pancreatic cancer cell in the subject.

In a second aspect, the present invention provides a method for killing a prostate, bladder, and/or pancreatic cancer cell in a subject, the method comprising administering to the subject a pharmaceutical preparation comprising an anti-glypican-1 (anti-GPC1) antibody and/or an antigen-binding fragment thereof, wherein the antibody and/or fragment is conjugated to at least one cytotoxic agent that is toxic to the prostate, bladder, and/or pancreatic cancer cell in the subject.

In a third aspect, the present invention provides a method for treating a prostate, bladder, and/or pancreatic cancer tumour in a subject, the method comprising administering to the subject a pharmaceutical preparation comprising an anti-glypican-1 (anti-GPC1) antibody and/or an antigen-binding fragment thereof, wherein the antibody and/or fragment is conjugated to at least one cytotoxic agent that is toxic to a prostate, bladder, and/or pancreatic cancer cell in the tumour.

In a fourth aspect, the present invention provides use of an anti-glypican-1 (anti-GPC1) antibody and/or an antigen-binding fragment thereof in the preparation of a medicament for treating prostate, bladder, and/or pancreatic cancer in a subject, wherein the antibody and/or fragment is conjugated to at least one cytotoxic agent that is toxic to a prostate, bladder, and/or pancreatic cancer cell in the subject.

In a fifth aspect, the present invention provides use of an anti-glypican-1 (anti-GPC1) antibody and/or an antigen-binding fragment thereof in the preparation of a medicament for killing a prostate, bladder, and/or pancreatic cancer cell in a subject, wherein the antibody and/or fragment is conjugated to at least one cytotoxic agent that is toxic to a prostate, bladder, and/or pancreatic cancer cell in the subject.

In a sixth aspect, the present invention provides use of an anti-glypican-1 (anti-GPC1) antibody and/or an antigen-binding fragment thereof in the preparation of a medicament treating a prostate, bladder, and/or pancreatic cancer tumour in a subject, wherein the antibody and/or fragment is conjugated to at least one cytotoxic agent that is toxic to a prostate, bladder, and/or pancreatic cancer cell in the subject.

In a seventh aspect, the present invention provides an anti-glypican-1 (anti-GPC1) antibody and/or an antigen-binding fragment thereof for use in treating prostate, bladder, and/or pancreatic cancer in a subject, wherein the antibody and/or fragment is conjugated to at least one cytotoxic agent that is toxic to a prostate, bladder, and/or pancreatic cancer cell in the subject.

In an eighth aspect, the present invention provides an anti-glypican-1 (anti-GPC1) antibody and/or an antigen-binding fragment thereof for use in killing a prostate, bladder, and/or pancreatic cancer cell in a subject, wherein the antibody and/or fragment is conjugated to at least one cytotoxic agent that is toxic to the prostate, bladder, and/or pancreatic cancer cell in the subject.

In a ninth aspect, the present invention provides an anti-glypican-1 (anti-GPC1) antibody and/or an antigen-binding fragment thereof for use in treating a prostate, bladder, and/or pancreatic cancer tumour in a subject, wherein the antibody and/or fragment is conjugated to at least one cytotoxic agent that is toxic to a prostate, bladder, and/or pancreatic cancer cell in the subject.

In a tenth aspect, the present invention provides a method of radioimaging a prostate, bladder, and/or pancreas in a subject, the method comprising:

administering to the subject a pharmaceutical preparation comprising an anti-glypican-1 (anti-GPC1) antibody and/or an antigen-binding fragment thereof, wherein the antibody and/or fragment is conjugated to at least one radioimaging agent, detecting radiation emitted by the radioimaging agent, and using the detected radiation to form a radioimage of the prostate, bladder, and/or pancreas.

In one embodiment of the tenth aspect, the prostate of the subject is characterised by benign prostatic hyperplasia (BPH).

In one embodiment of the tenth aspect, the prostate, bladder and/or pancreas of the subject is cancerous. In one embodiment of the tenth aspect, the subject suffers from prostate, bladder and/or pancreatic cancer.

In one embodiment of the tenth aspect, the radioimaging agent is selected from the group consisting of: $^{18}$F, $^{67}$Ga, $^{68}$Ga, $^{81m}$Kr, $^{82}$Rb, $^{13}$N, $^{99m}$Tc, $^{111}$In, $^{123}$I, $^{124}$I, $^{133}$Xe, $^{201}$Tl, $^{177}$Lu, $^{89}$Zr, $^{64}$Cu, $^{67}$Cu, $^{32}$P, and any combination thereof.

In one embodiment of the tenth aspect, the radioimaging is single-photon emission computed tomography (SPECT) and the radioimaging agent is selected from the group consisting of: $^{99m}$Tc, $^{111}$In, $^{67}$Ga, $^{123}$I, and any combination thereof.

In one embodiment of the tenth aspect, the radioimaging is positron emission tomography (PET) and the radioimaging agent is selected from the group consisting of: $^{18}$F, $^{68}$Ga, $^{64}$Cu, $^{86}$Y, $^{124}$I, $^{89}$Zr, and any combination thereof.

In one embodiment of the above aspects, the pharmaceutical preparation does not comprise an antibody with a light chain variable region comprising:

a complementarity determining region 1 (CDR1) comprising or consisting of an amino acid sequence defined by positions 48-58 of SEQ ID NO: 11;

a complementarity determining region 2 (CDR2) comprising or consisting of an amino acid sequence defined by positions 74-80 of SEQ ID NO: 11;

a complementarity determining region 3 (CDR3) comprising or consisting of an amino acid sequence defined by positions 113-121 of SEQ ID NO: 11.

In another embodiment of the above aspects, the cytotoxic agent is a prodrug designed for activation upon uptake into an endosome or lysosome of said prostate, bladder, and/or pancreatic cancer cell.

In another embodiment of the above aspects, the prodrug is conjugated to the antibody and/or an antigen-binding fragment thereof by:

an acid sensitive-linker susceptible to cleavage at a pH that is less than: pH 7.2, pH 7.0, pH 6.5, pH 6.0, pH 5.5, pH 5.0, pH 4.5, or pH 4.

an enzyme-cleavable linker, wherein the enzyme capable of cleaving the linker exists within the endosome or lysosome.

In another embodiment of the above aspects, the cytotoxic agent is linked to the antibody and/or antigen binding fragment thereof by binding to a chelating agent conjugated to the antibody and/or antigen binding fragment thereof.

In an additional embodiment of the above aspects, the antibody comprises:

(a) a heavy chain variable region comprising:
  a complementarity determining region 1 (CDR1) comprising or consisting of an amino acid sequence defined by positions 50-54 of SEQ ID NO: 3;
  a complementarity determining region 2 (CDR2) comprising or consisting of an amino acid sequence defined by positions 69-85 of SEQ ID NO: 3;
  a complementarity determining region 3 (CDR3) comprising or consisting of an amino acid sequence defined by positions 118-126 of SEQ ID NO: 3; and (b) a light chain variable region comprising:
  a complementarity determining region 1 (CDR1) comprising or consisting of an amino acid sequence defined by positions 44-54 of SEQ ID NO: 4;
  a complementarity determining region 2 (CDR2) comprising or consisting of an amino acid sequence defined by positions 70-76 of SEQ ID NO: 4;
  a complementarity determining region 3 (CDR3) comprising or consisting of an amino acid sequence defined by positions 109-117 of SEQ ID NO: 4.

In one embodiment of the above aspects, the antibody is produced by a hybridoma cell as deposited at Cellbank Australia under accession number CBA20140026, or progeny thereof.

In a further embodiment of the above aspects, the antibody is:
  (i) a humanised anti-GPC1 antibody,
  (ii) a chimeric anti-GPC1 antibody,
  (i) a human anti-GPC1 antibody,
  (ii) a monoclonal anti-GPC1 antibody,
  (iii) a multimeric anti-GPC1 antibody, or
  (iv) a synthetic anti-GPC1 antibody.

In one embodiment of the above aspects, the antibody is a chimeric antibody comprising:
  (a) a heavy chain constant region comprising or consisting of an amino acid sequence as defined in residues 138-467 of SEQ ID NO: 7; and
  (b) a light chain constant region comprising or consisting of an amino acid sequence as defined in residues of 128-234 SEQ ID NO: 8.

In another embodiment of the above aspects, the antigen-binding fragment thereof is: a single chain variable fragment (scFv), a variable domain (Fv) fragment, a fragment antigen binding (Fab) fragment, a F(ab)2 fragment, a peptide, or a proteolytic fragment containing an epitope binding region.

In yet another embodiment of the above aspects, the antigen-binding fragment thereof is: a single chain variable fragment (scFv) comprising a sequence as defined in SEQ ID NO: 9.

In still another embodiment of the above aspects, the cytotoxic agent is selected from the group consisting of: an adrenocortical suppressant, an alkylating agent, an alkyl sulfonate, an anthracycline, an anti-angiogenic agent, an antibiotic, an antimetabolite, an antimitotic, an auristatin, a calicheamycin, a camptothecin, a COX-2 inhibitor, an enzyme inhibitor, an epipodophyllotoxin, an ethylenimine derivative, a folic acid analog, an HDAC inhibitor, a heat shock protein (HSP90) inhibitor, a hormone antagonist, a maytansinoid, a methyl hydrazine derivative, an mTOR inhibitor, a nitrogen mustard, a nitrosourea, a platinum coordination complex, a pro-apoptotic agent, a proteosome inhibitor, a purine analog, a pyrimidine analog, a radioisotope, a substituted urea, a taxane, triazene, a tubulin inhibitor, a tyrosine kinase inhibitor, and a vinca alkaloid.

In still another embodiment of the above aspects, the cytotoxic agent is selected from the group consisting of: afatinib, aplidin, anastrozole, anthracyclines, AVL-101, AVL-291, axitinib, azaribine, bendamustine, bleomycin, bortezomib, bosutinib, bryostatin-1, busulfan, camptothecans, carboplatin, calicheamycin, camptothecin, carboplatin, carmustine, celecoxib, chlorambucil, cisplatinum, cladribine, COX-2 inhibitors, crizotinib, cyano-morpholino doxorubicin, cyclophosphamide, cytarabine, dacarbazine, dactinomycin, dasatinib, daunorubicin, dinaciclib, 3',5'-O-dioleoyl-FudR (FUdR-d0), DM1, DM3, DM4, docetaxel, doxorubicin, doxorubicin glucuronide, duocarmycin, endostatin, entinostat, epidophyllotoxin, epirubicin glucuronide, erlotinib, estramustine, estrogen receptor binding agents, etoposide glucuronide, etoposide phosphate, etoposide (VP16), exemestane, farnesyl-protein transferase inhibitors, fingolimod, flavopiridol, floxuridine (FUdR), fludarabine, 5-fluorouracil, flutamide, fostamatinib, ganetespib, GDC-0834, gefitinib, gemcitabine, GS-1101, 10-hydroxycamptothecin, hydroxyurea, ibrutinib, idarubicin, idelalisib, ifosfamide, imatinib, irinotecan (CPT-11), lapatinib, lenolidamide, leucovorin, LFM-A13, lomustine, mechlorethamine, melphalan, mercaptopurine, 6-mercaptopurine, methotrexate, mithramycin, mitomycin, mitotane, mitoxantrone, monomethylauristatin D (MMAD), monomethylauristatin E (MMAE), monomethylauristatin F (MMAF), navelbine, neratinib, nilotinib, nitrosurea, olaparib, paclitaxel, PCI-32765, pentostatin, plicomycin, a 2-PDox pro-drug (pro-2-PDox), procarbazine, PSI-341, 2-pyrrolinodoxorubicine (2-PDox), raloxifene, semustine, SN-38, sorafenib, streptozocin, SU1 1248, sunitinib, tamoxifen, temazolomide, s15 teniposide, thalidomide, thioguanine, thiotepa, topotecan, transplatinum, uracil mustard, vatalanib, vinblastine, vinca alkaloids, vincristine, vinorelbine, and ZD 1839.

In still another embodiment of the above aspects, the cytotoxic agent is a radioisotope selected from the group consisting of: $^{90}$Y, $^{188}$Re, $^{166}$Ho, $^{165}$Dy, $^{109}$Pd, $^{111}$Ag, $^{186}$Re, $^{198}$Au, $^{153}$Sm, $^{64}$Cu, $^{177}$Lu, $^{131}$I, $^{125}$I, $^{67}$Cu, $^{175}$Yb, $^{166}$Dy, $^{169}$Er, $^{212}$Bi, $^{213}$Bi, $^{225}$Ac, $^{212}$Pb, $^{66}$Ga, $^{67}$Ga, $^{68}$Ga, $^{86}$Y, $^{94m}$Tc, and $^{89}$Zr.

In still another embodiment of the above aspects, the antibody or antigen-binding fragment thereof is conjugated with a chelating agent selected from the group consisting of: DOTA, DTPA, NOTA, NODAGA, MeCOSAR, TETA, TRAP, TE2A, CBTE2A.

In still another embodiment of the above aspects, the cytotoxic agent and the antibody or antigen-binding fragment thereof are conjugated with a chelating agent selected from the group consisting of: DOTA, DTPA, NOTA, NODAGA, MeCOSAR, TETA, TRAP, TE2A, CBTE2A.

In a further embodiment of the above aspects, the subject is a mammalian subject or a human subject.

In an eleventh aspect, the present invention provides an isolated antibody population comprising:
  first antibodies and/or antigen binding fragments thereof, that are conjugated to at least one cytotoxic agent which is toxic to a prostate, bladder, and/or pancreatic cancer cell, wherein the first antibodies comprise:
    (a) a heavy chain variable region comprising:
      a complementarity determining region 1 (CDR1) comprising or consisting of an amino acid sequence defined by positions 50-54 of SEQ ID NO: 3;

a complementarity determining region 2 (CDR2) comprising or consisting of an amino acid sequence defined by positions 69-85 of SEQ ID NO: 3;
a complementarity determining region 3 (CDR3) comprising or consisting of an amino acid sequence defined by positions 118-126 of SEQ ID NO: 3; and
(b) a light chain variable region comprising:
a complementarity determining region 1 (CDR1) comprising or consisting of an amino acid sequence defined by positions 44-54 of SEQ ID NO: 4;
a complementarity determining region 2 (CDR2) comprising or consisting of an amino acid sequence defined by positions 70-76 of SEQ ID NO: 4;
a complementarity determining region 3 (CDR3) comprising or consisting of an amino acid sequence defined by positions 109-117 of SEQ ID NO: 4;
and wherein the antibody population does not contain second antibodies comprising a light chain variable region comprising:
a complementarity determining region 1 (CDR1) comprising or consisting of an amino acid sequence defined by positions 48-58 of SEQ ID NO: 11;
a complementarity determining region 2 (CDR2) comprising or consisting of an amino acid sequence defined by positions 74-80 of SEQ ID NO: 11;
a complementarity determining region 3 (CDR3) comprising or consisting of an amino acid sequence defined by positions 113-121 of SEQ ID NO: 11.

In one embodiment of the eleventh aspect, the first antibodies and/or antigen binding fragments thereof are any one or more of monoclonal antibodies, humanised antibodies, chimeric antibodies, multimeric antibodies, and/or synthetic antibodies.

In another embodiment of the eleventh aspect, the antigen binding fragments are any one or more of single chain variable fragments (scFv), variable domain (Fv) fragments, fragment antigen binding (Fab) fragments, F(ab)2 fragments, peptides, or proteolytic fragments containing an epitope binding region.

In an additional embodiment of the eleventh aspect, the first antibodies comprise or consist of a heavy chain sequence as defined by positions 20-461 of SEQ ID NO: 3 and a light chain sequence as defined by positions 21-234 of SEQ ID NO: 4.

In a further embodiment of the eleventh aspect, the first antibodies and/or antigen binding fragments thereof are chimeric.

In a further embodiment of the eleventh aspect, the first antibodies and/or antigen binding fragments thereof are chimeric antibodies comprising:
(a) a heavy chain constant region comprising or consisting of an amino acid sequence as defined in residues 138-467 of SEQ ID NO: 7; and
(b) a light chain constant region comprising or consisting of an amino acid sequence as defined in residues of 128-234 SEQ ID NO: 8.

In another embodiment of the eleventh aspect, the antigen binding fragments are single chain variable fragments (scFv) comprising a sequence as defined in SEQ ID NO: 9.

In yet another embodiment of the eleventh aspect, the cytotoxic agent is selected from the group consisting of: an adrenocortical suppressant, an alkylating agent, an alkyl sulfonate, an anthracycline, an anti-angiogenic agent, an antibiotic, an antimetabolite, an antimitotic, an auristatin, a calicheamycin, a camptothecin, a COX-2 inhibitor, an enzyme inhibitor, an epipodophyllotoxin, an ethylenimine derivative, a folic acid analog, an HDAC inhibitor, a heat shock protein (HSP90) inhibitor, a hormone antagonist, a maytansinoid, a methyl hydrazine derivative, an mTOR inhibitor, a nitrogen mustard, a nitrosourea, a platinum coordination complex, a pro-apoptotic agent, a proteosome inhibitor, a purine analog, a pyrimidine analog, a radioisotope, a substituted urea, a taxane, triazene, a tubulin inhibitor, a tyrosine kinase inhibitor, and a vinca alkaloid.

In another embodiment of the eleventh aspect, the cytotoxic agent is selected from the group consisting of: afatinib, aplidin, anastrozole, anthracyclines, AVL-101, AVL-291, axitinib, azaribine, bendamustine, bleomycin, bortezomib, bosutinib, bryostatin-1, busulfan, camptothecans, carboplatin, calicheamycin, camptothecin, carboplatin, carmustine, celecoxib, chlorambucil, cisplatinum, cladribine, COX-2 inhibitors, crizotinib, cyano-morpholino doxorubicin, cyclophosphamide, cytarabine, dacarbazine, dactinomycin, dasatinib, daunorubicin, dinaciclib, 3',5'-O-diolcoyl-FudR (FUdR-d0), DM1, DM3, DM4, docetaxel, doxorubicin, doxorubicin glucuronide, duocarmycin, endostatin, entinostat, epidophyllotoxin, epirubicin glucuronide, erlotinib, estramustine, estrogen receptor binding agents, etoposide glucuronide, etoposide phosphate, etoposide (VP16), exemestane, farnesyl-protein transferase inhibitors, fingolimod, flavopiridol, floxuridine (FUdR), fludarabine, 5-fluorouracil, flutamide, fostamatinib, ganetespib, GDC-0834, gefitinib, gemcitabine, GS-1101, 10-hydroxycamptothecin, hydroxyurea, ibrutinib, idarubicin, idelalisib, ifosfamide, imatinib, irinotecan (CPT-11), lapatinib, lenolidamide, leucovorin, LFM-A13, lomustine, mechlorethamine, melphalan, mercaptopurine, 6-mercaptopurine, methotrexate, mithramycin, mitomycin, mitotane, mitoxantrone, monomethylauristatin D (MMAD), monomethylauristatin E (MMAE), monomethylauristatin F (MMAF), navelbine, neratinib, nilotinib, nitrosurea, olaparib, paclitaxel, PCI-32765, pentostatin, plicomycin, a 2-PDox pro-drug (pro-2-PDox), procarbazine, PSI-341, 2-pyrrolinodoxorubicine (2-PDox), raloxifene, semustine, SN-38, sorafenib, streptozocin, SU1 1248, sunitinib, tamoxifen, temazolomide, teniposide, thalidomide, thioguanine, thiotepa, topotecan, transplatinum, uracil mustard, vatalanib, vinblastine, vinca alkaloids, vincristine, vinorelbine, and ZD 1839.

In yet another embodiment of the eleventh aspect, the cytotoxic agent is a prodrug designed for activation upon uptake into an endosome or lysosome of said prostate, bladder, and/or pancreatic cancer cell.

In one embodiment of the eleventh aspect, the prodrug is conjugated to the antibody and/or an antigen-binding fragment thereof by:
an acid sensitive-linker susceptible to cleavage at a pH that is less than: pH 7.2, pH 7.0, pH 6.5, pH 6.0, pH 5.5, pH 5.0, pH 4.5, or pH 4; or an enzyme-cleavable linker, wherein the enzyme capable of cleaving the linker exists within the endosome or lysosome.

In one embodiment of the eleventh aspect, the cytotoxic agent is linked to the antibody and/or antigen binding fragment thereof by binding to a chelating agent conjugated to the antibody and/or antigen binding fragment thereof.

In still another embodiment of the eleventh aspect, the cytotoxic agent and the antibody or antigen-binding fragment thereof are conjugated with a chelating agent selected from the group consisting of: DOTA, DTPA, NOTA, NODAGA, MeCOSAR, TETA, TRAP, TE2A, CBTE2A.

In still another embodiment of the eleventh aspect, the cytotoxic agent is a radioisotope selected from the group consisting of: $^{90}$Y, $^{188}$Re, $^{166}$Ho, $^{165}$Dy, $^{109}$Pd, $^{111}$Ag, $^{186}$Re, $^{198}$Au, $^{153}$Sm, $^{64}$Cu, $^{177}$Lu, $^{131}$I, $^{125}$I, $^{67}$Cu, $^{175}$Yb, $^{166}$Dy, $^{169}$Er, $^{212}$Bi, $^{213}$Bi, $^{225}$Ac, $^{212}$Pb, $^{66}$Ga, $^{67}$Ga, $^{68}$Ga, $^{86}$Y, $^{94m}$Tc, and $^{89}$Zr.

In still another embodiment of the eleventh aspect, the antibody or antigen-binding fragment thereof is conjugated with a chelating agent selected from the group consisting of: DOTA, DTPA, NOTA, NODAGA, MeCOSAR, TETA, TRAP, TE2A, and CBTE2A.

BRIEF DESCRIPTION OF THE DRAWINGS

Preferred embodiments of the present invention will now be described, by way of example only, with reference to the accompanying figures wherein:

FIG. 1 shows images from immunofluorescence assays using chimeric MIL-38 antibody and controls on DU-145 cells. FIG. 1A-D show combined bright field and DAPI images of the stained cells. FIG. 1E-H show binding to DU-145 cells with MIL-38 prep 33A (1E, positive control), chimeric MIL-38 (1F), Cetuximab (1G, positive control for human IgG1k), and negative control (1H, no 1' antibody);

FIG. 2 shows western blot analysis of chimeric MIL-38 antibody. FIG. 2A shows reactivity of murine MIL-38 with DU-145 MPEK extract, C3 MPEK extract and NS0-produced recombinant GPC-1 antigen. FIG. 2B shows reactivity of chimeric MIL-38 with DU-145 MPEK extract, C3 MPEK extract and NS0-produced recombinant GPC-1 antigen. FIG. 2C shows reactivity of murine MIL-38 with DU-145 MPEK extract, C3 MPEK extract and NS0-produced recombinant GPC-1 antigen under equivalent conditions to FIG. 2B;

FIG. 3 shows FLOW cytometry of fluorescently-labelled MIL-38 and scFv MIL-38 antibodies binding to DU-145 cells. FIG. 3A shows negative controls (cells alone and a negative control antibody). FIG. 3B shows reactivity of murine MIL-38 with DU-145 cells and also a reduction in FLOW signal when cells are pre-incubated with un-labelled MIL-38 antibody. FIG. 3C shows comparative binding of labelled MIL-38 and labelled MIL-38 scFv to DU-145 cells. MIL-38 scFv retains binding to DU-145 cells but at a slightly lower level than murine MIL-38;

FIG. 4 shows binding of MIL-38 antibody to MDA-MB-231 breast cancer cells, T-24 bladder cancer cells, PANC-1 pancreatic cancer cells and DU-145 prostate cancer cells. FIG. 4A shows binding of murine MIL-38 antibody to MDA-MB-231 cells. Binding of MIL-38 is considerably higher than isotype or secondary antibody only controls indicating MDA-MB-231 cells are positive for the MIL-38 antigen GPC-1. FIG. 4B shows overlaid FLOW cytometry histograms for MIL-38 binding to MDA-MB-231, T-24 or DU-145 cells. MDA-MB-231 cells showed the lowest binding, while the highest binding was observed for DU-145 cells. FIG. 4C shows overlaid FLOW cytometry histograms for MIL-38, anti-CD9 and anti-CD81 antibodies binding to PANC-1 cells.

FIG. 5 shows internalisation of MIL-38 antibody by MDA-MB-231, T-24 and DU-145 cells. FIG. 5A shows internalisation of the 1F5 murine MIL-38 parent antibody 30 min post binding to DU-145 cells. FIG. 5B shows shows internalisation of the chimeric MIL-38 antibody 30 min post binding to DU-145 cells. FIG. 5C shows lack of detectable antibody binding or internalisation of the chimeric MIL-38 antibody following 30 min of exposure to MDA-MB-231 cells. FIG. 5D shows internalisation of the chimeric MIL-38 antibody immediately post binding to T-24 cells; FIG. 5E shows localisation of chimeric MIL-38 antibody (green) in PANC-1 cells after 15 minutes of a 60 minute timecourse.

FIG. 5F shows internalisation of anti-human antibody labelled with Alexa-Fluor 488 in PANC-1 cells after completion of the 60 minute timecourse.

FIG. 6 shows targeting of either CY5-labelled 1F5 murine MIL-38 or CY5-labelled chimeric MIL-38 to subcutaneous DU-145 xenograft tumours. FIG. 6A shows targeting of 1F5 murine MIL-38 while FIG. 6B shows targeting of the chimeric MIL-38. Tumours are located on the back of the mice and are indicated by arrows. There is also localisation to the sites of the ear puncture sites (indicated by diamonds).

FIG. 7 shows cell growth inhibition assays using a variety of targeting antibodies in DU-145 and MDA-MB-231 breast cancer cell lines. Briefly, cells were grown for 3 days in the presence of chimeric MIL-38 and protein G pre-labelled with the cytotoxic agents DM1, MMAE, MMAF and Duocarmycin after which cell viability was assessed. EC50s were determined and are shown to the right of the respective figures. Antibodies used were chimeric MIL-38 (FIG. 7A), BLCA-38 (bi-clonal population containing AM3 and AM4 populations, FIG. 7B), AM3 (monoclonal derived from BLCA-38 population that has minimal GPC-1-binding, FIG. 7C), 1F5 MIL-38 (AM4-like monoclonal derived from BLCA-38 population that has high GPC-1-binding, FIG. 7D) and Erbitux (generic name cetuximab, a chimeric anti-EGFR monoclonal that serves as positive control, FIG. 7E). FIG. 7F shows titration of protein G-duocarmycin in DU-145 cells (top panel) and cell growth inhibition assays using the optimized protein G-duocarmycin concentration in DU-145 cells;

FIG. 8 shows cell growth and chimeric antibody expression characteristics from a pilot batch production using a stable cell pool. Viable cell density (FIG. 8A), cell viability (FIG. 8B) and antibody production (FIG. 8C) are shown, demonstrating scalable chimeric antibody expression using methodologies suitable for large scale GMP production;

FIG. 9 shows DOTA conjugation of MIL-38 and labeling with $^{177}$Lu. FIG. 9A shows gel filtration standard markers run on HPLC. FIG. 9B shows unconjugated MIL-38 run on HPLC. FIG. 9C shows conjugated MIL-38 run on HPLC following PD-10 column purification. FIG. 9D shows radioactivity of MIL-38 labelled with $^{177}$Lu run on HPLC. FIG. 9E shows the corresponding A280 trace of the labelled MIL-38 run on HPLC;

FIG. 10 shows FLOW cytometry of chimeric MIL-38, MIL-38 DOTA and mock radio-labelled MIL-38 DOTA binding to DU-145 cells. Essentially equivalent binding curves were obtained indicating that the DOTA conjugation did not cause a reduction in MIL-38 binding to DU-145 cells. Similarly, MIL-38 DOTA that had undergone a mock radiolabelling process had equivalent cell binding to the un-labelled conjugate, indicating retention of cell binding activity;

FIG. 11 shows labeling of DOTA-conjugated MIL-38 with $^{67}$Ga. FIG. 11A shows a size exclusion chromatography HPLC chromatogram of the radioactivity of MIL-38 labelled with $^{67}$Ga. The star indicates free $^{67}$Ga remaining in the reaction mixture. FIG. 11B shows a stability study of $^{67}$Ga-labelled MIL-38 DOTA. The size exclusion chromatography HPLC chromatogram of the radioactivity of MIL-38 labelled with $^{67}$Ga is shown together with the corresponding UV trace. The $^{67}$Ga-MIL-38 preparation had free $^{67}$Ga removed, then was allowed to remain at room temperature for two weeks prior to undergoing SEC HPLC chromatograph.

FIG. 12 shows binding of chimeric MIL-38, MIL-38 DOTA prepared using three different DOTA conjugate ratios and mock radio-labelled MIL-38 DOTA to DU-145 and T-24 cells using FLOW cytometry, as well as binding in a direct antigen binding ELISA. FIG. 12A shows binding of unlabelled chimeric MIL-38 or chimeric MIL-38 that had been conjugated to DOTA using either a 5, 10 or 20 fold molar excess of DOTA. Essentially equivalent binding curves were obtained indicating that the DOTA conjugation did not cause a reduction in MIL-38 binding to DU-145 cells. FIG. 12B shows FLOW cytometry binding to T-24 cells of three separate batches of chMIL-38 DOTA (20 fold excess) that had each undergone a mock-labelling reaction. Essentially identical binding curves were observed indicating good inter-batch reproducibility. FIG. 12C shows FLOW cytometry binding to T-24 cells of three separate FLOW reactions of chMIL-38 DOTA (20 fold excess) all prepared from one batch that had undergone a mock-labelling reaction. Essentially identical binding curves were observed indicating good intra-batch reproducibility. FIG. 12D shows overlayed FLOW cytometry profiles of binding to T-24 cells for secondary antibody alone (red trace), chMIL-38 DOTA (green trace), one sample from the inter-batch reproducibility (Batch 1, blue trace) and one sample from the intra-batch reproducibility (Intra 1, orange trace). Essentially identical binding curves were observed indicating that the mock-labelling process did not affect binding to cells compared to the chMIL-38 DOTA control. FIG. 12E shows binding of chMIL-38 and chMIL-38 that had been conjugated to DOTA using either a 5, 10 or 20 fold molar excess of DOTA to recombinant GPC-1 in a direct binding ELISA.

FIG. 12F shows direct binding to recombinant GPC-1 of chMIL-38 DOTA, the 3 different preparations of mock-labelled chMIL-38 DOTA prepared for the inter-batch comparison and 3 different reactions from the intra-batch preparation.

FIG. 13 shows (A) fluorescence images observed from the back of Balb/c nude mice with DU-145 xenograft tumours after chimeric MIL-38 antibody injection; and (B) Multimodal Animal Rotation System (MARS) image of a representative mouse from (A) after 144 hours.

FIG. 14 shows a time course of biodistribution of $^{177}$Lu-labelled MIL-38 DOTA when administered to normal rats. The graph shows the % injected dose per gram for blood, stomach, small intestine, large intestine, testes, muscle, bone thyroid, heart, lung, liver, kidneys, and bladder. Timepoints of 6 hr, 1 day, 2 days, 1 week and 2 weeks post administration are shown.

FIG. 15 shows a time course of biodistribution of $^{177}$Lu-labelled MIL-38 DOTA when administered to normal rats. The graph shows the % injected dose per gram for blood, liver and kidneys. Timepoints of 6 hr, 1 day, 2 days, 1 week and 2 weeks post administration are shown.

FIG. 16 is a PET-CT image of $^{64}$Cu-labelled MIL-38 NOTA taken 48 hours post injection in Balb/c nude mice with xenograft tumours. Arrow indicates site of DU-145 xenograft tumour.

FIG. 17 is a graph representing ex vivo biodistribution of DOTA- and NOTA-labelled MIL-38 antibody in Balb/c nude mice with xenograft tumours.

FIG. 18 shows (A) fluorescence images observed from the back for goat anti-GPC-1 antibody; (B) ex vivo fluorescence images of organs observed for goat anti-GPC-1 at 120 hours post injection. Tumours are indicated with red arrows; and (C) MARS image at 120 hrs.

FIG. 19 shows comparative sandwich ELISAs performed using different MIL-38 antibody preparations as capture antibodies. FIG. 19A shows comparative sandwich ELISAs using AM3 and AM4 as capture antibodies. FIG. 19B shows comparative sandwich ELISAs using either a mixed preparation (34A) or a clonal population (AM4 1F5) as capture antibodies.

DEFINITIONS

As used in this application, the singular form "a", "an" and "the" include plural references unless the context clearly dictates otherwise. For example, the phrase "an antibody" also includes multiple antibodies.

As used herein, the term "comprising" means "including." Variations of the word "comprising", such as "comprise" and "comprises," have correspondingly varied meanings. Thus, for example, a sample "comprising" antibody A may consist exclusively of antibody A or may include one or more additional components (e.g. antibody B).

As used herein the term "multiple" means more than one. In certain specific aspects or embodiments, multiple may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

As used herein, the terms "antibody" and "antibodies" include IgG (including IgG1, IgG2, IgG3, and IgG4), IgA (including IgA and IgA2), IgD, IgE, IgM, and IgY, whole antibodies, including single-chain whole antibodies, and antigen-binding fragments thereof. Antigen-binding antibody fragments include, but are not limited to, Fv, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin or appropriate production host. Antigen-binding antibody fragments, including single-chain antibodies, may comprise the variable region/s alone or in combination with the entire or partial of the following: hinge region, CH1, CH2, and CH3 domains. Also included are any combinations of variable region/s and hinge region, CH1, CH2, and CH3 domains. Antibodies may be monoclonal, polyclonal, chimeric, multispecific, humanised, and human monoclonal and polyclonal antibodies which specifically bind the biological molecule. The antibody may be a bi-specific antibody, avibody, diabody, tribody, tetrabody, nanobody, single domain antibody, VHH domain, human antibody, fully humanized antibody, partially humanized antibody, anticalin, adncctin, or affibody.

As used herein the term "monoclonal antibody" refers to an antibody that recognises a single antigenic epitope, and that is obtained from a population of substantially homogeneous antibodies which bind specifically to the same antigenic epitope, and are identical with the potential exception of naturally occurring mutation/s that may be present in minor amounts.

As used herein, the term "humanised antibody" refers to forms of antibodies that contain sequences from human antibodies as well as non-human antibodies (e.g. murine antibodies). For example, a humanised antibody can comprise substantially all of at least one and typically two variable domains, in which all/substantially all of the hypervariable loops correspond to those of a non-human immunoglobulin and all/substantially all of the FR regions are from the human immunoglobulin sequence. The humanised antibody may optionally also comprise at least a portion of an immunoglobulin constant region (Fc) which may typically be that of a human immunoglobulin.

As used herein, the term "chimeric antibody" refers to an antibody which exhibits a desired biological activity, and in which a portion of the light chain and/or heavy chain is identical to or homologous with corresponding sequences in antibodies derived from a given/specific species, while the remaining chain/s is/are identical to or homologous with corresponding sequences in antibodies derived from another different species. For example, a chimeric antibody may comprise variable regions that are derived from a first species and comprise constant regions that are derived from a second species. Chimeric antibodies can be constructed for example by genetic engineering from immunoglobulin gene segments belonging to different species.

As used herein, the term "hybridoma" refers to a cell produced by the fusion of an immortal cell (e.g. a multiple myeloma cell) and an antibody-producing cell (e.g. a B lymphocyte), which is capable of producing monoclonal antibodies of a single binding specificity.

As used herein, the terms "binding specifically" and "specifically binding" in reference to an antibody, antibody variant, antibody derivative, antigen binding fragment, and the like refers to its capacity to bind to a given target molecule preferentially over other non-target molecules. For example, if the antibody, antibody variant, antibody derivative, or antigen binding fragment ("molecule A") is capable of "binding specifically" or "specifically binding" to a given target molecule ("molecule B"), molecule A has the capacity to discriminate between molecule B and any other number of potential alternative binding partners. Accordingly, when exposed to a plurality of different but equally accessible molecules as potential binding partners, molecule A will selectively bind to molecule B and other alternative potential binding partners will remain substantially unbound by molecule A. In general, molecule A will preferentially bind to molecule B at least 10-fold, preferably 50-fold, more preferably 100-fold, and most preferably greater than 100-fold more frequently than other potential binding partners. Molecule A may be capable of binding to molecules that are not molecule B at a weak, yet detectable level. This is commonly known as background binding and is readily discernible from molecule B-specific binding, for example, by use of an appropriate control.

As used herein, the term "cytotoxic agent" encompasses any compound that is toxic to a cell such as, for example by, inhibiting cell function, and including but not limited to, causing cell death directly and/or indirectly.

As used herein, the terms "conjugate", "conjugated" and "conjugation" in the context of a "cytotoxic agent" as described herein and an antibody, antibody derivative, or antigen binding fragment of an antibody described herein will be understood to mean that the cytotoxic agent is linked to the antibody, antibody derivative, or antigen binding fragment. The link may occur directly between the cytotoxic agent and the antibody, or alternatively the link between the cytotoxic agent and the antibody may occur indirect via one or more intervening molecules (e.g. protein-G).

As used herein, the term "subject" includes any animal of economic, social or research importance including bovine, equine, ovine, primate, avian and rodent species. Hence, a "subject" may be a mammal such as, for example, a human or a non-human mammal.

Any description of prior art documents herein, or statements herein derived from or to based on those documents, is not an admission that the documents or derived statements are part of the common general knowledge of the relevant art. For the purposes of description all documents referred to herein are hereby incorporated by reference in their entirety unless otherwise stated.

DETAILED DESCRIPTION

A need continues to exist for more effective methods and agents to treat prostate, bladder, and/or pancreatic cancer. Antibodies are useful diagnostic and therapeutic agents for cancer, having become a successful and important tool for diagnosing and treating patients with haematological malignancies and solid tumours. The identification of new relevant antibodies targeting tumour-specific antigens offers one potential means of improving diagnostic and/or therapeutic outcomes for cancer patients. Another means by which these outcomes can be enhanced is through the improvement of existing antibody-based diagnostics and/or therapies.

The present inventors have surprisingly identified that the BLCA-38 antibody referred to and used in the prior art is not a discrete monoclonal antibody as indicated, but rather a combination of two distinct monoclonal antibodies in a mixed population. The present inventors have determined that the hybridoma used to generate the BLCA-38 antibody, a representative sample of which was deposited at the American Tissue Type Culture Collection under accession number HB11785, is a mixed population of hybridoma cells, which produces at least two discrete antibody species. Only one of these antibody species can bind strongly to the relevant target antigen present on prostate, bladder, and/or pancreatic cancer cells, whilst the second species cannot.

The unexpected determination that BLCA-38 as referred to in the prior art represents a mixed hybridoma/antibody population has facilitated the generation of a monoclonal hybridoma capable of producing a single population of monoclonal antibodies with binding specificity for the target antigen on prostate, bladder, and/or pancreatic cancer cells. This circumvents the unnecessary production and application of an ineffectual therapeutic antibody. It is also well known that the cost of therapeutic antibody production is high, and in particular when post-production modifications are required such as ADC production or conjugation of chelating agents for radio-immunotherapy. It is clearly beneficial to avoid preparing ADC or chelated monoclonal antibodies from antibodies that do not bind the target prostate, bladder, and/or pancreatic cancer cell antigen. The actual target of the antibody species in the BLCA-38 mixed population that does not bind to the prostate, bladder, and/or to pancreatic cancer antigen is unknown raising the risk of unwanted side-effects from potential binding to non-target cells.

The present inventors have also unexpectedly discovered that contrary to prior art teachings that the BLCA-38 antibody population is not internalised on binding to cancer cells, the present inventors have demonstrated that antibodies of the monoclonal antibody species are in fact internalised upon binding to the relevant target antigen present on prostate, bladder, and/or pancreatic cancer cells.

Accordingly, certain embodiments of the present invention relate to the provision of a monoclonal antibody population derived from clonal hybridoma cells, each member of the antibody population being capable of binding specifically to an antigen present on prostate, bladder, and/or pancreatic cancer cells. The present invention also provides antigen binding fragments of these antibodies, as well as derivatives and variants of the antibodies that maintain the same binding specificity. The antibodies and fragments are each conjugated to at least one cytotoxic agent that is toxic to a prostate, bladder, and/or pancreatic cancer cell in the subject.

In view of providing antibody conjugates capable of specifically targeting prostate, bladder, and/or pancreatic cancer cells, other embodiments of the present invention relate to methods for treating prostate, bladder, and/or pancreatic cancer in subjects afflicted with the same, and methods for killing prostate, bladder, and/or pancreatic cells and tumours.

Further aspects of the present invention relate to medicaments and pharmaceutical preparations comprising the conjugated antibodies and/or fragments, and methods for their preparation.

Antibodies and Antigen-Binding Fragments

The present invention provides antibodies, derivatives of such antibodies, and antigen binding fragments thereof, each conjugated to at least one cytotoxic agent.

In alternative embodiments, the antibodies, derivatives of such antibodies, and antigen binding fragments thereof, are provided without being conjugated to at least one cytotoxic agent (i.e. 'naked').

The antibodies, variants, derivatives, and antigen binding fragments are capable of binding specifically to an antigenic epitope present in glypican-1 heparan sulfate proteoglycan (GPC-1). The GPC-1 protein may be a human glypican-1 protein (e.g. as to defined by a sequence set forth in any one of: NCBI reference sequence accession no. NP_002072.2, GenBank accession no. AAH51279.1, GenBank accession no. AAA98132.1, GenBank accession no. EAW71184.1, or UniProtKB/Swiss-Prot accession no. P35052.2). In some embodiments the GPC-1 protein may not include a signal peptide and/or a propeptide. Additionally or alternatively, the monoclonal antibodies, derivatives, and antigen binding fragments may be capable of binding specifically to an antigenic epitope present in a GPC-1 variant (e.g. a GPC-1 isoform, splice variant, or allotype).

By way of non-limiting example, the antibodies, variants, derivatives, and antigen binding fragments may comprise a heavy chain and/or a light chain, combinations thereof, or component/s thereof.

Non-limiting examples of suitable anti-GPC1 antibodies include those set out in Table 1 below.

TABLE 1 non-limiting examples of anti-GPC1 antibodies

| Company | Cat# | Reactivity | Use | Host | M/P | Binding specificity | Immunogen |
|---|---|---|---|---|---|---|---|
| R & D | BAF4519 | Human | WB, FC | Goat | poly | aa24-530 | mouse myeloma cell line NS0-derived recombinant human Glypican-1, Asp24-Ser530 (Accession# P35052) |
| Bioss | bs-2426R-Biotin | Human, mouse, rat, dog, cow, horse | WB, ELISA, IHC-P & F | Rabbit | poly | | Unknown immunogen. Biotin conjugated |
| Bioss | bs-2426-HRP | Human, mouse, rat, dog, cow, horse | WB, ELISA, IHC-P & F | Rabbit | poly | | Unknown immunogen. HRP conjugated |
| antibodies-online | ABIN740102 | Human, mouse, rat, dog, cow, horse | WB, ELISA, IHC-P & F | Rabbit | poly | C-term | Synthetic peptide derived from human glypican 1 C-terminus. Biotin conjugated. |
| antibodies-online | ABIN1174125 | Human | IHC, WB, ELISA | Rabbit | poly | | Unknown immunogen. Biotin conjugated |
| antibodies-online | ABIN740109 | Human, mouse, rat, dog, cow, horse | WB, ELISA, IGC-P & F | Rabbit | poly | C-term | Synthetic peptide derived from human glypican 1 C-terminus. Enquire about sequence info. HRP conjugated |
| antibodies-online | ABIN653109 | Human | WB, IHC, FACS, ELISA | Rabbit | poly | N-term | KLH conjugated synthetic peptide between 12-41aa from the N-terminal region of human Glypican-1 |
| antibodies-online | ABIN952553 | human | ELISA, IHC-p, WB, FACS | Rabbit | poly | N-term | KLH conjugated synthetic peptide between 12-41aa from the N-terminal region of human Glypican-1 |
| antibodies-online | ABIN797896 | human | IHC, WB | Rabbit | poly | N-term | synthetic peptide derived from N-terminal domain of human GPC1 |
| antibodies-online | ABIN347483 | mouse, rat, human | IHC, WB | Rabbit | poly | N-term | synthetic peptide derived from N-terminal domain of human GPC1 |
| antibodies-online | ABIN347484 | human | IHC, WB, ICC, ELISA | Rabbit | poly | N-term | synthetic peptide derived from N-terminal domain of human GPC1 |
| antibodies-online | ABIN740100 | Human, mouse, rat, dog, cow, horse | WB, ELISA, IHC-P & F, IF | Rabbit | poly | C-term | Synthetic peptide derived from human glypican 1 C-terminus. Enquire about sequence info. |
| antibodies-online | ABIN207433 | human | WB, ELISA | Rabbit | poly | C-term | synthetic peptide corresponding to C-terminal residues of human GPC1 precursor |
| antibodies-online | ABIN964659 | human, mouse, rat | WB, ELISA | Rabbit | poly | internal region | synthetic peptide corresponding to an internal region of human GPC-1 |
| antibodies-online | ABIN349638 | human | WB, ELISA | Rabbit | poly | internal region | synthetic peptide corresponding to human GPC1 |
| antibodies-online | ABIN1101824 | human | WB, ELISA | Rabbit | poly | internal poly | synthetic peptide corresponding to an internal region of human GPC-1 |

TABLE 1-continued non-limiting examples of anti-GPC1 antibodies

| Company | Cat# | Reactivity | Use | Host | M/P | Binding specificity | Immunogen |
|---|---|---|---|---|---|---|---|
| antibodies-online | ABIN595376 | human | WB, ELISA | Rabbit | poly | internal region | synthetic peptide corresponding to an internal region of human GPC-1 |
| antibodies-online | ABIN330371 | human | WB, ELISA | goat | poly | aa24-530 | NS0-derived rhGlypican 1 aa24-530 |
| antibodies-online | ABIN1479675 | human | FACS, IHC, WB, ELISA | Rabbit | poly | aa12-41 | KLH conjugated synthetic peptide from N-terminal region of human GPC1 |

The heavy chain or component/s thereof may comprise a heavy chain variable region comprising one, two, or three complementarity determining regions (CDR1, CDR2, and/or CDR3), also known in the art as heavy chain hypervariable (HV) regions. The heavy chain CDR1 may comprise or consist of an amino acid sequence as defined by residues 50-54 of SEQ ID NO: 3. The heavy chain CDR2 may comprise or consist of an amino acid sequence as defined by residues 69-85 of SEQ ID NO: 3. The heavy chain CDR3 may comprise or consist of an amino acid sequence as defined by residues 118-126 of SEQ ID NO: 3.

Additionally or alternatively, the heavy chain variable region may comprise one, two, three, or four framework regions (FR1, FR2, FR3, and/or FR4). The heavy chain FR1 may comprise or consist of an amino acid sequence as defined by residues 20-49 of SEQ ID NO: 3. The heavy chain FR2 may comprise or consist of an amino acid sequence as defined by residues 55-68 of SEQ ID NO: 3. The heavy chain FR3 may comprise or consist of an amino acid sequence as defined by residues 86-117 of SEQ ID NO: 3. The heavy chain FR4 may comprise or consist of an amino acid sequence as defined by residues 127-137 of SEQ ID NO: 3.

Additionally or alternatively, the heavy chain variable region may comprise a leader sequence. The heavy chain leader sequence may comprise or consist of an amino acid sequence as defined by residues 1-19 of SEQ ID NO: 3. The skilled person will recognise that the leader sequence is a signal sequence which facilitates the transport of a newly synthesised heavy chain into the endoplasmic reticulum, and is generally not present in the heavy chain of the final assembled form of the monoclonal antibody.

Additionally or alternatively, the light chain or component/s thereof may comprise a light chain variable region comprising one, two, or three complementarity determining regions (CDR1, CDR2, CDR3) also known in the art as light chain hypervariable (HV) regions. The light chain CDR1 may comprise or consist of an amino acid sequence as defined by residues 44-54 of SEQ ID NO: 4. The light chain CDR2 may comprise or consist of an amino acid sequence as defined by residues 70-76 of SEQ ID NO: 4. The light chain CDR3 may comprise or consist of an amino acid sequence as defined by residues 109-117 of SEQ ID NO: 4.

Additionally or alternatively, the light chain variable region may comprise one, two, three, or four framework regions (FR1, FR2, FR3, FR4). The light chain FR1 may comprise or consist of an amino acid sequence as defined by residues 21-43 of SEQ ID NO: 4. The light chain FR2 may comprise or consist of an amino acid sequence as defined by residues 55-69 of SEQ ID NO: 4. The light chain FR3 may comprise or consist of an amino acid sequence as defined by residues 77-108 of SEQ ID NO: 4. The light chain FR4 may comprise or consist of an amino acid sequence as defined by residues 118-127 of SEQ ID NO: 4.

Additionally or alternatively, the light chain variable region may comprise a leader sequence. The light chain leader sequence may comprise or consist of an amino acid sequence as defined by residues 1-20 of SEQ ID NO: 4. The skilled person will recognise that the leader sequence is a signal sequence which facilitates transport of a newly synthesised light chain into the endoplasmic reticulum, and is generally not present in the light chain of the final assembled form of the monoclonal antibody.

Additionally or alternatively, the heavy chain may comprise one, two, or three heavy chain constant regions. The heavy chain constant region may comprise or consist of an amino acid sequence as defined by residues 138-461 of SEQ ID NO: 3.

Additionally or alternatively, the light chain may comprise a light chain constant region. The light chain constant region may comprise or consist of an amino acid sequence as defined by residues 128-234 of SEQ ID NO: 4.

In some embodiments, monoclonal antibodies, variants, derivatives, and antigen binding fragments according to the present invention may comprise a heavy chain variable region which comprises or consists of an amino acid sequence as defined by residues 20-137 of SEQ ID NO: 3. The monoclonal antibodies, variants, derivatives, and antigen binding fragments may comprise one or two of the heavy chain variable regions.

In some embodiments, monoclonal antibodies, variants, derivatives, and antigen binding fragments according to the present invention may comprise a light chain variable region which comprises or consists of an amino acid sequence as defined by residues 21-127 of SEQ ID NO: 4. The monoclonal antibodies, variants, derivatives, and antigen binding fragments may comprise one or two of the light chain variable regions.

In some embodiments, monoclonal antibodies, variants, derivatives, and antigen binding fragments according to the present invention may comprise a heavy chain variable region which comprises or consists of residues 20-137 of SEQ ID NO: 3, and a light chain variable region which comprises or consists of residues 21-127 of SEQ ID NO: 4. The monoclonal antibodies, variants, derivatives, and antigen binding fragments may comprise a combination of two of the heavy chain variable regions and two of the light chain variable regions.

In some embodiments, monoclonal antibodies, variants, derivatives, and antigen binding fragments according to the present invention may comprise a heavy chain comprising or consisting of an amino acid sequence as defined by residues 20-461 of SEQ ID NO: 3. The monoclonal antibodies, variants, derivatives, and antigen binding fragments may comprise one or two of the heavy chains.

In some embodiments, monoclonal antibodies, variants, derivatives, and antigen binding fragments according to the present invention may comprise a light chain comprising or consisting of an amino acid sequence as defined by residues 21-234 of SEQ ID NO: 4. The monoclonal antibodies, variants, derivatives, and antigen binding fragments may comprise one or two of the light chains.

In some embodiments, monoclonal antibodies, variants, derivatives, and antigen binding fragments according to the present invention may comprise a heavy chain comprising or consisting of an amino acid sequence as defined by residues 20-461 of SEQ ID NO: 3, and a light chain comprising or consisting of an amino acid sequence as defined by residues 21-234 of SEQ ID NO: 4. The monoclonal antibodies, variants, derivatives, and antigen binding fragments may comprise or consist of a combination of two of the heavy chains and two of the light chains.

Monoclonal antibodies, variants and derivatives of such antibodies, and antigen binding fragments thereof according to the present invention are not restricted to any particular isotype, and thus may be IgA (IgA1 or IgA2), IgD, IgE, IgG (IgG1, IgG2, IgG3, IgG4), or IgM isotype. In some embodiments, they are IgG1 isotype.

Included within the scope of the present invention are monoclonal antibodies produced by hybridoma cells submitted under the terms of the Budapest Treaty at Cellbank Australia at 214 Hawkesbury Road, Westmead NSW 2145, Australia on 22 Aug. 2014 under accession number CBA20140026. The hybridoma is a clonal population that produces a single antibody species having binding specific for an epitope existing in glypican-1 heparan sulfate proteoglycan (GPC-1).

Included within the scope of the present invention are "fragments" of the antibodies described herein. In general, the fragments are "antigen binding fragments" in the sense that they are capable of specifically binding to same antigen/epitope (e.g. GPC-1) as the parent antibody from which they are derived or upon which they are based. Typically, an antigen binding fragment retains at least 10% of the antigen/epitope binding capacity of the parent antibody, or, at least 25%, 50%, 60%, 70%, 80%, 90%, 95%, 99% or 100% (or more) of the antigen/epitope binding capacity of the parent antibody. It is also contemplated that an antigen binding fragment of an antibody described herein may include conservative amino acid substitutions that do not substantially alter its antigen/epitope binding specificity/capacity (e.g. at least 70%, 80%, 90%, 95%, 99% or 100% (or more) of its antigen/epitope binding specificity/capacity may be retained).

Non-limiting examples of antigen binding fragments include portions of a full length antibody, peptides and derivatives thereof including, for example, Fab, Fab', F(ab)$_2$, F(ab)$_2$, F(ab)$_3$, Fv, single-chain Fv (scFv), dsFv, Fd fragments, dAB fragments Fse, VH, VL, VhH, and V-NAR domains, paratopes, CDR regions, single-chain antibody molecules (e.g. sc-Fv), minibodies, diabodies, triabodies, tetrabodies, kappa bodies, linear antibodies, multispecific antibodies, domain antibodies formed from antibody fragments, multispecific antibody fragments formed from antibody fragments, and any portion or peptide sequence of the antibody that is capable of specifically binding to the relevant antigen/epitope (e.g. GPC-1).

Also included within the scope of the present invention are "derivatives" of the antibodies described herein. A "derivative" of an antibody of the present invention refers to an antibody described herein that is modified to incorporate additional components or have existing component/s altered, but is still capable of specifically binding to the same antigen/epitope (e.g. GPC-1) as the parent antibody from which it is derived. Typically, an antibody derivative as contemplated herein retains at least 10% of the antigen/epitope binding capacity of the parent antibody, or, at least 25%, 50%, 60%, 70%, 80%, 90%, 95%, 99% or 100% (or more) of the antigen/epitope binding capacity of the parent antibody.

Non-limiting examples of modifications suitable to form antibody derivatives include amidation, glycosylation, phosphorylation, pegylation, linkage to a cellular ligand or other protein, derivatisation by known protecting/blocking groups, acetylation, and the like. Additionally or alternatively, the derivative may contain one or more non-classical amino acids. Modifications may also include conjugation with a chelating agent such as DOTA, DTPA, NOTA, NODAGA, MeCOSAR, TETA, TRAP, TE2A, and CBTE2A.

The antibody derivatives may include labelled antibodies such as, for example, monoclonal antibodies labelled with radioactive iodine, indium, sulphur, carbon, tritium or the like; monoclonal antibodies conjugated with avidin or biotin, monoclonal antibodies conjugated with enzymes (e.g. horseradish, glucose 6-phosphate dehydrogenase glucose oxidase, beta-D-galactosidase, alkaline phosphatase, glucoamylase, acetylcholine esterase, carboxylic acid anhydrase, malate dehydrogenase, lysozyme, or peroxidase), and monoclonal antibodies conjugated with chemiluminescent agents (e.g. acridine esters), bioluminescent agents (e.g. luciferase), or fluorescent agents (e.g. phycobiliproteins). Further examples of antibody derivatives include bifunctional antibodies, such as bispecific antibodies generated by combining parts of two separate antibodies that recognize two different antigenic groups (e.g. by recombinant techniques or crosslinking).

The antibody derivatives may be formed from covalent modification of the antibodies described herein, for example, by reacting targeted amino acid residues of the antibody with an agent capable of reacting with selected side chains or terminal residues. For example, derivatisation with bifunctional agents is a useful means for cross-linking an antibody or fragment thereof to macromolecular carriers such as water-insoluble support matrices. Antibody derivatives as contemplated herein may have an agent attached to a base antibody or a fragment thereof capable of increasing its half-life in vivo (e.g. extending the length of time before clearance from the blood stream). A non-limiting example of such a technique includes addition of PEG moieties.

In certain embodiments, the antibody derivative may be a multimer, such as, for example, a dimer, comprising one or more monomers, where each monomer includes (i) an antigen-binding region of an anti-GPC-1 antibody as described herein, or a polypeptide region derived therefrom (such as, for example, by conservative substitution of one or more amino acid/s), and (ii) a multimerising (e.g. dimerising) polypeptide region, such that the antibody derivative forms multimers (e.g. homodimers) that specifically bind to GPC-1. For example, an antigen binding region of an anti-GPC-1 antibody as described herein, or a polypeptide region derived therefrom, may be recombinantly or chemically fused with a heterologous protein, wherein the heterologous protein comprises a dimerisation or multimerisation domain. The derivative may be subjected to conditions allowing formation of a homodimer or heterodimer. The heterodimer may comprise identical dimerisation domains but different anti-GPC-1 antigen-binding regions, identical anti-GPC-1 antigen-binding regions but different dimerisation domains, or different anti-GPC-1 antigen-binding regions and different dimerisation domains. Suitable dimerisation domains include those that originate from transcription factors (e.g. a basic region leucine zipper), a basic-region helix-loop-helix protein, and an immunoglobulin constant region (e.g. a heavy chain constant region or a domain thereof such as a CH1 domain, a CH2 domain, or a CH3 domain).

In other embodiments, the antibody derivative may be an anti-GPC1 antibody as described herein conjugated to a second antibody (an "antibody heteroconjugate").

Also contemplated herein are humanised derivatives of the antibodies described herein. A "humanised" antibody as contemplated herein is a human/non-human chimeric antibody that contains a minimal sequence derived from non-human immunoglobulin. For example, a humanised antibody may be a human immunoglobulin (recipient antibody) in which residues from CDR region/s of the recipient are replaced by residues from a CDR region of a non-human species (donor antibody) (e.g. a mouse, rat, rabbit, or non-human primate having the desired specificity and affinity for a GPC-1 antigen/epitope). Framework region (FR) residues of the human immunoglobulin may also (optionally) be replaced by corresponding non-human residues, and in some cases humanised antibodies may comprise residues not present in the recipient antibody or in the donor antibody to enhance antibody performance.

Further contemplated herein are "chimeric" antibody derivatives in which a portion of the heavy and/or light chain is identical with or homologous to corresponding sequences of an antibody described herein derived from a particular species or belonging to a particular antibody class or subclass, while the remainder of the chain/s is/are identical with or homologous to corresponding sequences in antibodies derived from another different species or belonging to another different antibody class or subclass. For example, a chimeric antibody as contemplated herein may comprise variable regions derived from an anti-GPC-1 monoclonal antibody as described herein, and constant regions derived from a second species. Chimeric antibodies may be generated, for example, by genetic engineering of immunoglobulin gene segments belonging to different species. The chimeric antibodies and antigen-binding fragments thereof may or may not be conjugated to a cytotoxic agent as described herein.

By way of non-limiting example only, a chimeric antibody according to the present invention may comprise a chimeric Mouse Human CH1-CH3 Chain Sequence Mouse VH-Human CH1-CH3 Chain (heavy chain) and/or a Mouse Human Kappa Chain Sequence Mouse VK-Human CK sequence MIL-38 Mouse VK (light chain). The heavy chain of the chimeric antibody may comprise or consist of an amino acid sequence as set out in residues 20-467 of SEQ ID NO: 7. The light chain of the chimeric antibody may comprise or consist of an amino acid sequence as set out in residues 21-234 of SEQ ID NO: 8. The heavy chain variable region may comprise: a complementarity determining region 1 (CDR1) comprising or consisting of an amino acid sequence defined by positions 50-54 of SEQ ID NO: 7; and/or a complementarity determining region 2 (CDR2) comprising or consisting of an amino acid sequence defined by positions 69-85 of SEQ ID NO: 7; and/or a complementarity determining region 3 (CDR3) comprising or consisting of an amino acid sequence defined by positions 118-126 of SEQ ID NO: 7. Additionally or alternatively, the light chain variable region may comprise: a complementarity determining region 1 (CDR1) comprising or consisting of an amino acid sequence defined by positions 44-54 of SEQ ID NO: 8; and/or a complementarity determining region 2 (CDR2) comprising or consisting of an amino acid sequence defined by positions 70-76 of SEQ ID NO: 8; and/or a complementarity determining region 3 (CDR3) comprising or consisting of an amino acid sequence defined by positions 109-117 of SEQ ID NO: 8. A chimeric antibody according to the present invention may be a "variant" of this chimeric antibody.

Included within the scope of the present invention are "variants" of the antibodies described herein. A "variant" antibody refers to an antibody which differs in amino acid sequence from a "parent" anti-GPC-1 antibody amino acid sequence by virtue of addition, deletion, and/or substitution of one or more amino acid residue/s in the parent antibody sequence. For example, the variant antibody may comprise one or more amino acid substitution/s in one or more CDR and/or framework region/s of the parent antibody (e.g. between 1 and 10, between 2 and 5, or 1, 2, 3, 4, or 5 substitutions in one or more heavy and/or light chain CDR and/or framework regions of the parent antibody). The antibody variant may comprise a heavy chain variable domain sequence and/or a light chain variable domain sequence amino acid sequence having at least 50%, at least 60%, at least 70%, at least 80%, at least 85%, at least 90%, at least 95%, or at least 98% amino acid sequence homology (i.e. sequence identity) with the corresponding variable domain of the parent antibody.

Sequence homology or identity between two sequences is defined herein as the percentage of amino acid residues in the candidate sequence that are identical with the parent antibody residues, after aligning the sequences and introducing gaps, if necessary, to achieve the maximum percent sequence identity. If the two sequences which are to be compared with each other differ in length, sequence identity relates to the percentage of amino acid residues of the shorter sequence which are identical with the amino acid residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711) and/or the program "fasta20u66" (version 2.0u66, September 1998 by William R. Pearson and the University of Virginia; see also W. R. Pearson (1990), Methods in Enzymology 183, 63-98).

In some embodiments, a variant antibody as described herein may differ from a parent antibody by way of conservative amino acid change/s in the sequence of the variable antibody. A "conservative change" refers to an alteration that is substantially antigenically or conformationally neutral, producing minimal changes in the tertiary structure of the variant antibody, or producing minimal changes in the antigenic determinants of the variant antibody, as compared to the parent antibody, and one which does not render the derivative incapable of binding to the same epitope in GPC-1 as the parent antibody. Non-limiting examples of conservative amino acid changes include substitution of hydrophobic amino acids and substitution of physicochemically similar amino acids. Persons of ordinary skill in the art can routinely and without difficulty assess whether a given amino acid substitution can be made while maintaining conformational and antigenic neutrality (see, for example, Berzofsky, (1985) Science 229:932-940; Bowie et al. (1990) Science 247:1306-1310). Alterations in protein conformation may be achieved using well-known assays including, but not limited to, microcomplement fixation methods (see Wasserman et al. (1961) J. Immunol. 87:290-295; Levine et al. (1967) Meth. Enzymol. 11:928-936) and through binding studies using conformation-dependent monoclonal antibodies (see Lewis et al. (1983) Biochem. 22:948-954). The conservative amino acid change/s may occur in one or more CDR and/or framework region/s of the parent antibody (e.g. between 1 and 10, between 2 and 5, or 1, 2, 3, 4, or 5 conservative substitutions in one or more CDR and/or framework regions of the parent antibody).

In general, humanised, chimeric, derivative, fragment and variant antibodies as contemplated herein are still capable of specifically binding to same antigen/epitope (e.g. GPC-1) as the parent antibody from which they derive or which they contain component/s of. Typically, they may retain at least 10% of the antigen/epitope binding capacity of the parent antibody, or, at least 25%, 50%, 60%, 70%, 80%, 90%, 95%, 99% or 100% (or more) of the antigen/epitope binding capacity of the parent antibody. For example, they may have a stronger binding affinity and/or binding specificity compared to the parent antibody.

The capacity of an antibody fragment, derivative, or variant to bind specifically to an antigen/epitope that is targeted by the parent antibody (i.e. a GPC-1 antigen/epitope) can be tested using known methods in the art including, for example, competitive and non-competitive assay systems using techniques such as Western blots, radioimmunoassays, enzyme linked immunosorbent assay (ELISA), immunoprecipitation assays, "sandwich" immunoassays, immunodiffusion assays, precipitin reactions, protein A immunoassays, fluorescent immunoassays, gel diffusion precipitin reactions, complement-fixation assays, immunoradiometric assays, agglutination assays, and the like (see, for example, Ausubel et al., eds., *Short Protocols in Molecular Biology* (John Wiley & Sons, Inc., New York, 4th ed. 1999); Harlow & Lane, *Using Antibodies. A Laboratory Manual* (Cold Spring Harbor Laboratory Press, Cold Spring Harbor, N.Y., 1999)).

Specifically included within the scope of the present invention are variants of any antibody or antigen binding fragment thereof described herein including, but not limited to, antibodies (including chimeric antibodies) and antigen binding fragments defined by specific sequences herein, and antibodies produced by hybridomas described herein including the hybridoma submitted under the terms of the Budapest Treaty at Cellbank Australia at 214 Hawkesbury Road, Westmead NSW 2145, Australia on 22 Aug. 2014 under accession number CBA20140026.

Cytotoxic Agents

Antibodies and antibody-binding fragments thereof according to the present invention may be conjugated to at least one cytotoxic agent. The cytotoxic agent may be any compound that is toxic to a cell (e.g. a prostate, bladder, and/or pancreatic cancer cell) such as, for example by, inhibiting cell function, and including but not limited to, causing cell death directly and/or indirectly.

Cytotoxic agents may cause direct toxicity to the prostate, bladder, and/or pancreatic cancer cell, or may induce apopotosis. Alternatively, in the case of a radiolabel, the radiation may cause DNA damage resulting in cell growth arrest, apoptosis induction or cell death.

Enhanced prostate, bladder, and/or pancreatic cancer death may result from immune recognition of proteins from dead or dying prostate, bladder, and/or pancreatic cancer cells thereby resulting in an "immunisation" effect.

Non-limiting examples of suitable cytotoxic agents include: afatinib, aplidin, anastrozole, anthracyclines, AVL-101, AVL-291, axitinib, azaribine, bendamustine, bleomycin, bortezomib, bosutinib, bryostatin-1, busulfan, camptothecans, carboplatin, calicheamycin, camptothecin, carboplatin, carmustine, celecoxib, chlorambucil, cisplatinum, cladribine, COX-2 inhibitors, crizotinib, cyano-morpholino doxorubicin, cyclophosphamide, cytarabine, dacarbazine, dactinomycin, dasatinib, daunorubicin, dinaciclib, 3',5'-0-dioleoyl-FudR (FUdR-d0), DM1, DM3, DM4, docetaxel, doxorubicin, doxorubicin glucuronide, duocarmycin, endostatin, entinostat, epidophyllotoxin, epirubicin glucuronide, erlotinib, estramustine, estrogen receptor binding agents, etoposide glucuronide, etoposide phosphate, etoposide (VP16), exemestane, famesyl-protein transferase inhibitors, fingolimod, flavopiridol, floxuridine (FUdR), fludarabine, 5-fluorouracil, flutamide, fostamatinib, ganetespib, GDC-0834, gefitinib, gemcitabine, GS-1101, 10-hydroxycamptothecin, hydroxyurea, ibrutinib, idarubicin, idelalisib, ifosfamide, imatinib, irinotecan (CPT-11), lapatinib, lenolidamide, leucovorin, LFM-A13, lomustine, mechlorethamine, melphalan, mercaptopurine, 6-mercaptopurine, methotrexate, mithramycin, mitomycin, mitotane, mitoxantrone, monomethylauristatin D (MMAD), monomethylauristatin E (MMAE), monomethylauristatin F (MMAF), navelbine, neratinib, nilotinib, nitrosurea, olaparib, so paclitaxel, PCI-32765, pentostatin, plicomycin, a 2-PDox pro-drug (pro-2-PDox), procarbazine, PSI-341, 2-pyrrolinodoxorubicine (2-PDox), raloxifene, semustine, SN-38, sorafenib, streptozocin, SU1 1248, sunitinib, tamoxifen, temazolomide, teniposide, thalidomide, thioguanine, thiotepa, topotecan, transplatinum, uracil mustard, vatalanib, vinblastine, vinca alkaloids, vincristine, vinorelbine, and ZD 1839.

Additionally or alternatively, the cytotoxic agent may be a radioisotope. Non-limiting examples of suitable radioisotopes include: $^{90}Y$, $^{188}Re$, $^{166}Ho$, $^{165}Dy$, $^{109}Pd$, $^{111}Ag$, $^{186}Re$, $^{198}Au$, $^{153}Sm$, $^{64}Cu$, $^{177}Lu$, $^{131}I$, $^{125}I$, $^{67}Cu$, $^{175}Yb$, $^{166}Dy$, $^{169}Er$, $^{212}Bi$, $^{213}Bi$, $^{225}Ac$, $^{212}Pb$, $^{66}Ga$, $^{67}Ga$, $^{68}Ga$, $^{86}Y$, $^{94m}Tc$, and $^{89}Zr$.

In some embodiments, the antibody or antigen-binding fragment thereof is conjugated to the cytotoxic agent or agent(s) directly.

In other embodiments the antibody or antigen-binding fragment thereof is conjugated to the cytotoxic agent or agent(s) indirectly (e.g. via a chelating agent selected from the group consisting of: DOTA, DTPA, NOTA, NODAGA, MeCOSAR, TETA, TRAP, TF2A, CBTE2A).

Conjugated Antibody Production

Processes for the preparation of the monoclonal antibodies, derivatives and variants thereof, and antigen binding fragments thereof are readily available and capable of being performed without difficulty by persons of ordinary skill in the art.

Apart from the hybridoma method of Kohler et al. (1975) and described above in the section entitled "Hybridomas", another non-limiting process that may be utilised is recombinant DNA technology (see, for example, U.S. Pat. No. 4,816,567). For example, the monoclonal antibodies, derivatives and variants thereof, and antigen binding fragments thereof, may be recombinantly produced in any well-established expression system including, but not limited to, baculovirus, yeast (e.g. *Pichia* sp., *Saccharomyces* sp.) *E. coli*, mammalian cells, plants, or transgenic animals (see Breitling and Dubel, 1999, Recombinant Antibodies, John Wiley & Sons, Inc., NY, pp. 119-132).

In some embodiments, nucleic acid sequences encoding monoclonal antibodies, derivatives and variants thereof, and antigen binding fragments thereof in accordance with the present invention may be used in production processes based on recombinant DNA technologies. Non-limiting examples include a heavy chain polynucleotide sequence as defined in SEQ ID NO: 1 or a variant or fragment thereof, and/or a light chain polynucleotide sequence as defined in SEQ ID NO: 2 or a variant or fragment thereof.

A "variant" polynucleotide refers herein to a polynucleotide which differs in sequence from a parent or reference polynucleotide. Polynucleotide sequence divergence may result from mutational changes such as deletions, substitutions, or additions of one or more nucleotides. Each of these changes may occur alone or in combination, one or more times in a given sequence. A "variant" polynucleotide refers to a polynucleotide that has a substantially similar sequence to a parent or reference polynucleotide. In general, two sequences are "substantially similar" if the two sequences have a specified percentage of nucleotides that are the same (percentage of sequence "homology" or sequence "identity"). Sequence homology or identity between two polynucleotide sequences is defined herein as the percentage of nucleotides in the candidate ("variant") sequence that are identical with those of the parent/reference polynucleotide sequence, after aligning the sequences and introducing gaps, if necessary, to achieve the maximum percent sequence identity. If the two sequences which are to be compared with each other differ in length, sequence identity relates to the percentage of the nucleotides of the shorter sequence which are identical with the nucleotides of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711) and/or the program "fasta20u66" (version 2.0u66, September 1998 by William R. Pearson and the University of Virginia; see also W. R. Pearson (1990), Methods in Enzymology 183, 63-98). The degree of sequence homology/identity between the variant polynucleotide and the reference/parent polynucleotide may, for example, be at least 75%, 80%, 83% 85%, 88%, 90%, 93%, 95%, 96%, 97%, 98% or 99%.

A polynucleotide "fragment" is a polynucleotide molecule that encodes a constituent or is a constituent of a large parent/reference polynucleotide. In general, the fragment will encode a fragment of an antibody of the present invention, the fragment being capable of specifically binding to GPC-1.

Monoclonal antibodies, derivatives and variants thereof, and antigen binding fragments thereof produced in accordance with the present invention may be isolated from various sources using appropriate methods including, but not limited to, immunoglobulin-binding molecules (for example, proteins A, L, G or H), tags operatively linked to the antibody or antibody fragment (for example, His-tag, c-myc tag), affinity chromatography, and the like.

Monoclonal antibodies, derivatives and variants thereof, and antigen binding fragments thereof as described herein may be produced by hybridomas and/or cell cultures comprising single or mixed populations of hybridomas including, for example, those described in the section above entitled "Hybridomas", then isolated using known techniques. In some embodiments, the monoclonal antibodies can be produced by culturing a single (monoclonal) species of hybridoma cells deposited under the terms of the Budapest Treaty at Cellbank Australia under accession number CBA20140026, and isolated from the culture.

Processes for the preparation and cultivation of the hybridoma cell lines and isolation of the antibody produced are well known to those of ordinary skill in the art and are standard procedures.

Antibodies and antibody-binding fragments thereof according to the present invention may be conjugated to at least one cytotoxic agent. Methods for conjugating cytotoxic agents to antibodies and antigen binding fragments thereof are well known to those skilled in the art (see, for example, Zhang et al. PLOS One December 2011, Volume 6 Issue 12).

Medicaments and Pharmaceutical Formulations

Medicaments and pharmaceutical formulations according to the present invention comprise antibodies and antibody-binding fragments thereof, which may be conjugated to at least one cytotoxic agent, as described herein, or alternatively be provided without such agent(s) (i.e. naked). The medicaments and pharmaceutical formulations may be prepared using methods known to those of ordinary skill in the art. Non-limiting examples of suitable methods are described in Gennaro et al. (Eds), (1990), "*Remington's Pharmaceutical Sciences*", Mack Publishing Co., Easton, Pa., USA.

The medicaments and pharmaceutical formulations may comprise a pharmaceutically acceptable carrier, excipient, diluent and/or adjuvant. "Pharmaceutically acceptable" carriers, excipients, diluents and/or adjuvants as contemplated herein are substances which do not produce adverse reaction(s) when administered to a particular recipient such as a human or non-human animal. Pharmaceutically acceptable carriers, excipients, diluents and adjuvants are generally also compatible with other ingredients of the medicaments and pharmaceutical formulations. Non-limiting examples of suitable excipients, diluents, and carriers can be found in the "*Handbook of Pharmaceutical Excipients*" 4th Edition, (2003) Rowe et al. (Eds), The Pharmaceutical Press, London, American Pharmaceutical Association, Washington.

Non-limiting examples of pharmaceutically acceptable carriers, excipients or diluents include demineralised or distilled water; saline solution; vegetable based oils such as peanut oil, safflower oil, olive oil, cottonseed oil, maize oil, sesame oils, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Medicaments and pharmaceutical formulations of the present invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, intradermal, subcutaneous, intramuscular or intravenous injection.

Solid forms of the medicaments and pharmaceutical formulations for oral administration may contain binders acceptable in human and veterinary pharmaceutical practice, sweeteners, disintegrating agents, diluents, flavouringscoating agents, preservatives, lubricants and/or time delay agents. Suitable binders include gum acacia, gelatine, corn, starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms of the medicaments and pharmaceutical formulations for oral administration may contain, in addition to the above agents, a liquid carrier. Suitable liquid carriers include water, oils such as olive oil, peanut oil, sesame oil, sunflower oil, safflower oil, *arachis* oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

For preparation of the medicaments and pharmaceutical formulations as injectable solutions or suspensions, non-toxic parenterally acceptable diluents or carriers may be used such as Ringer's solution, isotonic saline, phosphate buffered saline, ethanol and 1,2 propylene glycol.

Emulsions for oral administration may further comprise one or more emulsifying agents. Suitable emulsifying agents include dispersing agents as exemplified above or natural gums such as guar gum, gum acacia or gum tragacanth.

Topical formulations comprise an active ingredient(s) (e.g. i.e. antibodies and/or antigen-binding fragments thereof of the present invention) together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

When formulated as drops, the medicaments and pharmaceutical formulations may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. For example, sterilisation may be achieved by filtration followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

When formulated as creams, ointments or pastes, the medicaments and pharmaceutical formulations may be semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives, or a fatty acid such as stearic or oleic acid together with an alcohol such as propylene glycol or macrogols.

The medicaments and pharmaceutical formulations may include any suitable surfactant such as an anionic, cationic or non-ionic surfactant such as sorbitan esters or polyoxyethylene derivatives thereof. Suspending agents such as natural gums, cellulose derivatives or inorganic materials such as siliceous silicas, and other ingredients such as lanolin, may also be included.

Methods for Treating Prostate, Bladder, and/or Pancreatic Cancer

According to the present invention, antibodies and antibody-binding fragments thereof, which may be naked or conjugated to at least one cytotoxic agent, are suitable for the treatment of prostate, bladder, and/or pancreatic cancer. The antibodies and/or fragments thereof may be administered as components of pharmaceutical formulations or medicaments as are described herein.

The identification of subjects with or at risk of developing prostate, bladder, and/or pancreatic cancer is well known to those of ordinary skill in the art. For example, in the case of prostate cancer suitable methodologies include, but are not limited to, digital rectal exam, PSA-based assays, and prostate biopsy.

One of the distinguishing factors between benign prostate tumors (non cancerous) and malignant prostate tumors (cancerous) is the ability of the cancerous form to metastasise. Metastasis is the capacity for cancerous cells to spread (metastasise) to other parts of the body. Prostate cancer in patients is further categorised into stages according to the TNM Classification of Malignant Tumours (TN M), which categorises cancer based on the size and extent of the primary tumor (T), the spread of the cancer to nearby lymph nodes (N), and the presence of secondary tumor formed by the metastasis (M) of the primary tumor to other parts of the body (American Cancer Society). Table 2 shows example definitions for each cancer stage.

TABLE 2

Definitions for cancer stages of the TNM system, adapted from the American Cancer Society.

| Stage | Definition |
| --- | --- |
| Stage 0 | Carcinoma in situ |
| Stage I, Stage II, and Stage III | Higher numbers indicate more extensive disease: Larger tumor size and/or spread of the cancer beyond the organ in which it first developed to nearby lymph nodes and/or tissues or organs adjacent to the location of the primary tumor |
| Stage IV | The cancer has spread to distant tissues or organs |

The methods may be used for treating prostate, bladder, and/or pancreatic cancer in a subject. Non-limiting examples of prostate cancers that may be treated with the present invention include prostatic intraepithelial neoplasia, adenocarcinoma, leiomyosarcoma, and rhabdomyosarcoma. Non-limiting examples of bladder and/or pancreatic cancer that may be treated with the present invention include T categories for bladder cancer, N categories, and M categories, as defined in the American Joint Committee on Cancer (AJCC) 'TNM system', muscle invasive bladder cancer, and non-muscle invasive bladder cancer.

It will be under stood that "treating" within the context of the methods described herein refers to the alleviation, in whole or in part, of symptoms associated with prostate, bladder, and/or pancreatic cancer, or slowing, inhibiting or halting of further progression or worsening of those symptoms, or the prevention of prostate, bladder, and/or pancreatic cancer. Accordingly, treating prostate, bladder, and/or pancreatic cancer may include, for example, inhibiting or preventing the metastasis of the cancer, a reduction in the speed and/or number of the metastasis, a reduction in tumour volume of the metastasised prostate, bladder, and/or pancreatic cancer, a complete or partial remission of the metastasised prostate, bladder, and/or pancreatic cancer, or other therapeutic benefit(s).

The subject may be any animal that can benefit from the administration of the antibodies and/or antibody-binding fragments thereof. In some embodiments, the subject is a mammal, for example, a human, a dog, a cat, a horse, a cow, a pig, a primate, or a rodent (e.g. a rat or mouse).

The methods may involve the administration of a "therapeutically effective amount" of antibodies and antibody-binding fragments thereof according to the invention. A "therapeutically effective amount" will be understood to refer to an amount of the antibodies and/or fragments that alleviates, in whole or in part, symptoms associated with prostate, bladder, and/or pancreatic cancer, or slows, inhibits or halts further progression or worsening of those symptoms, or prevents or provides prophylaxis for prostate, bladder, and/or pancreatic cancer in a subject at risk for developing prostate cancer.

The therapeutically effective amount may vary depending upon the route of administration and dosage form. Effective amounts of conjugated antibodies and/or fragments thereof according to the present invention typically fall in the range of about 0.001 up to 100 mg/kg/day, for example in the range of about 0.05 up to 10 mg/kg/day. Typically, the antibodies and/or fragments are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Generally, an effective dosage of conjugated antibodies and/or fragments thereof according to the present invention is expected to be in the range of about 0.0001 mg to about 1000 mg of active component(s) (i.e. of conjugated antibodies and/or fragments thereof according to the present invention) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m² of active component(s) (i.e. of conjugated antibodies and/or fragments thereof according to the present invention). Generally, an effective dosage is expected to be in the range of about 25 to about 500 mg/m², preferably about 25 to about 350 mg/m², more preferably about 25 to about 300 mg/m², still more preferably about 25 to about 250 mg/m², even more preferably about 50 to about 250 mg/m², and still even more preferably about 75 to about 150 mg/m².

Typically, in therapeutic applications, the treatment would be for the duration of prostate, bladder, and/or pancreatic cancer disease in the subject. Further, it will be apparent to one of ordinary skill in the art that the optimal quantity and spacing of individual dosages will be determined by the nature and extent of the prostate, bladder, and/or pancreatic cancer being treated, the form, route and site of administration, and the nature of the particular individual being treated. Also, such optimum conditions can be determined by conventional techniques.

In many instances, it will be desirable to have several or multiple administrations of conjugated antibodies and/or fragments thereof according to the present invention. For example, a given dosage may be administered 1, 2, 3, 4, 5, 6, 7, 8, 9, 10, or more times. The administrations may be from about one to about twelve week intervals, and in certain embodiments from about one to about four week intervals. Periodic re-administration may be desirable in the case or risk of recurrent occurrence of prostate, bladder, and/or pancreatic cancer in a given subject.

It will also be apparent to one of ordinary skill in the art that the optimal course of treatment can be ascertained using conventional course of treatment determination tests.

The conjugated antibodies and/or fragments thereof according to the present invention can be formulated for various routes of administration, for example, by oral, parenteral (e.g. intradermal, intravenous, intraspinal, intraperitoneal, subcutaneous or intramuscular), nasal, rectal, topical, or by way of an implanted reservoir. Systemic or parenteral administration includes, but is not limited to, intraperitoneal, intramuscular, subcutaneous, and intravenous injections. In one embodiment, they are administered by a mucosal route. Non-limiting examples of acceptable routes of mucosal administration including intranasal, ocular, buccal, genital tract, rectal, intratracheal, skin, and the gastrointestinal tract.

In some embodiments, the treatment methods described herein antibodies and/or fragments thereof may be administered in combination with other agents or therapies. The antibodies and/or fragments thereof may be components of pharmaceutical formulations or medicaments as are described herein. Non-limiting examples of the additional agents or therapies include hormonal agents, LHRH agonists and antagnoists, CYP17 inhibitors, taxane therapy, radioisotope treatment, immunomodulatory therapy. Examples include docetaxel, mitoxantrone, abiraterone acetate, enzalutamide, ketoconazole, corticosteroids, Sipuleucel-T, cabazitaxel, $^{223}$radium, gemcitabine and Bacille Camlette Guerin (BCG) immunotherapy. Additional radiation therapies also used include external beam radiation and brachytherapy. The antibodies and/or fragments thereof may be administered to the subject simultaneously with the additional agents or therapies. Additionally or alternatively, the antibodies and/or fragments may be administered to the subject before or after the additional agents or therapies are administered.

EXAMPLES

The present invention will now be described with reference to specific examples, which should not be construed as in any way limiting.

Example 1: Analysis of Antibodies from MIL-38 Hybridoma Populations 1.1 Materials and Methods MIL-38 Antibody Preparation Preparations MIL-38 antibody hybridoma were obtained from the following sources:

(i) In house cell stocks of the BLCA-38 hybridoma were used to generate MIL-38 antibody preparations designated 33A.

(ii) An early passage (<6) freezedown of cells from the original deposit of the BLCA-38 hybridoma (HB11785) was used to perform single cell cloning and provide a number of clones to characterize. The MIL-38 1F5 clone was selected and deposited at CellBank Australia under deposit number CBA20140026.

(iii) The hybridoma stock used as a basis to generate the preparations described in (i) and (ii) above was prepared as described in U.S. Pat. No. 5,622,8361 to Walker et al., the entire contents of which are incorporated herein by cross-reference.

For purification of MIL-38 antibody, frozen cell stocks were quickly thawed followed by resuspension in RPMI 1640 medium and allowed to grow at 37° C. with 5% $CO_2$ for 24 hours. Cells were expanded, split and scaled up in a sequential process. At each step, cells were resuspended in fresh medium and incubated at 37° C. with 5% $CO_2$. After scale up, cells were transferred to sterile serum free medium and grown till the start of death phase. The supernatant was harvested to collect the MIL-38 antibody and filter sterilised. Antibody supernatant was stored at −80° C. until required. Antibody was purified using Pierce protein G according to the manufacturer's recommendations.

Western Blot and Sypro Gel Analysis

Protein extraction: DU-145 (MIL-38 antigen positive) or C3 (MIL-38 antigen negative) cells were cultured according to standard tissue culture techniques. Cell membrane proteins were enriched using the Merck Millipore ProteoExtract Native Membrane Protein Extraction Kit (MPEK) according to the manufacturer's instructions.

Transfer

Gels were transferred onto a nitrocellulose membrane for 10 min at 2.5 A and 25V maximum using the Transblot Turbo system (Biorad).

Western Blot

Briefly, after transfer membranes were blocked with 5% skim milk in PBS-Tween (0.1%) for 2 h at room temperature. Primary antibodies (1 μg/ml in 5% skim milk—PBS-Tween (0.1%)) were applied and incubated overnight at 4° C. After washing (3×10 min PBS-Tween (0.1%)) membranes were incubated with secondary antibody (1:2000 sheep-anti-mouse HRP-labelled in 5% skim milk—PBS-Tween (0.1%)). After washing (3×10 min PBS-Tween (0.1%)) antigen was detected by using ECL detection kit (Biorad) and imaging with LAS4000 mini (GE Life Science).

Sypro Gels

Gels were fixed in fixing solution (10% Ethanol, 7% acetic acid) for 2 h before being transferred into Sypro® Ruby Protein Stain and incubated overnight at room temperature in the dark. Before imaging gels were rinsed and washed with destaining solution (10% Ethanol, 7% acetic acid) for a minimum of 2 h. Imaging was performed with a Pharos X Scanner.

Immunofluorescence assay (IFA)

IFA: Cells were grown on coverslips until 75% confluent and placed in 6 well plates. The cells were washed with PBS followed by fixing with acetone. Cells were washed again with PBS followed by incubation with TBS then blocked with PBS containing 5% skim milk. Cells were then incubated in the dark with MIL-38, chimeric MIL-38 or Cetuximab followed by incubation with a Goat anti-mouse or Goat anti-human antibody labelled with FITC or Alexa488. Both antibodies were prepared in PBS containing 1% skim milk followed. Washing with PBS was performed between the primary and secondary antibody incubations. After secondary incubation, cells were washed with PBS containing DAPI and visualised for green fluorescence (MIL-38 positive).

SDS-PAGE Electrophoresis

SDS-PAGE: Samples were mixed with non-reducing SDS-containing sample buffer and loaded onto a 4-15% precast polyacrylamide gel (Criterion TGX; Biorad). Gels were run for 10 min at 80V and additional 50 min at 200V in Tris-Glycine running buffer.

Sequencing (DNA)

Previous results indicated that the BLCA-38 cells deposited at ATCC accession number HB11785 contained two populations of cells. Subcloning identified two types of clones: AM3/Alfio II type (did not bind GPC-1) or AM4/Alfio 1 (bound GPC-1 strongly). The two populations were sequenced together with a low passage stock obtained from ATCC (termed "1-0 or original").

For sequencing runs 224945 (1-O) and 449295-1 (Alfio I), total RNA was extracted from frozen hybridoma cells and cDNA was synthesized from the RNA. PCR was then performed to amplify the variable regions (heavy and light chains) and constant regions of the antibody, which were then cloned into a standard cloning vector separately and sequenced. Total RNA was isolated from the hybridoma cells following the technical manual of TRizol® Plus RNA Purification System. The total RNA was analysed by agarose gel electrophoresis. Total RNA was reverse transcribed into cDNA using isotype-specific anti-sense primers or universal primers following the technical manual of SuperScript™ III First-Strand Synthesis System. The antibody fragments of VH, VL, CH and CL were amplified according to the standard operating procedure of RACE of GenScript. Amplified antibody fragments were separately cloned into a standard cloning vector using standard molecular cloning procedures. Colony PCR screening was performed to identify clones with inserts of correct sizes. No less than five single colonies with inserts of correct sizes were sequenced for each antibody fragment. VH and VL plasmids encoded the full-length variable regions of the antibody and a part of CH1 and CL. CH plasmid encoded a part of CH1 and full-length CH2 and CH3. CL plasmid encoded a part of CL. In order to get full-length constant regions or heavy/light chain, the part of constant regions encoded by VH and VL plasmids and the part of constant regions encoded by CH and CL plasmids were amplified by PCR separately, and then overlap extension PCR was employed to obtain full-length DNAs. Five single colonies with correct VH, VL, CH and CL insert sizes were sent for sequencing. The isolated total RNA of the sample was run alongside a DNA marker (Marker III—TIANGEN, Cat. No.: MD103) on a 1.5% agarose/GelRed™ gel. Four microliters of PCR products of each sample were run alongside the DNA marker (Marker 111) on a 1.5% agarose/GelRed™ gel. The PCR products were purified and stored at −20° C. until further use.

The $V_H$, $V_L$, $C_H$ and $C_L$ genes of five different clones were nearly identical. The consensus sequence, listed below, was determined to be the sequence of the antibody produced by the monoclonal hybridoma population (AM-4).

MIL-38 Mouse IgG1 Heavy Chain DNA Consensus Sequence (SEQ ID NO: 1)

ATGGCTTGGGTGTGGACCTTGCTATTCCTGATGGCTGCTGCCCAAAGTATCCAAGCA

CAGATCCAGTTGGTGCAGTCTGGACCTGAGCTGAAGAAGCCTGGAGAGACAGT

CAAGATCTCCTGCAAGGCTTCTGGTTATGCCTTCACAGACTATTCAATGAACTGGG

TGAAGCAGGCTCCAGGAAAGGGTTTAAGGTGGATGGGCTGGATAAACACTGAGA

CTGGTGAGCCAACATATACAGATGACTTCAAGGGACGGTTTGCCTTCTCTTTGGAAA

CCTCTGCCAGCACTGCCTTTTTGCAGATCAACAACCTCAGAAATGAAGACACGG

CTACATATTTCTGTGCTAGACACTATGATTACGGGGGGTTTCCTTACTGGGGCCAA

GGGACTCTGGTCACTGTCTCTGCAGCCAAAACGACACCCCATCTGTCTATCCACT

GGCCCCTGGATCTGCTGCCCAAACTAACTCCATGGTGACCCTGGGATGCCTGGTCAA

GGGCTATTTCCCTGAGCCAGTGACAGTGACCTGGAACTCTGGATCCCTGTCCAGCGG

TGTGCACACCTTCCCAGCTGTCCTGCAGTCTGACCTCTACACTCTGAGCAGCTCAGTG

ACTGTCCCCTCCAGCACCTGGCCCAGCGAGACCGTCACCTGCAACGTTGCCCACCC

GGCCAGCAGCACCAAGGTGGACAAGAAAATT GTGCCCAGGGATTGTGGTTGTAAGC

CTTGCATATGTACA GTCCCAGAAGTATCATCTGTCTTCATCTTCCCCCCAAAGCCCAA

GGATGTGCTCACCATTACTCTGACTCCTAAGGTCACGTGTGTTGTGGTAGACATCAGC

AAGGATGATCCCGAGGTCCAGTTCAGCTGGTTTGTAGATGATGTGGAGGTGCACACA

GCTCAGACGCAACCCCGGGAGGAGCAGTTCAACAGCACTTTCCGCTCAGTCAGTGAA

CTTCCCATCATGCACCAGGACTGGCTCAATGGCAAGGAGTTCAAATGCAGGGTCAAC

AGTGCAGCTTTCCCTGCCCCCATCGAGAAAACCATCTCCAAAACCAAAGGCAGACCG

AAGGCTCCACAGGTGTACACCATTCCACCTCCCAAGGAGCAGATGGCCAAGGATAAA

GTCAGTCTGACCTGCATGATAACAGACTTCTTCCCTGAAGACATTACTGTGGAGTGGC

AGTGGAATGGGCAGCCAGCGGAGAACTACAAGAACACTCAGCCCATCATGGACACAG

ATGGCTCTTACTTCGTCTACAGCAAGCTCAATGTGCAGAAGAGCAACTGGGAGGCAG

GAAATACTTTCACCTGCTCTGTGTTACATGAGGGCCTGCACAACCACCATACTGAGAA

GAGCCTCTCCCACTCTCCTGGTAAATGA

Individual regions of mouse heavy chain encoded sequence are indicated with alternating italics. Positions 1-57 = leader sequence, 58-147 = framework region (HFR1); 148-162 = complementary determining region (HCDR1); 163-204 = HFR2; 205-255 = HCDR2; 256-351 = HFR3; 352-378 = HCDR3; 379-411 = HFR4; 412-1383 = constant regions (CH1-CH3); 703-741 = hinge region (bolded); 1384-1386 = stop codon.

MIL-38 Mouse Kappa Light Chain DNA Consensus Sequence (SEQ ID NO: 2)

ATGAGTGTGCTCACTCAGGTCCTGGCGTTGCTGCTGCTGTGGCTTACAGGTGCCAGA

TGTGACATCCAGATGACTCAGTCTCCAGCCTCCCTATCTGCATCTGTGGGAGAAA

CTGTCACCATCACATGTCGAGCAAGTGGGAATGTTCACAATTATTTAGCATGGTATC

AGCAGAAACAGGGAAAATCTCCTCAACTCCTGGTCTATACTGCAAAAACCTTAGC

AGATGGTGTGCCATCAAGGTTCAGTGGCAGTGGATCAGGAACACAATATTCTCTC

AAGATCAATAGCCTGCAGCCTGAAGATTTTGGGACTTATTACTGTCAACATTTTTG

-continued
```
GAGTAATCCGTGGACGTTCGGTGGAGGCACCAAGCTGGAAATCAAACGGGCTGAT

GCTGCACCAACTGTATCCATCTTCCCACCATCCAGTGAGCAGTTAACATCTGGAGGTG

CCTCAGTCGTGTGCTTCTTGAACAACTTCTACCCCAAAGACATCAATGTCAAGTGGAA

GATTGATGGCAGTGAACGACAAAATGGCGTCCTGAACAGTTGGACTGATCAGGACAG

CAAAGACAGCACCTACAGCATGAGCAGCACCCTCACGTTGACCAAGGACGAGTATGA

ACGACATAACAGCTATACCTGTGAGGCCACTCACAAGACATCAACTTCACCCATTGTC

AAGAGCTTCAACAGGAATGAGTGTTAG
```

Individual regions of mouse light chain encoded sequence are with alternating italics. Positions: 1-60 = leader sequence; 61-129 = framework region (LFR1); 130-162 = complementarity determining region (LCDR1); 163-207 = LFR2; 208-228 = LCDR2; 229-324 = LFR3; 325-351 = LCDR3; 352-381 LFR4; 382-702 = constant regions (CK); 703-705 = stop codon.

The heavy and light chain AM-4 MIL-38 consensus DNA sequences above translate to the following heavy chain and light chain amino acid sequences:

AM-4 MIL-38 Mouse IgG1 Heavy Chain Amino Acid Consensus Sequence
(SEQ ID NO: 3)
*MAWVWTLLFLMAAAQSIQAQIQLVQSGPELKKPGETVKISCKASGYAF*

TDYSMNWVKQAPGKGLRWMGWINTETGEPTYTDDFKGRFAFSLETSAS

*TAFLQINNLRNEDTATYFCAR*HYDYGGFPYWGQGTLVTVSAA*KTTPPS*

*VYPLAPGSAAQTNSMVTLGCLVKGYFPEPVTVTWNSGSLSSGVHTFPA*

*VLQSDLYTLSSSVTVPSSTWPSETVTCNVAHPASSTKVDKKI*

VPRDCGCKPCICT *VPEVSSVFIFPPKPKDVLTITLTPKVTCVV*

*VDISKDDPEVQFSWFVDDVEVHTAQTQPREEQFNSTFRSVSELPIMHQ*

*DWLNGKEFKCRVNSAAFPAPIEKTISKTKGRPKAPQVYTIPPPKEQMA*

*KDKVSLTCMITDFFPEDITVEWQWNGQPAENYKNTQPIMDTDGSYFVY*

*SKLNVQKSNWEAGNTFTCSVLHEGLHNHHTEKSLSHSPGK*]*

Individual regions of mouse IgG1 heavy chain sequence are indicated in the amino acid sequence above. Positions 1-19 = leader sequence; 20-49 = framework region (HFR1); 50-54 = complementarity determining region 1 (HCDR1); 55-68 = HFR2; 69-85 = HCDR2; 86-117 = HFR3; 118-126 = HCDR3; 127-137 = HFR4 (also called the joining region or J-region); 138-61 = IgG1 chain constant regions (CH1-CH3) & stop codon (*). Hinge region is bolded in the sequence above.

AM-4 consensus MIL-38 Light Chain Amino Acid Consensus Sequence
(SEQ ID NO: 4)
*MSVLTQVLALLLLWLTGARC*DIQMTQSPASLSASVGETVTITC*RASGN*

*VHNYLAWYQQKQGKSPQLLVY*TAKTLADGVPSRFSGSGSGTQYSLKIN

SLQPEDFGTYYC*QHFWSNPWT*FGGGTKLEIK*RADAAPTVSIFPPSSEQ*

*LTSGGASVVCFLNNFYPKDINVKWKIDGSERQNGVLNSWTDQDSKDST*

*YSMSSTLTLTKDEYERHNSYTCEATHKTSTSPIVKSFNRNEC**

Individual regions of light chain amino acid sequence are indicated by alternating italics: Positions 1-20 = Leader sequence; 21-43 = framework region (LFR1); 44-54 = complementarity -continued
determining region 1 (LCDR1); 55-69 = LFR2; 70-76 = LCDR2; 77-108 = LFR3; 109-117 = LCDR3; 118-127 = LFR4; 128-234 = kappa constant region (CK) & stop codon (*)

Example 2: Preparation and Testing of Chimeric MIL-38 Antibodies 2.1 Materials and Methods
Preparation of Chimeric Antibodies
Two optimised cDNA sequences were developed for cloning purposes. These were based on the AM-4 Heavy chain and Light chain consensus sequences identified above in Example 1.

The first optimised cDNA sequence was used in the generation of a mouse-human chimeric heavy chain sequence:

CHO codon Optimized cDNA Sequence #1 - mouse-human chimeric heavy chain 1404 bp
(SEQ ID NO: 5)
```
ATGGCTTGGGTGTGGACACTGCTGTTCCTGATGGCTGCTGCCCAGAGT

ATTCAGGCTCAGATTCAGCTGGTCCAGAGCGGTCCCGAGCTGAAGAAG

CCAGGCGAGACCGTGAAGATCTCCTGCAAGGCCAGCGGCTACGCTTTC

ACAGACTATTCTATGAACTGGGTGAAGCAGGCCCCAGGCAAGGGCCTG

AGGTGGATGGGCTGGATCAATACCGAGACAGGCGAGCCCACCTACACA

GACGATTTCAAGGGCCGGTTCGCTTTTTCCCTGGAGACCTCTGCCTCC

ACAGCTTTTCTGCAGATCAACAATCTGAGAAACGAGGACACCGCCACA

TACTTCTGCGCTAGG*CACTACGATTATGGCGGCTTTCCTTATTGGGGC*

CAGGGCACCCTGGTGACAGTGTCCAGCGCCTCTACCAAGGGCCCATCC

GTGTTTCCACTGGCTCCCTCTTCCAAGAGCACCTCTGGCGGCACAGCC

GCTCTGGGCTGTCTGGTGAAGGATTACTTCCCAGAGCCCGTGACAGTG

TCTTGGAACTCCGGCGCCCTGACCTCCGGAGTGCATACATTTCCCGCT

GTGCTGCAGAGCTCTGGCCTGTACAGCCTGTCCAGCGTGGTGACCGTG

CCTTCTTCCAGCCTGGGCACCCAGACATATATCTGCAACGTGAATCAC

AAGCCATCCAATACAAAGGTGGACAAGAAGGTG GAGCCCAAGAG

CTGTGATAAGACCCATACATGCCCCCCTTGTCCT GCTCCAGAGCT
```

-continued
*GCTGGGAGGACCTAGCGTGTTCCTGTTTCCACCCAAGCCTAAGGACAC*

CCTGATGATCTCTAGGACCCCCGAGGTGACATGCGTGGTGGTGGACGT

*GTCCCACGAGGATCCTGAGGTGAAGTTCAACTGGTACGTGGATGGCGT*

GGAGGTGCATAATGCTAAGACCAAGCCTAGGGAGGAGCAGTACAACAG

*CACCTATCGGGTGGTGTCTGTGCTGACAGTGCTGCACCAGGACTGGCT*

GAACGGCAAGGAGTATAAGTGCAAGGTGAGCAATAAGGCCCTGCCCGC

*TCCTATCGAGAAGACCATCTCTAAGGCCAAGGGCCAGCCTCGGGAGCC*

ACAGGTGTACACACTGCCTCCAAGCAGAGACGAGCTGACCAAGAACCA

*GGTGTCTCTGACATGTCTGGTGAAGGGCTTCTATCCTTCTGATATCGC*

TGTGGAGTGGGAGTCCAATGGCCAGCCAGAGAACAATTACAAGACCAC

*ACCCCCTGTGCTGGACAGCGATGGCTCTTTCTTTCTGTATTCCAAGCT*

GACCGTGGATAAGAGCAGGTGGCAGCAGGGCAACGTGTTCTCCTGTAG

*CGTGATGCACGAGGCACTGCACAACCACTACACTCAGAAATCCCTGTC*

CCTGTCACCTGGCAAATGA

Individual regions of mouse-human chimeric heavy
chain encoded sequence are indicated with alter-
nating italics. Positions: 1-57 = leader
sequence; 58-147 = framework region (FR1); 148-
162 = complementarity determining region (CDR1);
163-204 = FR2; 205-255 = CDR2; 256-351 = FR3;
352-378 = CDR3; 379-411 = FR4; 412-1401 = human
constant regions (CH1-CH3); 706-750 = hinge
region (bolded); 1402-1405 = stop codon.

The second optimised cDNA sequence generated was used in the generation of a mouse-human chimeric light chain sequence:

CHO Codon Optimized cDNA Sequence #2 - mouse-
human chimeric light chain 705 bp
(SEQ ID NO: 6)
ATGAGCGTGCTGACCCAGGTGCTGGCCCTGCTGCTGCTGTGGCTGACC

*GGAGCCCGTTGCGACATCCAGATGACCCAGTCCCCTGCCTCTCTGTCC*

GCCAGCGTGGGCGAGACCGTGACAATCACCTGCAGAGCCTCTGGCAAC

*GTGCACAATTACCTGGCTTGGTATCAGCAGAAGCAGGGCAAGTCCCCA*

CAGCTGCTGGTGTACACAGCCAAGACCCTGGCTGACGGCGTGCCCAGC

*AGGTTCTCTGGCTCCGGCAGCGGCACACAGTATAGCCTGAAGATCAAC*

TCTCTGCAGCCTGAGGATTTTGGCACCTACTATTGCCAGCATTTCTGG

*TCTAATCCATGGACATTTGGCGGCGGCACCAAGCTGGAGATCAAGAGG*

ACAGTGGCCGCTCCCTCCGTGTTCATCTTTCCCCCTAGCGACGAGCAG

*CTGAAGTCTGGCACCGCTTCCGTGGTGTGCCTGCTGAACAATTTCTAC*

CCTCGGGAGGCCAAGGTGCAGTGGAAGGTGGATAACGCTCTGCAGTCT

*GGCAATTCCCAGGAGAGCGTGACAGAGCAGGACTCTAAGGATTCCACC*

TATAGCCTGTCCAGCACACTGACCCTGTCCAAGGCCGACTACGAGAAG

-continued
*CACAAGGTGTATGCTTGTGAGGTCACTCACCAGGGGCTGTCAAGTCCA*

GTCACAAAGTCCTTCAATAGGGGGGAATGCTGA

Individual regions of mouse-human chimeric light
chain encoded sequence are indicated with alter-
nating italics. Positions: 1-60 = leader
sequence; 61-129 = framework region (LFR1);
130-162 = complementarity determining region
(LCDR1); 163-207 = LFR2; 208-228 = LCDR2; 229-
324 = LFR3; 325-351 = LCDR3; 352-381 = LFR4;
382-702 = human constant region (CK); 703-705 =
stop codon.

Chimeric MIL-38 Mouse Human CH1-CH3 chains were transiently expressed in suspension CHO-3E7 cells using serum free medium, followed by one-step purification.

CHO-3E7 cells were grown in serum free FreeStyle™ CHO Expression Medium (Life Technologies, Carlsbad, Calif., USA). The cells were maintained in Erlenmeyer Flasks (Corning Inc., Acton, Mass.) at 37° C. with 5% $CO_2$ on an orbital shaker (VWR Scientific, Chester, Pa.). On the day of transfection, DNA and PEI (Polysciences, Eppelheim, Germany) were mixed at an optimal ratio and then added into the flask with cells ready for transfection. The supernatant collected on day 6 was used for further purification.

Cell culture broth was centrifuged and followed by filtration. Filtered supernatant was loaded onto a 5 ml Protein A CIP column (GenScript, Cat. No. L00433) at 3.0 ml/min. After washing and elution with appropriate buffer, the fractions were collected and neutralized with IM Tris-HCl, pH 9.0. The purified protein was analyzed by SDS-PAGE, Western blot by using standard protocols for molecular weight, yield and purity measurements.

Chimeric MIL-38 Antibody Assays (Slide Immunofluorescence)

The MIL-38 chimeric antibody was used in immunofluorescence assays with DU-145 cells. The murine MIL-38 prep 33A was used as a positive control for GPC-1 antigen staining, while Cetuximab (a chimeric antibody targeting the EGFR) was used as a positive control for staining of human IgG constant regions. A slide with no primary antibody was used as a negative control. Staining was performed essentially as described in Section 1.1 with the exceptions that secondary antibodies were labelled with Alexafluor 488 and that anti-human antibodies were used to stain the chimeric and cetuximab samples.

Chimeric MIL-38 Western Blots

The reactivity of the chimeric MIL-38 and murine MIL-38 towards DU-145 and C3 MPEK extracts as well as to recombinant NS0-produced GPC-1 antigen was tested by Western blot. Western blots were probed either by murine MIL-38 or chimeric MIL-38. Chimeric MIL-38 was detected by goat anti-human secondary antibody followed by a sheep-anti-goat HRP antibody. As a control, murine MIL-38 was detected by goat anti-mouse secondary antibody followed by a sheep-anti-goat HRP antibody. Equivalent reactivity was observed for chimeric MIL-38 and murine MIL-38 when detected under equivalent conditions.

2.2 Results

Expression of Chimeric Antibody Sequences

The recombinant plasmids encoding heavy chain and light chain of Chimeric MIL-38 Mouse Human CH1-CH3 Chain were transiently transfected into suspension CHO-3E7 cell cultures. The target protein was captured from the cell culture supernatant by Protein A CIP 5 ml column and followed by buffer exchange. The purified protein was analyzed by SDS-PAGE and Western blot.

Chimeric Antibody Sequences

Optimised cDNA sequence #1 (SEQ ID NO: 5) was used to generate a chimeric MIL-38 antibody heavy chain with the following amino acid sequence:

```
Chimeric MIL-38 Mouse Human CH1-CH3 Chain
Sequence Mouse VH-Human CH1-CH3 Chain (heavy
chain)
                                      (SEQ ID NO: 7)
MAWVWTLLFLMAAAQSIQAQIQLVQSGPELKKPGETVKISCKASGYAF

TDYSMNWVKQAPGKGLRWMGWINTETGEPTYTDDFKGRFAFSLETSAS

TAFLQINNLRNEDTATYFCARHYDYGGFPYWGQGTLVTVSSASTKGPS

VFPLAPSSKSTSGGTAALGCLVKDYFPEPVTVSWNSGALTSGVHTFPA

VLQSSGLYSLSSVVTVPSSSLGTQTYICNVNHKPSNTKVDKKV

EPKSCDKTHTCPPCP APELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK*

Individual regions of mouse-human chimeric heavy
chain sequence are indicated with alternating
italics in the amino acid sequence above:
Positions 1-19 = leader sequence; 20-49 = frame-
work region (HFR1); 50-54 = complementarity
determining region 1 (HCDR1); 55-68 = HFR2; 69-
85 = HCDR2; 86-117 = HFR3; 118-126 = HCDR3; 127-
137 = HFR4 (also called the joining region or J-
region); 138-467 = IgG1 chain constant regions
(CH1-CH3), & stop codon (*).
Hinge sequence-human IgG1 heavy chain hinge
sequence is bolded above.
```

Optimised cDNA sequence #2 (SEQ ID NO: 6) was used to generate a chimeric MIL-38 antibody light chain with the following amino acid sequence:

```
Chimeric MIL-38 Mouse-Human Kappa Light Chain
Sequence: Mouse VK-Human CK sequence
                                      (SEQ ID NO: 8)
MSVLTQVLALLLLWLTGARCDIQMTQSPASLSASVGETVTITCRASGN

VHNYLAWYQQKQGKSPQLLVYTAKTLADGVPSRFSGSGSGTQYSLKIN

SLQPEDFGTYYCQHFWSNPWTFGGGTKLEIKRTVAAPSVFIFPPSDEQ

LKSGTASVVCLLNNFYPREAKVQWKVDNALQSGNSQESVTEQDSKDST

YSLSSTLTLSKADYEKHKVYACEVTHQGLSSPVTKSFNRGEC*

Individual regions of mouse-human chimeric light
chain amino acid sequence are indicated with
alternating italics: Positions 1-20 = Leader
sequence; 21-43 = framework region (LFR1);
44-54 = complementarity determining region 1
(LCDR1); 55-69 = LFR2; 70-76 = LCDR2; 77-108 =
LFR3; 109-117 = LCDR3; 118-127 = LFR4; 128-234 =
kappa constant region (CK) & stop codon (*)
```

Chimeric MIL-38 Antibody Assays (Slide Immunofluorescence)

FIGS. 1A-D show bright field images of cells. FIG. 1E shows staining of the 33A positive control. FIG. 1F shows staining of the chimeric MIL-38 antibody. FIG. 1G shows staining of using a commercial chimeric (mouse/human) monoclonal antibody (Cetuximab) positive control, and FIG. 1H shows the no primary antibody negative control staining. Strong staining was observed in FIGS. 1E, F and G and no staining was observed in FIG. 1H. These results demonstrate that the chimeric MIL-38 antibody successfully binds DU-145 cells in IFA, indicating that the binding specificity of the parental murine MIL-38 antibody has been maintained.

Chimeric MIL-38 Antibody Assays (Western Blots)

FIG. 2A shows a western blot probed with murine MIL-38, followed by anti-mouse HRP secondary antibody. Exposure time for the Western blot shown in FIG. 2A was 30 seconds. FIG. 2B shows a western blot probed with chimeric MIL-38, followed by goat anti-human secondary antibody. The complex was detected using a sheep-anti-goat HRP antibody. Exposure time for the Western blot shown in FIG. 2R was 30 minutes. FIG. 2C shows a western blot probed with murine MIL-38, followed by goat anti-mouse antibody. The complex was detected using a sheep-anti-goat HRP antibody. Exposure time for the Western blot shown in FIG. 2C was 30 minutes.

The murine MIL-38 anti-mouse recognises the antigen in DU-145 lysates and recombinant GPC-1 NS0. Reactivity was not observed in C3 lysates as expected (FIG. 2A).

A three-antibody detection method was required to test reactivity of the chimeric MIL-38 with DU-145 and C3 extracts as well as recombinant NS0 GPC-1 (FIG. 2B). A control western blot using a three antibody detection method was also performed with murine MIL-38 (FIG. 2C). When a three antibody detection method was used, detection was far less sensitive than using the standard two antibody method (for the Western blots shown in FIGS. 2A and C, exposure time used for FIG. 2A was 30 seconds, whereas that used for FIG. 2C was 30 minutes).

As shown in FIG. 2B, the Chimeric MIL-38 recognises the recombinant GPC-1 NS0 antigen and shows comparable reactivity to murine MIL-38 when detected using this method (compare FIGS. 2B and C).

2.3 Discussion

The Chimeric MIL-38 antibody was successfully expressed and purified in suspension CHO-3E7 cells. The H and L chains of target antibody were detected with estimated molecular weights of ~55 kDa (Cal.M.W. ~52 kDa) and 28 kDa (Cal.M.W. ~26 kDa) based on SDS-PAGE and Western blot analysis.

Equivalent reactivity between the chimeric MIL-38 and the murine parent was observed in IFA and western blotting, indicating that binding specificity has been maintained in the construction of the chimeric antibody.

Example 3: Preparation and Single Chain Variable Fragment (scFv) MIL-38 Antibody 3.1 Materials and Methods Preparation of scFv antibody An optimised cDNA sequence was developed for cloning purposes. This was based on the AM-4 Heavy chain and Light chain consensus sequences identified above in Example 1. The heavy chain variable region was positioned at the N-terminus and linked to the light chain variable region using a flexible to serine/glycine linker. The scFv protein incorporated a C-terminal tag consisting of six histidines (hexa his) to facilitate purification of the recombinant protein and a C-terminus cysteine residue to facilitate Cys-based labeling.

An optimised cDNA sequence was used to generate a mouse-human chimeric heavy chain amino acid sequence:

```
scFv MIL-38 amino acid sequence
                                    (SEQ ID NO: 9)
MGWSCIILFLVATATGVHSQIQLVQSGPELKKPGETVKISCKASGYAF

TDYSMNWVKQAPGKGLRWMGWINTETGEPTYTDDFKGRFAFSLETSAS

TAFLQINNLRNEDTATYFCARHYDYGGFPYWGQGTLVTVSS

GGGGSGGGGSGGGGS DIQMTQSPASLSASVGETVTITCRAS

GNVHNYLAWYQQKQGKSPQLLVYTAKTLADGVPSRFSGSGSGTQYSLK

INSLQPEDFGTYYCQHFWSNPWTFGGGTKLEIKHHHHHHC*

Individual regions of mouse-human chimeric heavy
chain sequence are indicated with alternating
italics in the amino acid sequence above:
Positions 1-19 = leader sequence; 20-49 = frame-
work region (HFR1); 50-54 = complementarity
determining region 1 (HCDR1); 55-68 = HFR2;
69-85 = HCDR2; 86-117 = HFR3; 118-126 = HCDR3;
127-137 = HFR4 (also called the joining region or
J-region); 138-152 = gly/ser flexible linker
sequence, 153-175 = framework region (LFR1);
176-186 = complementarity determining region 1
(LCDR1); 187-201 = LFR2; 202-208 = LCDR2; 209-
240 = LFR3; 241-249 = LCDR3; 250-259 = LFR4;
260-265 = Hexa His tag & stop codon (*).
Linker sequence - Gly/ser linker sequence is
bolded above.
```

ScFv MIL-38 was transiently expressed in CHO cells followed by one-step purification utilizing the hexa-histidine tag and a nickel affinity column.

FLOW Cytometry

Murine 1F5 MIL-38 antibody or the scFv MIL-38 construct were labelled with CY5 fluorophor using standard methods. These antibodies were then used to stain DU-145 prostate cancer cells.

Briefly, DU-145 cells were detached using PBS/2 mM EDTA. Following centrifugation, cells were incubated with antibodies or control solutions in FACS wash solution (PBS/5% fetal calf serum) on ice for 45 min. Following washing with FACS wash solution, cells were resuspended in PBS then assessed for cell binding using FLOW cytometry.

To examine the specificity of binding, DU-145 cells were pre-incubated with unlabelled murine MIL-38 antibody prior to incubation with CY5-labelled MIL-38.

FIG. 3A shows FLOW histograms of DU-145 cells alone or with a CY5-labelled isotype control. FIG. 3B show FLOW histograms of DU-145 cells that were either untreated or labelled with either CY5-labelled MIL-38, or cells that had been pre-incubated with unlabelled MIL-38 prior to incubation with CY5-labelled MIL-38. Specificity of binding is indicated by the lower fluorescence intensity seen for the cells pre-incubated with CY5-labelled MIL-38. FIG. 3C show FLOW histograms of DU-145 cells that were either untreated or labelled with either CY5-labelled MIL-38, or CY5-labelled scFv MIL-38.

3.3 Discussion

The MIL-38 antibody was successfully converted to an scFv format. Binding to DU-145 cells was lower than the parent MIL-38 murine antibody.

Example 4: Internalisation of Murine 1F5 MIL-38 and Chimeric MIL-38 Antibody in DU-145 Prostate Cancer Cells 4.1 Materials and Methods FLOW Cytometry of MDA-MB-231, T-24, PANC-1 or DU-145 Cells Cells were detached with PBS-EDTA then incubated with MIL-38 primary antibody on ice for 45 min in FACS wash buffer (PBS +5% FCS). Cells were washed three times in FACS wash buffer then incubated with AlexaFluor 488 secondary antibody for 30 min on ice in the dark. Following washing 3 times with FACS wash buffer cells were transferred to FACS tubes and assayed using FLOW cytometry.

Antibody Internalisation Assay

MDA-MB-231 or DU-145 cells were seeded in 8-well chamber slides (5) and grown for 24 hours in media containing 10% FCS. Cells were changed to serum free medium for 36 hours. Slides were put on ice, the medium was removed and 200 µL of 10 ug/mL of cold antibody solution in serum free medium were added per well. Cells were incubated for 30 minutes on ice, then washed once with cold serum free medium, 200 µL of serum free medium were added per well, and cells were incubated at 37° C., 5% $CO_2$ for 0, 5, 15 and 30 min. The medium was then removed and cells were fixed with 3% PFA in PBS for 15 min at room temperature. After fixation, cells were washed once with PBS and permeabilised with cold Triton X-100 0.1% in PBS for 5 min. Cells were then washed with PBS to remove excess of detergent, and then blocked with 5% skim milk in Tris Buffered Saline (TBS, pH 7.5) for 30 min. The corresponding secondary antibody (goat anti-mouse-Alexa488 and goat anti-human-Alexa488) was diluted (4 µg/mL and 2 g/mL respectively) in PBS. 200 uL/well to the secondary antibody solution was added per well, and incubated for 45 min at room temperature in the dark. Cells were washed once with PBS, then incubated with 200 µL per well of 1 µg/mL Hoechst (nuclear counterstaining) for 5 minutes, then washed twice with PBS. Chambers were removed, and slides were mounted using 70% glycerol in water as mounting media.

For T-24 cells, cells were seeded in 8-well chamber slides and grown for 3 days, until they reached about 50% confluency. Cells were incubated for 72 hours in serum free medium. Slides were then processed as described above for MDA-MB-231 and DU-145 cells.

For the PANC-1 timecourse, cells were treated as described above for DU-145 cells. Duplicate slides were made, and the cells fixed following 15 min or 60 min at 37° C.

4.2 Results

FIG. 4A shows FLOW cytometry histograms for MDA-MB-231 and controls (no primary antibody or isotype only), while FIG. 4B shows relative reactivity of the 1F5 MIL-38 murine antibody to MDA-MB-231, T-24 or DU-145 cells. FIG. 4C shows reactivity of the 1F5 MIL-38 murine antibody to PANC-1 cells.

FIG. 5A shows localization of the murine MIL-38 antibody (green) following 30 min of incubation with DU-145 cells. Cell nuclei are shown in blue. FIG. 5B shows localization of the chimeric MIL-38 antibody (green) following 30 min of incubation with DU-145 cells. Cell nuclei are shown in blue. FIG. 5C shows lack of binding or internalisation of chimeric MIL-38 following 30 min of incubation with MDA-MB-231 cells. FIG. 5D shows localization of the chimeric MIL-38 antibody (green) immediately following incubation with T-24 cells. Cell nuclei are shown in blue.

FIG. 5E shows localization of chimeric MIL-38 antibody (green) in PANC-1 cells after 15 minutes during a 60 minute timecourse. FIG. 5F shows internalization of anti-human antibody labelled with Alexa-Fluor 488 in PANC-1 cells after completion of the 60 minute timecourse.

4.3 Discussion

MIL-38 antibodies bind to the GPC-1 heparan sulfate proteoglycan antigen (FIGS. 1 and 2). GPC-1 is expressed on the surface of prostate cancer cells (FIG. 1) and has also been reported to be expressed on a variety of other cancer cell lines including ovary and bladder (Walker et al 1989, Russell et al 2004) and breast (Matsuda et al 2001). GPC-1 has also been reported to internalise and recycle to the cell surface via caveolae and endosomal trafficking in T-24 bladder cancer cells (Mani et al 2006).

GPC-1 may therefore be able to transport bound MIL-38 antibodies into the cell via these trafficking mechanisms to enable delivery of toxic moieties such as drugs or radionuclides. The target of the BLCA-38 antibody has recently been identified as GPC-1 (PCT application no: PCT/AU2015/000018). However, the BLCA-38 antibody (a parent cell line to the 1F5 murine MIL-38 antibody) has been reported as not undergoing internalisation (Khatri 2010). BLCA-38 cells were recently shown to be bi-clonal with only one cell population recognising GPC-1 (PCT/AU2014/000999). The 1F5 murine MIL-38 subclone and the chimeric MIL-38 antibody both recognise GPC-1, however their internalization has not to date been investigated in a range of cell types.

DU-145 prostate cancer cells show higher antibody binding than MDA-MBA-231 breast cancer cells or T-24 bladder cancer cells and chMIL-38 is also able to bind PANC-1 cells (FIG. 4). Both murine MIL-38 monoclonal antibody and the chimeric MIL-38 antibody were able to internalise into DU-145 cells with strongest internalization seen at 30 min (FIGS. 5A and B). T-24 cells also demonstrate internalization of the chimeric MIL-38 (FIG. 5D), however MDA-MB-231 cells do not show detectable binding or internalization of MIL-38 under these conditions (FIG. 5C) despite expressing the MIL-38 antigen (FIG. 4). PANC-1 cells show binding of MIL-38 to the cell membrane at 15 min post incubation, then almost complete internalisation of the antibody 60 min after incubation (FIGS. 5E and F).

GPC-1-mediated internalisation of MIL-38 antibodies therefore depends on more than expression of the MIL-38 antigen and may depend on the level of expression or the cell type. The role of cell type is supported by a recent report describing alterations of endosomal function in prostate cancer compared to normal prostate (Johnson et al 2014 *Mol Cancer Res*. 2014 December; 12(12):1851-62).

The chimeric MIL-38 antibody was internalised after binding GPC-1 on the cell surface of either prostate, bladder or pancreatic cancer cell lines. The strong internalisation of chMIL-38 indicates its suitability as an antibody drug conjugate (ADC).

Example 5: Targeting of MIL-38 Antibodies to DU-145 Xenografts 5.1 Materials and Methods Xenograft Model Nude mice were injected subcutaneously in the left flank with $1\times10^6$ DU-145 cells. The cells were allowed to grow for approximately four weeks, then 100 µl of 5 µM Cy-5-labelled antibody in PBS was injected i.v. into the tail vein. Optical images were taken 24 hrs post injection using a Bruker MS-FX Pro scanner. Three mice were injected with Cy-5 labelled 1F5 murine MIL-38 and three mice were injected with Cy-5 labelled chimeric MIL-38.

5.2 Results

Both 1F5 MIL-38 (FIG. 6A) and chimeric MIL-38 (FIG. 6B) demonstrated strong targeting to the DU-145 xenografts in each of the three mice tested per group, with minimal off target binding. Some minor accumulation was also noted at the ear puncture marks, possibly due to inflammation caused by the puncture wound (note no localisation to the unpunctured ears).

5.3 Discussion

Previous data using radio-conjugated BLCA-38 indicated targeting to prostate cancer xenograft (Carter et al 1994), however due to the biclonal nature of the BLCA-38 antibody it is unclear if the 1F5 clone would show similar targeting or whether the AM3-like clone is responsible for the tumour localization seen.

The results shown in FIGS. 6A and 6B indicate that both the 1F5 and chimeric forms of MIL-38 localise to DU-145 tumour xenografts, implying that the 1F5 antibody clone isolated from BLCA-38 mixed population is responsible for tumour targeting and that the second form of antibody present in the BLCA-38 stocks is not required for tumour localization.

The tumour-specific localization of the 1F5 and chimeric MIL-38 antibodies suggests that they would be good agents to deliver anti-prostate cancer therapies such as antibody drug conjugates or radio-immunotherapies.

Example 6: Cell Growth Inhibition Assays 6.1 Materials and Methods

Cell Growth Inhibition Assay

This assay is designed to screen antibodies that may internalise and deliver toxins to cells resulting in cell growth inhibition and/or cell death. Antibodies that induce cell growth inhibition are candidates to convert to an antibody-drug conjugate (ADC) format with the toxin payloads identified.

The assay involves first the incubating the test antibody and target cells in the presence of Protein G that has been linked to different toxins suitable for use in ADC technology. An antibody dose response curve is established with fixed final concentration of protein G-toxin.

The following protein G combinations were chosen:

TABLE 3

| protein G combinations | | |
|---|---|---|
| Preloaded Protein G | Linker | Working Concentration |
| PSGD (preloaded with DM1) | Non-cleavable | 10 nM |
| PSGE (preloaded with MMAE) | Cleavable | 50 nM |
| PSGF (preloaded with MMAF) | Non-cleavable | 100 nM |
| PSGDuc (preloaded with Duocarmycin) | Cleavable | 50 nM |

The assay format was performed as follows:

Cells were plated in 96 well at 20-30% confluency in 100 µl culture medium then incubated overnight. Antibodies were serially diluted, starting from the concentrations indicated in the graph at 19:60 ratio, then added to the 96 well plate containing cells.

Preloaded protein G-drug conjugate was added to treated wells at concentration indicated above. Cells were then incubated for 3 days, then measurement of cell viability was performed using CelltitreGlo.

The following antibodies were tested:
- a. Chimeric MIL-38 (human IgG1)
- b. Murine 1F5 MIL-38 (murine IgG1, high GPC-1 binding subclone of BLCA-38)
- c. Murine BLCA-38 (murine IgG1, mixed population consisting of 1F5-type and AM3 type antibodies)
- d. Murine AM3 (murine IgG, low GPC-1 binding subclone of BLCA-38)
- e. Erbitux (control human IgG1 chimeric anti-EGFR antibody)

6.2 Results

Two cell lines were chosen for inclusion in the assay DU-145 and MDA-MB-231. Both are GPC-1 positive, but exhibit different levels of MIL-38 reactivity and internalization. The antibodies chosen represent a range of different characteristics:

TABLE 4

| | antibodies used | | | | |
|---|---|---|---|---|---|
| | DU-145 | | MDA-MB-231 | | |
| Antibody | Binding | Internalisation | Binding | Internalisation | Isotype |
| Chimeric | ++++ | ++++ | Not tested | – | Human IgG1 |
| BLCA-38 | ++++ | Negative* | ++ | Not tested | Murine IgG1 |
| AM3 | –/+ | Not tested | Not tested | Not tested | Murine IgG1 |
| IF5 | ++++ | ++++ | ++ | Not tested | Murine IgG1 |
| Erbitux | Positive control | Assumed positive | Positive control | Assumed positive | Human IgG1 |

*BLCA-38 is reported not to internalise (Kharti et al 2010).

MDA-MB-231 cells were insensitive to all anti-GPC-1 antibody/toxin combinations (FIGS. 7A to 7D), whereas anti-EGFR/toxin complexes were able to inhibit growth of MDA-MB-231 cells (FIG. 7E). The MDA-MB-231 cells required internalisation of toxins for growth inhibition as evidenced by lack of inhibition with Erbitux alone (FIG. 7E). It is unclear if the insensitivity of MDA-MB-231 cells to anti-GPC-1 antibodies was due to the expression level of GPC-1, the ability of the GPC-1/anti-GPC-1/Protein G toxin complex to internalise or differential processing for anti-GPC-1 vs anti-EGFR complexes.

DU-145 cells were sensitive to all the toxins used in this assay when targeted by Erbitux, but showed no inhibition with Erbitux alone (FIG. 7E). Chimeric MIL-38 was able to induce growth inhibition in DU-145 cells with PSG preloaded with MMAE and MMAF toxins but not Duocarmycin or DM1, demonstrating that the particular toxin involved also had an effect (FIG. 7A). In contrast, IFS MIL-38, BLCA-38 and AM3 were unable to induce cell growth inhibition in these assays.

The concentrations of protein G-duocarmycin used in experiments depicted in FIGS. 7A-7E proved to be toxic to the DU-145 cells even in the absence of antibody, therefore a titration was performed to determine an appropriate lower concentration for DU-145 cells (FIG. 7F panel 1). Erbitux was able to induce cell growth inhibition in a dose-dependent manner under these conditions, but none of the MIL-38 antibodies were able to cause growth inhibition under these conditions.

Internalisation of the antibody alone does not predict growth inhibition: the chimeric MIL-38 and the 1F5 murine MIL-38 internalise to equivalent levels (FIGS. 5A and B). Growth inhibition is observed for chimeric MIL-38 (FIG. 7A) yet no growth inhibition is observed with 1F5 murine antibody (FIG. 7D).

6.3 Discussion

A number of key questions were assessed in these assays:
1. If a cell line expresses the GPC-1 antigen (regardless of expression level) it will be sensitive to anti-GPC-1 antibodies?
2. If an antibody internalises it will be able to cause growth inhibition via internalization of a GPC-1/anti-GPC-1 antibody/protein G toxin complex?
3. Equivalent levels of antibody internalization should lead to equivalent growth inhibition.
4. Relative sensitivity of a cell line/antibody/toxin combination.

MIL-38-derived antibodies display a distinct activity profile compared to the positive control in these assays (Erbitux). Firstly chimeric MIL-38 in combination with the toxins tested shows no activity towards the breast cancer cell line MDA-MBA-231 despite expression of GPC-1 on this cell line. In contrast Erbitux is active against MDA-MB-231 cells with all toxins tested.

Secondly, chimeric MIL-38 shows growth inhibition with MMAE and MMAF toxins for DU-145 cells, whereas murine 1F5, AM3 or BLCA-38 shows no activity. This is particularly unexpected in the case of 1F5 where equivalent internalization has been demonstrated (FIGS. 5A and 5B), suggesting that the differential activity observed is due to the chimeric framework.

It is clear from these results that internalization of either the antigen alone or the antibody do not predict the potential activity of given antibody/antigen complex and that empirical data must be obtained to determine the potential utility of a given molecule.

The observation that MDA-MB-231 cells that express the lowest levels of GPC-1 antigen do not show cell growth inhibition with chimeric MIL-38 despite expressing the GPC-1 antigen suggests that an ADC version of the chimeric MIL-38 may be able to target prostate cancer cells specifically and not affect other tissues with low GPC-1 antigen expression. The identification of growth inhibition with chimeric MIL-38 but not 1F5 suggests that the chimeric format provides unexpected advantages for the deployment of ADC-based strategies.

Example 7: Development of a Scalable Chimeric Expression System 7.1 Materials and Methods Cell Line Development Production of sufficient chimeric antibody for clinical trials and ultimately commercial supply requires a production system capable of high antibody expression and good recoveries following purification. Production of the chimeric antibody described in Example 1 was performed using transient expression, a technique unsuitable to large scale GMP production. Therefore a suitable expression/purification system was developed with the following characteristics:

1. Use of an established gene transduction technology.
2. Use of a cell line of sufficient quality and lineage suitable for clinical grade production
3. Use of cell growth medium, bioreactors and purification techniques suitable for scalable GMP production of final product.

Catalent was selected as the manufacturer due to their extensive experience with GMP production of antibodies and their proprietary GPEX retrovector expression technology.

A stable cell pool was developed using the chimeric MIL-38 heavy and light chains coding sequences incorporated into Catalent's GPEX expression retrovectors.

Following selection, a stable pool was established and used for 25 L scale up production of chimeric MIL-38. The cell supernatant was purified using processes suitable for scalable production.

7.2 Results

A stable pool was established and used for an early stage production run. A 25 L production run was performed as an 18-day fed-batch using the stable cell pool. Viable cell density (FIG. 8A), cell viability (FIG. 8B) and antibody production (FIG. 8C) showed good performance with expression levels of 0.8 g/L obtained at this early stage of development.

The supernatant harvest from the fed batch was clarified, then purified using scalable techniques used for antibody purification, host cell protein and virus reduction (Table 5). Yield of approximately 50% were obtained using non-optimised purification, indicating that a scalable process had been developed.

TABLE 5 yields and recovery during purification of chimeric MIL-38.

| Step | Volume (L) | Conc. (mg/mL) | Total (g) | Step Yield (%) | Overall Yield (%) |
|---|---|---|---|---|---|
| Harvest | 25.0 | 0.81 | 20.3 | 100 | 100 |
| Clarification | 24.7 | 0.77 | 18.9 | 93 | 93 |
| Protein A/Low pH Hold | 2.4* | 6.6 | 15.9 | 84 | 78 |
| Q Flow through | 2.22 | 5.2 | 11.5 | 94 | 73 |
| CEX Bind and Elute | 0.50 | 16.1 | 8.0 | 75** | 55 |
| Viral Filtration | 0.77 | 9.2 | 7.1 | 89 | 49 |
| Formulation | 0.78 | 9.3 | 7.3 | 103 | 50 |

7.3 Results

A stable CHO cell pool expressing chimeric MIL-38 was established using the GPEX technology and used for an early stage production run. Good expression was observed during the initial fed batch production run and good recoveries were achieved using standard purification processes known to be suitable for GMP production.

The stable pool will form the basis for future cell line development, incorporating clone isolation and master and working cell bank construction. The purification process used can be further optimized to increase yields.

Use of well established cell lines, expression vectors, cell growth systems and purification techniques means that the final antibody product obtained from the 25 L pilot batch should possess very similar characteristics to that produced from the final production process. The yields obtained to date indicate that the product can be produced at costs consistent with other marketed antibody products.

Example 8: Development of a Chimeric MIL-38 DOTA Conjugate for Imaging and Radiotherapy 8.1 Materials and Methods Conjugation of MIL-38 with DOTA for $^{177}$Lu Labeling DOTA was conjugated to chimeric MIL-38 at a 10:1 ratio as follows. p-SCN-Bn-DOTA was prepared in 0.1M PBS (pH 8.5) buffer, then chimeric MIL-38 (cMIL-38) was added to the mixture. The mixture was allowed to react for 20 hours at room temperature in the dark.

The conjugated mAb mixture was purified using a pre-conditioned mini PD-10 gel column. Fractions were screen fractions for activity by HPLC.

Labeling of MIL-38 with $^{177}$Lu 0.472.1 mCi of $^{177}$Lu in 10 µL of 0.05N HCl was added to 0.2 mg of DOTA-cMIL-38, then the pH adjusted to pH 7.5. The mixture was incubated at 50° C. for 60 min in the dark, then cooled to room temperature and let sit for 20 min.

The radiolabelled MIL-38 DOTA was purified using a pre-conditioned mini PD-10 gel column. The column was preconditioned with 2 mL of 1×PBS and the effluent discarded. This was repeated four times in total, then the radioactive solution was added to the centre of the column. 0.2 ml of PBS was added and the fraction collected in a low binding Eppendorf tube. This was repeated another 19 times, then the activity in each fraction was determined using a dose calibrator. A sample of the radioactive mAb was analysed using radio-HPLC for confirmation analysis.

Mock Labeling of MIL-38 DOTA and FLOW Cytometry

To confirm that binding of chimeric MIL-38 to DU-145 cells was retained following conjugation with DOTA and after the radio-labeling process, MIL-38 DOTA was put through a "mock" radiolabeling process in which it was incubated with the same buffers and exposed to the same temperatures that are used during the radio-labeling process described above. The PD-10 column purification steps were omitted.

The chimeric MIL-38, MIL-38 DOTA and mock-labelled MIL-38 DOTA were then each used as the primary antibody for FLOW cytometry analysis.

Conjugation of chMIL-38 with DOTA for Scale Up Manufacture and $^{67}$Ga Labelling Conjugation of chMIL-38 to p-SCN-Bn-DOTA (DOTA) was undertaken following the method outlined by Forrer et al. titled "in vitro characterization of $^{177}$Lu-radiolabelled chimeric anti-CD20 monoclonal antibody and a preliminary dosimetry study". Three conditions were used: 5, 10 and 20 fold excess of DOTA. Briefly, three vials of chMIL-38 (9.3 mg/ml) were combined and buffer exchanged from 0.01M PBS to 0.2Na$_2$CO$_3$, pH9.5. The chMIL-38 solution was then concentrated to a final volume of 433 µl, giving an effective concentration of 64.4 mg/ml. The material was split into three 144 µl aliquots then reacted with DOTA (5, 10 or 20 equivalents). Each reaction mixture was maintained at 37° C. or 1 hour. Samples were then washed with 5 ml of Na$_2$CO$_3$ buffer pH 9.5 then buffer exchanged with 0.25M ammonium acetate, pH7.

Mass spectral analysis indicated that the number of DOTA attached was 4.3 DOTA: MAb (5 fold reaction excess), 4.6 DOTA: MAb (10 fold reaction excess) and 7.5 DOTA: MAb (20 fold reaction excess).

$^{67}$Ga labeling of chMIL-38 DOTA

67Ga-labeling of chMIL-38 DOTA was performed using the product generate from the fold reaction excess containing 7.5 DOTA:MAb ratio. Reaction conditions: 50 µl $^{67}$GaCl$_3$ in 0.02M HCl, 100 µl 0.1M NaOAc buffer at pH 5.0, chMIL-38 DOTA: 5 to 25 µl of antibody (46-230 µg)

was used. The mixture was incubated at 40'C for 1 or 16 hours. The radiochemical yield and derived specific activity were calculated.

Assessment of DOTA Conjugation and Labelling Conditions on MIL-Antigen Binding by FLOW Cytometry and Direct Binding ELISA To confirm that the reaction conditions used to conjugate DOTA to chMIL-38 using 5, 10 or 20 fold excess of DOTA did not significantly alter binding of chMIL-38 DOTA to GPC-1 two assays were used: FLOW cytometry and a direct binding ELISA. FLOW cytometry was performed as follows. DU-145 or T-24 cells were detached using 2 mM EDTA (10 min at 37° C.). Cells were pelleted, and then $2\times10^5$ cells per tube were prepared. Cells were incubated with primary antibody (1 μg/ml, 50 μl) on ice for 45 min, then washed three times in FACS wash buffer (1×PBS solution). Cells were then incubated with 50 μl of secondary antibody (1 μg/ml AlexaFluor 488 goat anti-human (H+L)) for 45 min. Cells were washed three times in FACS wash buffer then run through BD LSRFortessa™—Cell analyser using software BD FACSDIVA™.

The GPC-1 direct binding ELISA was performed as follows. 96 well plates were coated with 10 mM Carbonate buffer, pH 9 for 15 mins. The carbonate buffer was removed and wells were coated overnight at room temperature with 1.5 μg/ml recombinant human GPC-1 (R&D systems) in 10 mM Carbonate buffer, pH 9. The following day wells were washed with 5 mM carbonate buffer, pH 9 then blocked with 10% casein in PBS for 1 hours. The primary antibody was serially diluted starting at 25 ng/mL to 0.39 ng/mL then incubated 1 hours at room temperature. Plates were then washed four times with PBS-Tween 20 (0.1%). Secondary antibody Thermofisher rabbit anti-human was diluted 1:8000 in PBS-Tween, 10% casein then incubated for 1 hours at room temperature. Plates were washed four times with PBS-Tween and 100 μl TMB added. Plates were developed for 2 min and read at $\lambda_{450}$ nm.

8.2 Results

FIG. 9A shows an A280 absorbance trace of gel filtration standards used to calibrate the HPLC. FIG. 9B shows an A280 absorbance trace of un-conjugated chimeric MIL-38. FIG. 9C shows an A280 absorbance trace of chimeric MIL-38 following DOTA conjugation and PD-10 column clean up. FIG. 9D shows a radio-HPLC trace of $^{177}$Lu activity following labeling of MIL-38 DOTA with $^{177}$Lu and PD-10 column clean up. FIG. 9E shows the A280 absorbance trace corresponding to FIG. 9D.

Using the conjugation, labeling and purification procedures described above, a single peak of $^{177}$Lu radiolabelled chimeric MIL-38 DOTA is obtained.

FIG. 10 shows the FLOW histograms for chimeric MIL-38, chimeric MIL-38 DOTA and mock-labelled chimeric MIL-38 DOTA. DOTA conjugation slightly reduces the Fluorescence signal observed compared to untreated chimeric MIL-38. Mock labelling does not affect the fluorescence detected when compared to MIL-38 DOTA.

Alternate conjugation conditions were used for scale up production of chMIL-38 DOTA and for labelling with $^{67}$Ga. $^{67}$Ga has a half-life of ~3.3 days and is therefore a better isotope to predict the in-vivo biodistribution of chMIL-38 DOTA-labelled chMIL-38 than isotopes such as $^{68}$Ga (half life ~68 min).

FIG. 11 shows labeling of DOTA-conjugated MIL-38 with $^{67}$Ga. FIG. 11A shows a size exclusion chromatography HPLC chromatogram of the radioactivity of MIL-38 labelled with $^{67}$Ga. The star indicates free $^{67}$Ga remaining in the reaction mixture FIG. 11B shows a stability study of $^{67}$Ga-labelled MIL-38 DOTA. The size exclusion chromatography HPLC chromatogram of the radioactivity of MIL-38 labelled with $^{67}$Ga is shown together with the corresponding UV trace. The $^{67}$Ga-MIL-38 preparation had free $^{67}$Ga removed, then was allowed to remain at room temperature for two weeks prior to undergoing SEC HPLC chromatograph. While there is some detachment of the $^{67}$Ga from the chMIL-38 DOTA (indicated by the second peak at ~10 min elution time), the majority of the antibody and radioactivity remained intact under these conditions indicating good stability.

To maximise specific activity of the $^{67}$Ga-labelled chMIL-38 DOTA, the effects of the ratio of chMIL-38 DOTA to $^{67}$GaCl$_3$ and incubation time (1 hours vs 16 hours) were examined. As shown in Table 6 the amount of antibody in the reaction mix was the most important variable in determining radiochemical yield (RC) and the derived specific activity (SA).

TABLE 6

Effects of antibody mass and incubation times on radiochemical yield and derived specific activity for chMIL-38 labelling with $^{67}$Ga

| Reaction ID | Reaction Time (h) | 67 Ga Activity (MBq) | Mass of Antibody (ug) | RC Yield (%) | Derived SA MBq/mg |
| --- | --- | --- | --- | --- | --- |
| NGL07104-1 | 1 | 40.4 | 230 | 98 | 170 |
| NGL07104-2 | 1 | 39.5 | 92 | 79 | 340 |
| NGL07104-3 | 1 | 37.4 | 46 | 72 | 585 |
| NGL07104-4 | 16 | 37.8 | 230 | 97 | 136* |
| NGL07104-5 | 16 | 38.1 | 92 | 83 | 293* |
| NGL07104-6 | 16 | 38.1 | 46 | 84 | 594* |

*Decay corrected value (18 h decay, x0.853)

As the conditions used for conjugation of DOTA to chMIL-38 and for labelling with $^{67}$Ga labelling may affect the binding activity a series of experiments was designed to examine the effects of these procedures on chMIL-38 binding to the GPC-1 antigen in two distinct assays: FLOW cytometry (targeting the cell-bound antigen) and a direct binding ELISA (targeting a surface bound recombinant form of GPC-1).

The effects of the labelling conditions were determined by "mock-labeling" as described previously. As well, the intra- and inter-assay reproducibility of these assays was assessed.

FIG. 12 shows binding of chimeric MIL-38, MIL-38 DOTA prepared using three different DOTA conjugate ratios and mock radio-labelled MIL-38 DOTA to DU-145 or T-24 cells using FLOW cytometry, as well as binding in a direct antigen binding ELISA. FIG. 12A shows binding of un-labelled chimeric MIL-38 or chimeric MIL-38 that had been conjugated to DOTA using either a 5, 10 or 20 fold molar excess of DOTA. Essentially equivalent binding curves were obtained indicating that the DOTA conjugation did not cause a reduction in MIL-38 binding to DU-145 cells. FIG. 12B shows FLOW cytometry binding to T-24 cells of three separate batches of chMIL-38 DOTA (20 fold excess) that had each undergone a mock-labelling reaction. Essentially identical binding curves were observed indicating good inter-batch reproducibility. FIG. 12C shows FLOW cytometry binding to T-24 cells of three separate FLOW reactions of chMIL-38 DOTA (20 fold excess) all prepared from one batch that had undergone a mock-labelling reaction. Essentially identical binding curves were observed indicating good intra-batch reproducibility. FIG. 12D shows overlayed FLOW cytometry profiles of binding to T-24 cells for secondary antibody alone (red trace), chMIL-38 DOTA (green trace), one sample from the inter-batch reproducibility (Batch 1, blue trace) and one sample from the intra-batch reproducibility (Intra 1, orange trace). Essentially identical binding curves were observed indicating that the mock-labelling process did not affect binding to cells compared to the chMIL-38 DOTA control. FIG. 12E shows binding of chMIL-38 and chMIL-38 that had been conjugated to DOTA using either a 5, 10 or 20 fold molar excess of DOTA to recombinant GPC-1 in a direct binding ELISA. FIG. 12F shows direct binding to recombinant GPC-1 of chMIL-38 DOTA, the 3 different preparations of mock-labelled chMIL-38 DOTA prepared for the inter-batch comparison and 3 different reactions from the intra-batch preparation.

The conjugation of DOTA to chMIL-38 reduced its binding to GPC-1 in the direct assay compared to the unconjugated chMIL-38, although this effect was only observed at lower antibody concentrations and was not dependent on the DOTA ratio used in the experiment or the number of DOTA molecules attached (FIG. 12E). The mock-radiolabelling conditions tested did not affect the binding of chMIL-38 DOTA compared to chMIL-38 DOTA that was not subjected to mock labelling and the assay showed good inter and intra-batch reproducibility (FIG. 12F).

8.3 Discussion

A method has been successfully developed to conjugate chimeric MIL-38 with the DOTA chelation molecule. A chimeric MIL-38 DOTA antibody can be labelled with agents such as $^{67}Ga$ for imaging, or $^{177}Lu$ for imaging and radio immunotherapy treatment. Other agents such as Gadolinium or $^{90}Yttrium$ can also be chelated with the DOTA chelator.

FLOW cytometry and direct binding data indicates that the conjugation and labeling processes have minimal effect on the ability of chimeric MIL-38 to bind DU-145 cells.

Example 9: Chimeric MIL-38 Localization in a Mouse Xenograft Model 9.1 Materials and Methods
Antibody Labelling and Internalisation
Chimeric MIL-38 was labelled with the Cy5 fluorophor for visualisation. Retention of binding activity post labelling was confirmed by FLOW cytometry using DU-145 cells. ChMIL-38 Cy5 demonstrated clear internalisation into DU-145 cells.
Xenografts and Antibody Infusions
Three 8-week-old male Balb/c nude mice were injected subcutaneously with $5\times10^6$ DU-145 cells in 100 μL serum free media (RPMI) into the right flank of each mouse. At 26 days all mice had palpable tumours (approximately 4 mm across). Antibody solution (approx. 150 μg/injection) was injected via the tail vein and then imaged using the Bruker In-Vivo Xtreme Optical Scanner at 0, 4 hours, 24 hours, 48 hours, 72 hours and 144 hours.

9.2 Results
Tumour localisation was seen at 4 hours in two of three mice and was clearly evident at 24 hours post infusion in all three mice tested (FIG. 13A). Tumour localisation was maintained at 48 and 72 hours while non-tumour signal decreased. Optimal tumour to background signal was observed at 144 hours at which time background signal had cleared. The chMIL-38 Cy5 infusions were well tolerated. FIG. 13B shows a Multi-modal Animal Rotation System (MARS) image of a representative mouse from FIG. 13A after 144 h.

Example 10: Biodistribution Study of $^{177}Lu$ DOTA MIL-38

10.1 Materials and Methods
Biodistribution Study
Male Wistar rats were injected at $T_0$ with 5 planned exsanguination time points for dissection and measurement of key organ radioactivity accumulation. Planned time points were 6 hours, 24 hours, 48 hours, 7 days and 14 days.
DOTA conjugated MIL-38 antibody, supplied by Singapore Radiopharmaceuticals was radiolabelled with $^{177}Lu$ and passed bench top quality assurance testing.

10.2 Results
A standardised plot of % of injected activity per gram of organ at the different timepoints (FIG. 14) indicates a safe radioimmunotherapy profile without evidence of toxic accumulation in analysed tissues and organs. Of note, key excretory organs (liver, kidneys) do not display evidence of toxic radioactive accumulation (FIG. 15).
No adverse events were noted with the test animals.

10.3 Discussion
$^{177}Lu$-labelled chimeric MIL-38 DOTA showed good tolerability with no evidence of toxic accumulation in tissues or organs, in particular excretory organs. The agent was well tolerated with no adverse events noted.
These results in normal rats combined with the tumour targeting seen with fluorescently labelled chimeric MIL-38 (FIGS. 6 and 13) suggest that the MIL-38 DOTA conjugate is likely to have applicability for both imaging and radioimmunotherapy of prostate cancer.

Example 11: PET Imaging Study of $^{64}Cu$ chMIL-38 DOTA and NOTA in Xenografts 11.1 Materials and Methods
The aim of this study was to examine in vivo targeting of radio-labelled chMIL-38 to DU-145 xenografts using PET-CT and ex vivo organ analysis. As neither $^{67}Ga$ nor $^{177}Lu$ can be used for used for PET-CT imaging $^{64}Cu$ was used as the radiolabel. NOTA is the preferred chelator for $^{64}Cu$, hence chimeric MIL-38 was also conjugated to the NOTA chelator and $^{64}Cu$ was used as the imaging isotope. Imaging was performed using a Siemens Inveon PET-CT scanner. Both $^{64}Cu$ chMIL-38 NOTA and $^{64}Cu$ chMIL-38 DOTA were used for imaging and biodistribution purposes.

8-week-old male Balb/c nude mice were injected subcutaneously with $5\times10^6$ DU-145 cells in 100 μL serum free media (RPMI) into the right flank of each mouse. There was no evidence of ulceration at the time of dosing, the animals were closely monitored and remained in good condition apart from the tumours. At 38 days all mice had palpable tumours (approximately 4 mm across). Antibody solutions were injected via the tail vein at 54 days post inoculation and then imaged using the Siemens Inveon PET-CT instrument. Two mice were infused with $^{64}$Cu chMIL-38-DOTA and three mice with $^{64}$Cu chMIL-38-NOTA. Each mouse received approximately 100 µg of chMIL-38 with activities of 3.1-3.4MBq (chMIL-38 DOTA) or 4-4.8MBq (chMIL-38 NOTA).

The PET Images were reconstructed using an ordered-subset expectation maximization (OSEM2D) algorithm and analysed using the Inveon Research Workplace software (IRW 4.1) (Siemens) that allows fusion of CT and PET images and definition of regions of interest (ROIs). CT and PET datasets of each individual animal were aligned using IRW software (Siemens) to ensure good overlap of the organs of interest.

Mice were imaged at 24 hours and 48 hours, then the major organs were removed from the mice and the amount of antibody present was measured by γ-analysis.

11.2 Results

In vivo imaging showed good tumour accumulation and long term localisation (over 2 days) for the chMIL38 NOTA antibody as was observed for the Cy5-labelled chMIL-38 (FIG. 16). There was far higher binding and accumulation in the tumour for the NOTA-labelled antibody compared to the DOTA-labelled antibody (FIG. 17). This may be due to either instability of the chelator in vivo (for the case of the DOTA), chelator-induced non-specific uptake in other organs, or loss of $^{64}$Cu from the DOTA due to the lower binding efficiency. The NOTA-labelled antibody showed high accumulation in the tumour, approximately equal to that observed for other antibody systems.

Ex vivo analyses showed biodistribution at 48 hours for the chMIL38 antibody labelled using the two different approaches (FIG. 17). For chMIL-38 NOTA there was almost equal signal in the liver as the tumour indicating effective targeting. Imaging to longer time points would be expected to show almost exclusive tumour delineation.

Example 12: Targeting and Tolerability Study of Goat Anti-GPC-1 in Xenografts 12.1 Materials and Methods MIL-38 does not recognise mouse GPC-1, therefore there is a possibility that the tumour-specific localisation of chMIL-38 and the good tolerability seen in other studies may be due to the chMIL-38 only targeting human GPC-1 on the xenograft tumours and not targeting endogenous murine or rat GPC-1.

A goat anti-GPC-1 antibody was identified that recognises mouse recombinant GPC-1 on western blots and can immunoprecipitate mouse recombinant GPC-1 suggesting that it recognises the native (cell surface) form of mouse GPC-1. The Goat anti-GPC-1 antibody was therefore used to confirm that the safety and tolerability results seen for chMIL-38 were also seen with an antibody that recognised mouse GPC-1.

The FDA guidance on exploratory Investigational New Drugs suggests a maximum microdose for proteins of <30 nmoles. For a full-length monoclonal antibody this is approximately 4.5 mg protein. ~0.3 mg of antibody in a mouse is equivalent to a Human Equivalent Dose (HED) of 4.5 mg antibody with a safety factor of 22 or 1 mg antibody with a safety factor of 100 (see Table 7). 300 µg of Goat anti-GPC-1 was used as the highest dose per infusion.

6 BalbC mice with DU-145 xenografts were dosed with goat anti-GPC-1 labelled with Cy5 via the tail vein. Three were dosed with 150 µg of antibody and three were dosed with 300 µg of antibody.

TABLE 7

Calculation of goat anti-GPC-1 does for tolerability study.

Human Equivalent Dose (HED) calculations

| | | |
|---|---|---|
| Proposed human total dose (mg) | 1 | 4.5 |
| Safety factor | 100 | 22.2 |
| Equivalent total dose (mg) | 100 | 100 |
| Av pt weight (kg) | 75 | 75 |
| Dose (mg/kg) | 1.33 | 1.33 |
| Conversion factor** | 12.3 | 12.3 |
| Animal dose (mg/kg) | 16.4 | 16.4 |
| Weight of mouse (g) | 20 | 20 |
| Dose per mouse (µg) | 328 | 328 |

*recommended margin for safety factor is 100-22

Guidance for Industry on Estimating the Maximum Safe Starting Dose in Initial Clinical Trials for Therapeutics in Audlt Health Volunteers

**for human: mouse refer pg. 7 Guidance for Industry Estimating the Maximum Safety Sarting Dose in Initial CLinical Trials for Therapeutics in Adult Healthy Volunteers Chimeric MIL-38 does not bind recombinant mouse GPC-1

Goat anti-GPC-1 binds both recombinant human and mouse GPC-1

Goat anti-GPC-1 can act as a surrogate in a mouse tolerability study 12.2 Results Targeting In vivo imaging showed tumour accumulation and long-term localisation (over 5 days) for the goat anti-GPC antibody. This was particular apparent in mouse 2.2 and 2.3 images (FIGS. 18A and 18B) and the MARS image (FIG. 18C).

Ex vivo analyses (FIG. 18B) showed that the goat anti-GPC antibody exhibited strong signals in the tumours. Some residual signal in the gut of all animals suggested that the antibody was being cleared most likely through the biliary system.

Safety and Tolerability

Mice were assessed during the study according to appearance, clinical signs, unprovoked behavior and response to external stimuli (Table 8). Weight was also monitored.

None of the mice showed any significant health effects due to the antibodies used based on the score sheet used in this study. A single mouse (mouse 2.3) showed minor sluggishness following injection, but this was attributed to a minor burn on the tail incurred during injection. This mouse subsequently recovered during the course of the study.

Minimal variation in weight for each mouse was observed over the course of the study.

TABLE 8

Assessment of safety and tolerability.

| Indicators Date | Score of each animal in group | Scoring of independent variables: |
|---|---|---|
| Appearance: | | 0. Normal coat is smooth, lies flat and often has a sheen, eyes are clear and bright.<br>1. Slightly ruffled coat but no other marked changes<br>2. Moderate ruffled coat, eyes and nose may have discharges<br>3. Very ruffled coat, external orifices ungroomed, abnormal posture, may look hunched up, eyes look pale and pupils enlarged. |
| Clinical Signs | | 0. Respiration appeas normal, body, temperature feels normal on handling, no twitching behavior, normal bowel movements<br>1. Small changes in above parameters<br>2. Body temperature appears above normal, respiration rapid and shallow breathing, twitching behavior, altered bowel movement (change in consistency or amount).<br>3. Marked increasing body temperature, respiration noisy, comatose. |
| Unprovoked behavior | | This behavior is best observed from a distance and before any handling is attempted.<br>  0. Normal behavior pattern<br>  1. Minor changes<br>  2. Abnormal behavior, less mobile and less altert than normal, inactive when hyperactivity would be expected.<br>  3. Unsolicited vocalization, self-mutilation, expirator grunts, very restless or does not move at all. |
| Behavioral responses to external stimuli | | Often mice will show inquisitiveness with whisker twitching and sniffing, or attempts to escape if frightened. Mice can have good body tone and paw grip on handling. If the abdominal area of the body is painful then gently pressure and observation is a useful measure to pain.<br>  0. Behavioral respoinses normal for the expected conditions<br>  1. Shows some minor depression or minor exaggeration of responses.<br>  2. Shows moderate signs of abnormal responses, there may be a change of behavior.<br>  3. Reacts violently to stimuli or muscular responses may be very weak as in pre-comatose state |

Total scores of:
0-4—Normal, no action required
5-10—Monitor carefully, evidence of suffering
10 and above—ample evidence of sever pain, euthanase the animal
One score of 3 in any of the criteria—euthanase immediately.

Discussion

The Goat anti-GPC-1 showed almost identical targeting to the chMIL-38 results seen in FIG. 13B, particularly at the 120 hours time point. This suggests that there is limited binding to other organs, implying that GPC-1 is either not cell-surface expressed or expressed at low levels on the cell surface without high expression in any particular organ.

The goat anti-GPC-1 antibody was well tolerated at both doses.

Example 13: Detection of Glypican-1 Antigen Using AM4 MIL-38 Antibodies

Experiments performed by the present inventors determined that an original deposit of the hybridoma for MIL-38 antibody (ATCC accession no. HB11785: murine hybridoma BLCA-38), then referred to as the "BLCA-38 hybridoma" is a mixed population of hybridoma cells that produces two distinct antibody populations, referred to here as "AM3" and "AM4". Hybridoma cells responsible for producing each different antibody population were separated, and the "AM4" hybridoma cells were deposited on 22 Aug. 2014 at CellBank Australia (CBA) under accession number CBA20140026.

Ninety-six well plates were coated with MIL-38 preps AM3 or AM4 (1 μg/well) in carbonate buffer pH 9.5 overnight. Plates were blocked with PBS-Tween (0.1%) containing 5% skim milk at 37° C. and washed. Antigen (GPC-1 NS0) was diluted in Buffer II (20 mM HEPES pH 7.5, 0.5 mM EDTA, 0.5% Triton X-100) with the addition of 150 mM NaCl and incubated overnight at 37° C. Detection was performed with biotinylated AM4 antibody followed by detection with avidin HRP (1 µg/mL). TMB (Sigma cat no T0440) was added and stopped with TMB stop solution (Sigma S5814). Absorbance was read at 450 nm. Results are shown in FIG. 19A.

In a second experiment, ninety-six well plates were coated with MIL-38 preps 34A (a mixture of AM3 and AM4 antibodies) or AM4 (2.5 µg/well) in PBS pH 7.2 for 1 h at room temperature. Plates were blocked with Blocker Casein (Thermo) in PBS-Tween (0.05%) for 1 h at 37° C. Following washing, antigen (GPC-1 NS0) was diluted in TBS pH 7.2 containing 50 mM Tricine and 150 mM NaCl and incubated at 37° C. for 1 h. Detection was performed with biotinylated AM4 clone 1F5 followed by detection with avidin HRP (1 µg/mL). TMB (Sigma cat no T0440) was added and stopped with TMB stop solution (Sigma S5814). Absorbance was read 450 nm. Results are shown in FIG. 19B.

The first ELISA described above was developed using MIL-38 to capture NS0 produced GPC-1 (i.e. MIL-38 antigen). This experiment compared monoclonal AM3 MIL-38 and monoclonal AM4 MIL-38 for capture. AM3 did not function as a capture agent in a sandwich ELISA assay, whereas AM4 was shown to do so (FIG. 19A).

The second ELISA described above compared the ELISA signal obtained when a mixed population of MIL-38 (AM3 and AM4) was compared to that obtained from a monoclonal AM4 1F5 clone. Using AM4 1F5 as a capture agent provided a higher ELISA signal than using the mixed 34A antibody population (FIG. 19B).

The sandwich ELISA results demonstrate that only the AM4-like forms of the monoclonal MIL-38 antibody have utility in detecting glypican-1 antigen as a capture reagent and that a capture agent containing a monoclonal population provides a superior ELISA signal to that consisting of a mixed population.

Example 14: Sequence Analysis of AM4 and AM3 MIL-38 Antibody Populations

Materials and Methods

Heavy and Light Chain Sequencing (DNA)

Three separate sequencing runs were performed. The first run (coded 224945) utilised bi-clonal hybridoma cells from a mixed (AM4 and AM3) preparation named 1-O. The second run (coded 449295-1) utilised cells from Alfio I a hybridoma stock that was used to generate AM4. The third run (coded 449295-5) utilised cells from Alfio II, a hybridoma stock that was used to generate AM3.

For sequencing runs 224945 (1-O) and 449295-1 (Alfio 1), total RNA was extracted from frozen hybridoma cells and cDNA was synthesized from the RNA. RT-PCR was then performed to amplify the variable regions (heavy and light chains) and constant regions of the antibody, which were then cloned into a standard cloning vector separately and sequenced.

Total RNA was isolated from the hybridoma cells following the technical manual of TRIzol® Plus RNA Purification System. The total RNA was analysed by agarose gel electrophoresis. Total RNA was reverse transcribed into cDNA using isotype-specific anti-sense primers or universal primers following the technical manual of SuperScript™ III First-Strand Synthesis System. The antibody fragments of VH, VL, CH and CL were amplified according to the standard operating procedure of RACE of GenScript.

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

$V_H$ and $V_L$ plasmids encoded the full-length variable regions of the antibody and a part of $C_H1$ and $C_L$. $C_H$ plasmid encoded a part of $C_H1$ and full-length $C_H2$ and $C_H3$. $C_L$ plasmid encoded a part of $C_L$. In order to get full-length constant regions or heavy/light chain, the part of constant regions encoded by $V_H$ and $V_L$ plasmids and the part of constant regions encoded by $C_H$ and $C_L$ plasmids were amplified by PCR separately, and then overlap extension PCR was employed to obtain full-length DNAs. Five single colonies with correct $V_H$, $V_L$, $C_H$ and $C_L$ insert sizes were sent for sequencing.

Sequencing run 449295-5 (Alfio II) encountered difficulty obtaining sequence corresponding to the expected IgG1 heavy chain sequence. Two RNA preparations were performed. For the 1st batch of cells, oligo-dT primer and CDS III primers were used for reverse transcription (RT). VH/CH and VK/CK were amplified by PCR using IgG1 and IgK specific primers, partial mouse β-actin gene was amplified as positive control. Normal light chain bands were obtained easily while only weak VH could be observed on the gel. Five individual colonies with correct VK and CK insert sizes were sent for sequencing. The VK and CK genes of five different clones were found to be nearly identical. The consensus light chain sequences from the Alfio II hybridoma is listed below. One unproductive heavy chain sequence was obtained from eight randomly sequenced VH positive clones, shown as below. Three kinds of heavy chain constant region sequences were obtained from ten randomly sequenced CH positive clones (one $IgG_1CH$, one $IgG_{2a}CH$ and eight $IgG_{2b}C_H$). In order to avoid the influence of potential class switching, amplification of the $C_H$ using IgM specific primer was performed, but no target PCR product was obtained. There was also no target PCR product when full-length heavy chain ($V_H$-$C_H$) was amplified using heavy chain FR1 degenerate primers.

As no productive heavy chain could be obtained after several attempts, isolation of heavy chain sequence from the 2nd vial of Alfio II cells was attempted. For the 2nd vial of cells, oligo-dT primer was used for reverse transcription initially. $V_H$ was amplified using IgG1, IgG2b, IgM, IgA specific primers and IgG degenerate primer, respectively, and VK was amplified using IgK specific primers. Productive light chain and unproductive heavy chain, which were identical with previous results, were obtained. Reverse transcription using Random 6 mers primer was also attempted without success.

In summary, multiple attempts to isolate light chain and heavy chain sequence were made. One rearranged light chain sequence was consistently obtained after different attempts on two batches of cells. However, only weak VH target PCR products were observed and sequencing did not result in any consistent heavy chain sequence.

Results

Sequencing (DNA)

The isolated total RNA of the sample was run alongside a DNA marker (Marker III—TIANGEN, Cat. No.: MD103) on a 1.5% agarose/GelRed™ gel.

Four microliters of PCR products of each sample were run alongside the DNA marker (Marker III) on a 1.5% agarose/

GelRed™ gel. The PCR products were purified and stored at −20° C. until further use.

The $V_H$, $V_L$, $C_H$ and $C_L$ genes of five different clones were nearly identical. The consensus sequence (SEQ ID NO: 1—AM4 MIL-38 Mouse IgG$_1$ Heavy Chain DNA Consensus Sequence; SEQ ID NO: 2—AM4 MIL-38 Mouse Kappa light Chain DNA Consensus Sequence) was determined to be the sequence of the antibody produced by the monoclonal hybridoma population (AM-4).

The heavy and light chain AM4 MIL-38 consensus DNA sequences above translate to the AM4 heavy chain amino acid sequence (SEQ ID NO: 3—AM4 MIL-38 Mouse IgG1 Heavy Chain Amino Acid Consensus Sequence) and the AM4 light chain amino acid sequence (SEQ ID NO: 4—AM4 consensus MIL-38 Light Chain Amino Acid Consensus Sequence).

AM3 Consensus Sequences

No consistent heavy chain sequence could be obtained from the AM3-like Alfio II cells. The light chain sequence obtained from sequencing run 449295-5 (Alfio II) was consistently obtained and showed clear differences in both the framework regions and the complementarity-determining regions compared to the sequence for the other two sequencing runs.

AM3 MIL-38 Kappa Light Chain DNA Consensus Sequence
(SEQ ID NO: 10)

*ATGGGCATCAAGATGGAGTCACAGACTCAGGTCTTTGTATACATGTTG*

CTGTGGTTGTCTGGTGTTGATGGAGACATTGTGATGACCCAGTCTCAA

AAGTTCATGTCCACATCAATAGGAGACAGGGTCAGCGTCACCTGCAAG

*GCCAGTCAGAATGTGGGTTCTCATGTAGCCGGTTTCAGCAGAAACCAG*

GGCAATCTCCTAAAGCACTGATTTAC*TCGGCATCCTACCGGTACAGCG*

GAGTCACTGATCGCTTCACAGGCAGTGGATCTGGGACAGATTTCACTC

TCACCATCAACAATGTGCAGTCTGAAGACTTGGCAGAGTATTTCTGTC

AGCAATATAACAGTTTTCCATTCACGTTCGGTTCGGGGACAAAGTTGG

AAATAAAA*CGGGCTGATGCTGCACCAACTGTATCCATCTTCCCACCAT*

*CCAGTGAGCAGTTAACATCTGGAGGTGCCTCAGTCGTGTGCTTCTTGA*

*ACAACTTCTACCCCAAAGACATCAATGTCAAGTGGAAGATTGATGGCA*

*GTGAACGACAAAATGGCGTCCTGAACAGTTGGACTGATCAGGACAGCA*

*AAGACAGCACCTACAGCATGAGCAGCACCCTCACGTTGACCAAGGACG*

*AGTATGAACGACATAACAGCTATACCTGTGAGGCCACTCACAAGACAT*

*CAACTTCACCCATTGTCAAGAGCTTCAACAGGAATGAGTGTTAG*

*Individual regions of light chain encoded sequence are highlighted with alternating italics. Positions: 1-72 = leader sequence; 73-141 = framework region (LFR1); 142-174 = complementarity determining region (LCDR1); 175-219 = LFR2; 220-240 = LCDR2; 241-336 = LFR3; 337-363 = LCDR3; 364-393 = LFR4; 394-714 = constant region (CK); 715-717 = stop codon AM3 MIL-38 Light Chain Amino Acid Consensus Sequence
(SEQ ID NO: 11)

*MGIKMESQTQVFVYMLLWLSGVDGD*IVMTQSQKFMSTSIGDRVSVTCK

*ASQNVGSH*VAWFQQKPGQSPKALIY*SASYRY*SGVTDRFTGSGSGTDFT

LTINNVQSEDLAEYFCQQYNSFPFTFGSGTKLEIK*RADAAPTVSIFPP

SSEQLTSGGASVVCFLNNFYPKDINVKWKIDGSERQNGVLNSWTDQDS

KDSTYSMSSTLTLTKDEYERHNSYTCEATHKTSTSPIVKSFNRNEC**

Individual regions of light chain amino acid sequence are indicated with alternating italics as labelled: Positions 1-24 = Leader sequence; 25-47 = framework region (LFR1); 48-58 = complementarity determining region 1 (LCDR1); 59-73 = LFR2; 74-80 = LCDR2; 81-112 = LFR3; 113-121 = LCDR3; 122-131 = LFR4; 132-238 = kappa constant region (CK) & stop codon (*)

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

The invention claimed is:

1. A composition comprising:
   first antibodies and/or antigen binding fragments thereof, that are conjugated to at least one cytotoxic agent which is toxic to a prostate, bladder, and/or pancreatic cancer cell, and wherein the first antibodies comprise:
   (a) a heavy chain variable region comprising:
      a complementarity determining region 1 (CDR1) comprising or consisting of an amino acid sequence defined by positions 50-54 of SEQ ID NO: 3;
      a complementarity determining region 2 (CDR2) comprising or consisting of an amino acid sequence defined by positions 69-85 of SEQ ID NO: 3; and
      a complementarity determining region 3 (CDR3) comprising or consisting of an amino acid sequence defined by positions 118-126 of SEQ ID NO: 3; and
   (b) a light chain variable region comprising:
      a complementarity determining region 1 (CDR1) comprising or consisting of an amino acid sequence defined by positions 44-54 of SEQ ID NO: 4;
      a complementarity determining region 2 (CDR2) comprising or consisting of an amino acid sequence defined by positions 70-76 of SEQ ID NO: 4; and
      a complementarity determining region 3 (CDR3) comprising or consisting of an amino acid sequence defined by positions 109-117 of SEQ ID NO: 4;
   and wherein the composition does not contain second antibodies comprising a light chain variable region comprising:
      a complementarity determining region 1 (CDR1) comprising or consisting of an amino acid sequence defined by positions 48-58 of SEQ ID NO: 11;
      a complementarity determining region 2 (CDR2) comprising or consisting of an amino acid sequence defined by positions 74-80 of SEQ ID NO: 11; and
      a complementarity determining region 3 (CDR3) comprising or consisting of an amino acid sequence defined by positions 113-121 of SEQ ID NO: 11.

2. The composition according to claim 1, wherein the first antibodies and/or antigen binding fragments thereof are any one or more of monoclonal antibodies, humanised antibodies, chimeric antibodies, multimeric antibodies, and/or synthetic antibodies.

3. The composition according to claim 2, wherein the first antibodies and/or antigen binding fragments thereof are chimeric antibodies comprising:
   (a) a heavy chain constant region comprising or consisting of an amino acid sequence as defined in residues 138-467 of SEQ ID NO: 7; and
   (b) a light chain constant region comprising or consisting of an amino acid sequence as defined in residues 128-234 of SEQ ID NO: 8.

4. The composition according to claim 1, wherein the antigen binding fragments are any one or more of single chain variable fragments (scFv), single chain variable fragments (scFv) comprising a sequence as defined in SEQ ID NO: 9, variable domain (Fv) fragments, fragment antigen binding (Fab) fragments, F(ab)2 fragments, peptides, or proteolytic fragments containing an epitope binding region.

5. The composition according to claim 1, wherein the first antibodies comprise or consist of a heavy chain sequence as defined by positions 20-461 of SEQ ID NO: 3 and a light chain sequence as defined by positions 21-234 of SEQ ID NO: 4.

6. The composition according to claim 1, wherein the cytotoxic agent is selected from the group consisting of:
   (a) an adrenocortical suppressant, an alkylating agent, an alkyl sulfonate, an anthracycline, an anti-angiogenic agent, an antibiotic, an antimetabolite, an antimitotic, an auristatin, a calicheamycin, a camptothecin, a COX-2 inhibitor, an enzyme inhibitor, an epipodophyllotoxin, an ethylenimine derivative, a folic acid analog, an HDAC inhibitor, a heat shock protein (HSP90) inhibitor, a hormone antagonist, a maytansinoid, a methyl hydrazine derivative, an mTOR inhibitor, a nitrogen mustard, a nitrosourea, a platinum coordination complex, a pro-apoptotic agent, a proteosome inhibitor, a purine analog, a pyrimidine analog, a radioisotope, a substituted urea, a taxane, triazene, a tubulin inhibitor, a tyrosine kinase inhibitor, and a *vinca* alkaloid; or the group consisting of
   (b) afatinib, aplidin, anastrozole, anthracyclines, AVL-101, AVL-291, axitinib, azaribine, bendamustine, bleomycin, bortezomib, bosutinib, bryostatin-1, busulfan, camptothecans, carboplatin, calicheamycin, camptothecin, carboplatin, carmustine, celecoxib, chlorambucil, cisplatinum, cladribine, COX-2 inhibitors, crizotinib, cyano-morpholino doxorubicin, cyclophosphamide, cytarabine, dacarbazine, dactinomycin, dasatinib, daunorubicin, dinaciclib, 3',5'-O-dioleoyl-FudR (FUdR-d0), DM1, DM3, DM4, docetaxel, doxorubicin, doxorubicin glucuronide, duocarmycin, endostatin, entinostat, epidophyllotoxin, epirubicin glucuronide, erlotinib, estramustine, estrogen receptor binding agents, etoposide glucuronide, etoposide phosphate, etoposide (VP16), exemestane, farnesyl-protein transferase inhibitors, fingolimod, flavopiridol, floxuridine (FUdR), fludarabine, 5-fluorouracil, flutamide, fostamatinib, ganetespib, GDC-0834, gefitinib, gemcitabine, GS-1101, 10-hydroxycamptothecin, hydroxyurea, ibrutinib, idarubicin, idelalisib, ifosfamide, imatinib, irinotecan (CPT-11), lapatinib, lenolidamide, leucovorin, LFM-A13, lomustine, mechlorethamine, melphalan, mercaptopurine, 6-mercaptopurine, methotrexate, mithramycin, mitomycin, mitotane, mitoxantrone, monomethylauristatin D (MMAD), monomethylauristatin E (MMAE), monomethylauristatin F (MMAF), navelbine, neratinib, nilotinib, nitrosurea, olaparib, paclitaxel, PCI-32765, pentostatin, plicomycin, a 2-PDox pro-drug (pro-2-PDox), procarbazine, PSI-341, 2-pyrrolinodoxorubicine (2-PDox), raloxifene, semustine, SN-38, sorafenib, streptozocin, SU1 1248, sunitinib, tamoxifen, temazolomide, teniposide, thalidomide, thioguanine, thiotepa, topotecan, transplatinum, uracil mustard, vatalanib, vinblastine, *vinca* alkaloids, vincristine, vinorelbine, and ZD 1839.

7. The composition according to claim 1, wherein the cytotoxic agent is
   a radioisotope.

8. The composition according to claim 7, wherein the radioisotope is selected from the group consisting of: 90Y, 188Re, 166Ho, 165Dy, 109Pd, 111Ag, 186Re, 198Au, 153Sm, 64Cu, 177Lu, 131I, 125I, 67Cu, 175Yb, 166Dy, 169Er, 212Bi, 213Bi, 225Ac, 212Pb, 66Ga, 67Ga, 68Ga, 64Cu, 86Y, 94mTc, and 89Zr.

9. The composition according to claim 1, wherein the cytotoxic agent is a prodrug designed for activation upon uptake into an endosome or lysosome of said prostate, bladder, and/or pancreatic cancer cell.

* * * * *